US010596188B2

(12) United States Patent
Kevil

(10) Patent No.: US 10,596,188 B2
(45) Date of Patent: *Mar. 24, 2020

(54) USE OF NITRITE SALTS IN TREATING TISSUE DAMAGE

(71) Applicant: Christopher Kevil, Shreveport, LA (US)

(72) Inventor: Christopher Kevil, Shreveport, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/440,581

(22) Filed: Feb. 23, 2017

(65) Prior Publication Data

US 2017/0224725 A1    Aug. 10, 2017

Related U.S. Application Data

(60) Division of application No. 14/104,411, filed on Dec. 12, 2013, now Pat. No. 9,579,344, which is a continuation of application No. 13/378,530, filed as application No. PCT/US2010/036269 on May 26, 2010, now abandoned.

(60) Provisional application No. 61/268,926, filed on Jun. 18, 2009.

(51) Int. Cl.
*A61K 33/00* (2006.01)
*A61K 33/06* (2006.01)
*A61K 38/18* (2006.01)
*A61K 45/06* (2006.01)

(52) U.S. Cl.
CPC .............. *A61K 33/00* (2013.01); *A61K 33/06* (2013.01); *A61K 38/18* (2013.01); *A61K 45/06* (2013.01)

(58) Field of Classification Search
CPC .. A61K 2300/00; A61K 33/00; A61K 31/095; A61K 31/137; A61K 31/381; A61K 31/445; A61K 45/06; A61K 9/0053; A61K 9/0014; A61K 9/0019; A61K 9/06; A61K 9/08; A61K 9/20; A61K 9/28; A61K 9/48; A61K 33/06; A61K 31/145; A61K 33/02; A61K 36/16; A61K 36/481; A61K 36/61; A61K 36/67; A61K 36/74; A61K 36/752; A61K 36/79; A61K 36/88; A61K 36/9068; A61K 9/2068; A61K 9/2866; A61K 9/4866; A61K 9/5042; C01B 21/50; A23L 33/10; A23L 33/105; A23L 33/16

See application file for complete search history.

(56) References Cited

U.S. PATENT DOCUMENTS

| | | |
|---|---|---|
| 4,650,484 A | 3/1987 | Shaw et al. |
| 5,122,384 A | 6/1992 | Paradissis et al. |
| 5,489,610 A | 2/1996 | Fung et al. |
| 5,648,101 A | 7/1997 | Tawashi |
| 5,707,984 A | 1/1998 | Tjoeng et al. |
| 5,770,645 A | 6/1998 | Stamler et al. |
| 6,641,839 B1 | 11/2003 | Geoghegan et al. |
| 6,709,681 B2 | 3/2004 | Benjamin et al. |
| 6,962,717 B1 | 11/2005 | Huber et al. |
| 7,048,951 B1 | 5/2006 | Seitz et al. |
| 7,371,415 B1 | 5/2008 | Wuh et al. |
| 2003/0219495 A1 | 11/2003 | Juneau et al. |
| 2005/0113409 A1 | 5/2005 | Connor et al. |
| 2006/0083824 A1 | 4/2006 | Manning et al. |
| 2006/0182815 A1* | 8/2006 | Gladwin .............. A61K 31/519 424/718 |
| 2007/0010571 A1 | 1/2007 | Garvey et al. |
| 2007/0154569 A1 | 7/2007 | Gladwin et al. |
| 2008/0193385 A1* | 8/2008 | Maibach .............. A61K 9/0014 424/43 |
| 2009/0048219 A1 | 2/2009 | Garvey |
| 2009/0196930 A1 | 8/2009 | Surber et al. |
| 2010/0092441 A1* | 4/2010 | Lundberg ............... A61K 31/05 424/93.45 |
| 2010/0203172 A1 | 8/2010 | Sherman et al. |
| 2010/0247682 A1 | 9/2010 | Gladwin et al. |
| 2011/0086069 A1 | 4/2011 | Kevil et al. |
| 2011/0311653 A1* | 12/2011 | Kevil ..................... A61K 33/00 424/696 |
| 2012/0237617 A1 | 9/2012 | Kevil |
| 2013/0209584 A1 | 8/2013 | Kevil et al. |

FOREIGN PATENT DOCUMENTS

| | | |
|---|---|---|
| EP | 1 336 602 A1 | 8/2003 |
| WO | 00/03725 A1 | 1/2000 |
| WO | 00/53193 A1 | 9/2000 |
| WO | WO-0110406 A2 * | 2/2001 ............. A61K 31/00 |

(Continued)

OTHER PUBLICATIONS

Javed et al (Therapeutic Advances in Chronic Disease, 2015, vol. 6, pp. 15-28).*
Kihara (Diabetologia, 1995, vol. 38, pp. 914-918).*
Tilton et al (Podiatry Today, Mar. 2009, vol. 22).*
Juster-Switlyk et al (F1000 Research, 2016, vol. 5, pp. 1-7) (Year: 2016).*
Dinarello (European Journal of Immunology, 2007, vol. 37, pp. S34-S45) (Year: 2007).*
Ustyugova et al (Archives of Environmental Contamination and Toxicology, 2002, vol. 43, pp. 270-276). (Year: 2002).*
Stokes et al, American Journal of Physiology Heart Circ Physiol, Feb. 27, 2009, vol. 296, H1281-H1288 See Parent Application.

(Continued)

*Primary Examiner* — Mark V Stevens
(74) *Attorney, Agent, or Firm* — Davis & Bujold PLLC; Charles G. Holoubek

(57) ABSTRACT

A method of treating neuropathy in a subject, the method comprising identifying a subject who has neuropathy; and administering to the subject a pharmaceutical composition comprising one of inorganic nitrite and a pharmaceutically acceptable salt thereof.

17 Claims, 44 Drawing Sheets

(56) References Cited

FOREIGN PATENT DOCUMENTS

| WO | 2005/004884 | A2 | 1/2005 | |
|---|---|---|---|---|
| WO | 2006/128032 | A2 | 11/2006 | |
| WO | 2008/105730 | A1 | 9/2008 | |
| WO | 2008/105731 | A1 | 9/2008 | |
| WO | 2008/153762 | A2 | 12/2008 | |
| WO | 2009/065142 | A2 | 5/2009 | |
| WO | WO-2009065142 | A2 * | 5/2009 | ............ A61K 33/00 |
| WO | 2010/036236 | A1 | 4/2010 | |
| WO | 2010/147742 | A2 | 12/2010 | |
| WO | 2011/047161 | A1 | 4/2011 | |
| WO | 2012/135623 | A1 | 10/2012 | |
| WO | 2012/142413 | A2 | 10/2012 | |

OTHER PUBLICATIONS

Tripatara et al (Journal of the American Society of Nephrology, Feb. 2007, vol. 18, pp. 570-580) See Parent Application.
Allen et al., "Plasma Nitrite Response and Arterial Reactivity Differentiate Vascular Health and Performance", Nitric Oxide 20:231-237 (2009) See Parent Application.
Blood et al., In vitro and in Vivo Kinetic Handling of Nitrite in Blood: Effects of Varying Heloglobin Oxygen Saturation:, Am J Phsiol Heart Circ Physiol. 293: H-1508-H1517 (2007) See Parent Application.
Cosby et al., "Nitrite Reduction to Nitric Oxide by Deoxyhemoglobin Vasodilates the Human Circulation", Nat Med. 9(12):1498-1505 (2003) See Parent Application.
Croft et al., "Ultrastructural Studies of Wound Healing in Mouse Skin", J Ant. 106:63-77 (1970) See Parent Application.
Dejam et al., "Nitrite Infusion in Humans and Nonhuman Primates: Endocrine Effects, Pharmacokinetics, and Tolerance Formation", Circulation 116:1821-1831 (2007) See Parent Application.
Duranski et al., "Cytoprotective Effects of Nitrite During in Vivo Ischemia-Reperfusion of the Heart and Liver", J Clin Invest. 115(5):1232-40 (2005) See Parent Application.
Greenway et al., "Single-Dose Pharmacokinetics of Different Oral Sodium Nitrite Formulations in Diabetes Patients", Diabetes Technol Ther. 14(7):552-560 (2012) See Parent Application.
Hunault et al., "Biovailability of Sodium Nitrite from an Aqueous Solution in Healthy Adults", Toxic Lett. 190:48-53 (2009) See Parent Application.

"In High Blood Pressure", The Canadian Medical Associates Journal p. xliii, (1928) See Parent Application.
Jacoby et al., "Acute Myocardial Infraction in the Diabetic Patient: Pathophysiology, Clinical Course and Prognosis", J Am Coll Cardiol. 20(3):736-44 (1992) See Parent Application.
Kenjale et al., "Dietary Nitrate Supplementation Enhances Exercise Performance in Peripheral Arterial Disease", J Appl Physiol. 110:1582-1591 (2011) See Parent Application.
Kohn et al., "Pharmacokinetics of Sodium Nitrite-Induced Methemoglobinemia in the Rat", Drug Metab Dispos. 30(6):676-683 (2002) See Parent Application.
Kumar et al., "Chronic Sodium Nitrite Therapy Augments Ischemia-Induced Angiogenesis and Arteriogenesis", PNAS 105(21):7540-7545 (2008) See Parent Application.
Mazzone et al., "A Lifeline for Suffocating Tissues", Nature, 453:1194-1195 (2008) See Parent Application.
Modin et al., "Nitrite-Derived Nitric Oxide: A Possible Mediator of 'Acidic-Metabolic' Vasodilation", Acta Physiol Scand. 171:9-16 (2001) See Parent Application.
Moshage et al., "Nitrite and Nitrate Determinations in Plasma: A Critical Evaluation", Clin Shem. 41(6):892-896 (1995) See Parent Application.
Namba et al., "Angiogenesis Induced by Endothelial Nitric Oxide Synthase Gene through Vascular Endothelial Growth Factor Expression in a Rat Hindlimb Ischemia Model", Circulation 108:2250-2257 (2003) See Parent Application.
"Peripheral Arterial Disease in People with Diabetes", Diabetes Care 26(12):3333-3341 (2003) See Parent Application.
Presely et al., "Acute Effect of a High Nitrate Diet on Brain Perfusion in Older Adults", Nitric Oxide 24:34-42 (2011) See Parent Application.
Sun et al., "Measurement of Nitric Oxide Production in Biological Systems by Using Griess Reaction Assay", Sensors 3:276-284 (2003) See Parent Application.
Tripathi et al., "Effect of Superoxide Dismutase and Acidified Sodium Nitrite on Infract Size Following Ischemia and Reperfusion in Dogs", Indian J Physiol Parmacol. 41(3):248-56 (1997) See Parent Application.
Van Velzen et al., "The Oral Bioavailability of Nitrate from Nitrate-Rich Vegetables in Humans", Toxicol Lett. 181:177-181 (2008) See Parent Application.
Weller et al., "The Effects of Topical Treatment with Acidified Nitrite on Wound Healing in Normal and Diabetic Mice", Nitric Oxide. 15(4):395-9 (2006) See Parent Application.

* cited by examiner

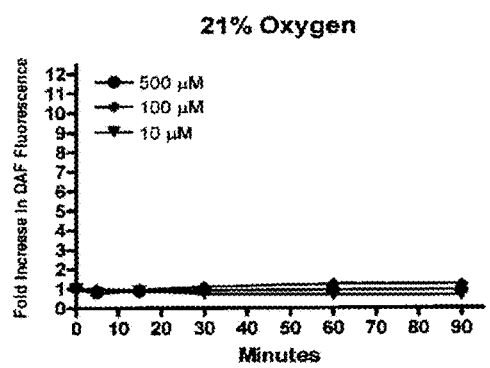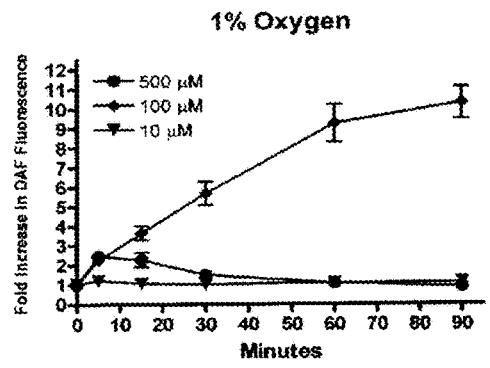
Figure 13A                    Figure 13B

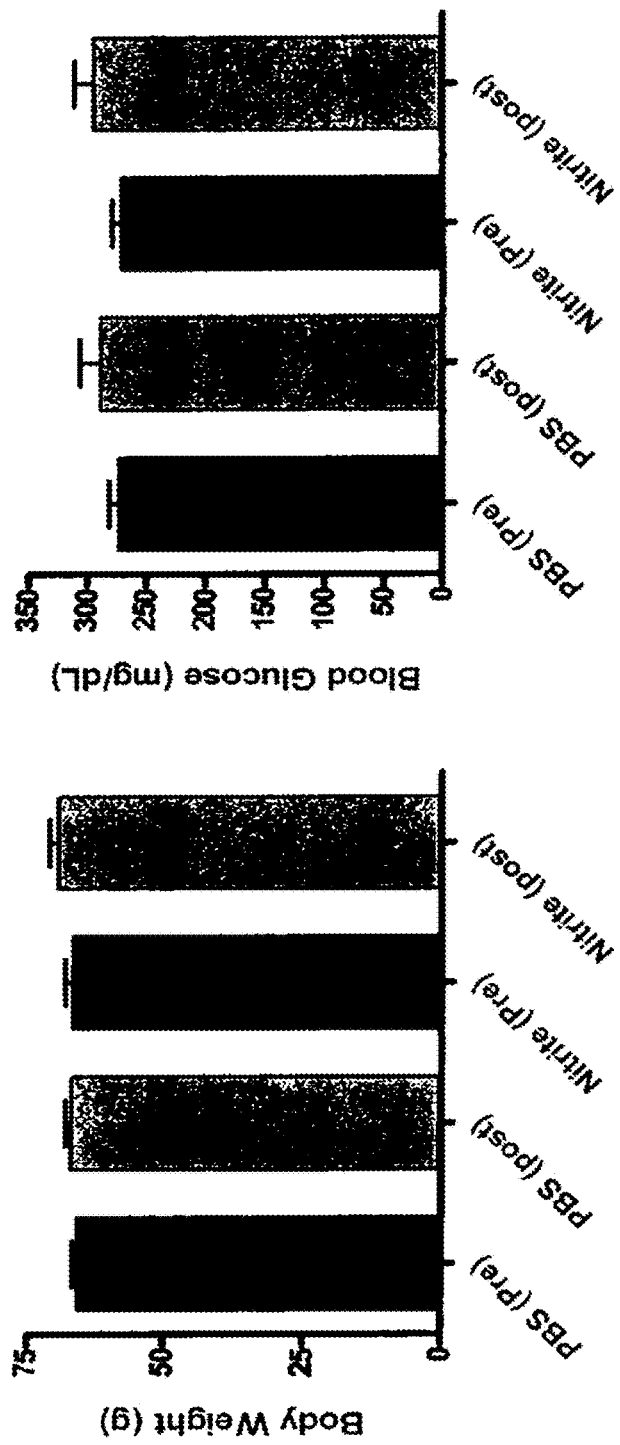

*p<0.01 normoxia versus hypoxia

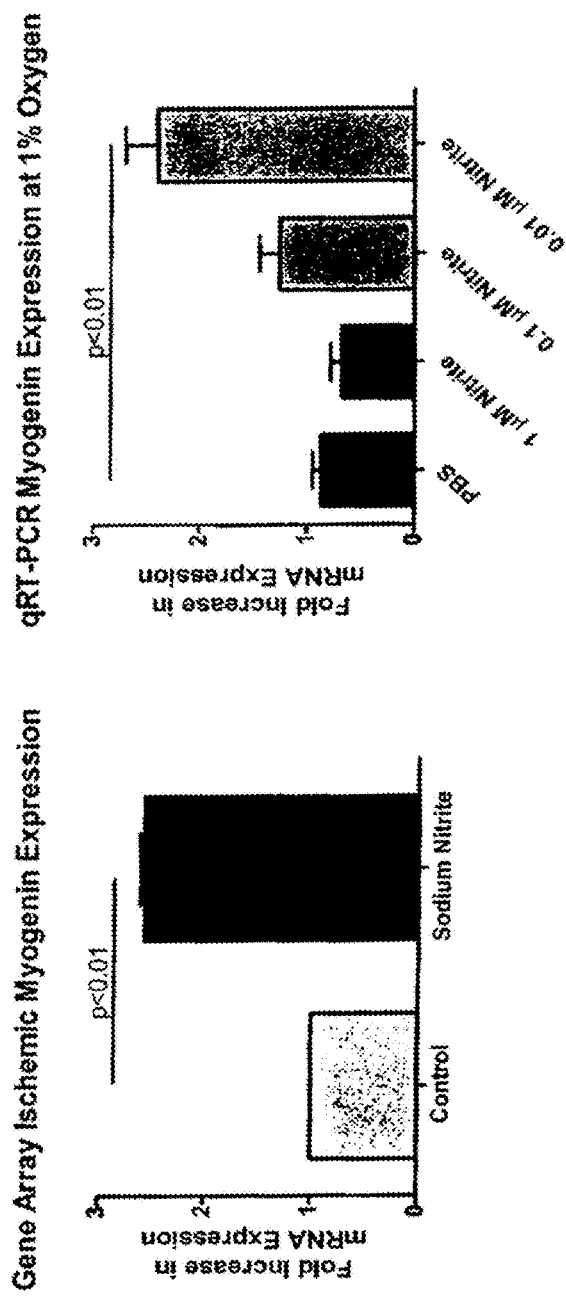

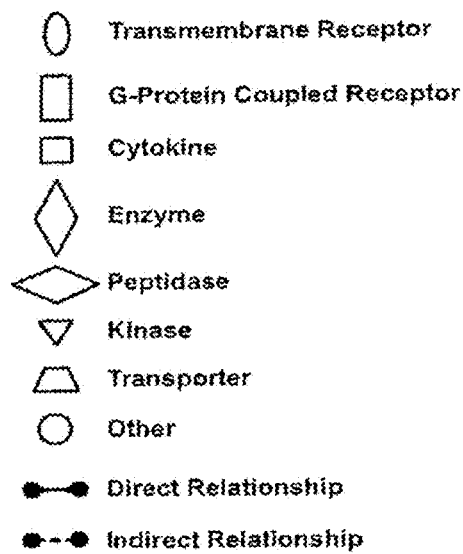

FIG. 28A

Table 1: Differentially expressed genes at day 3 of nitrite therapy

| Gene Name | Accession# | Ratio | SEM | P Value |
|---|---|---|---|---|
| Metallothionein 4 | NM_008631 | 6.01 | 0.03 | 0.018 |
| Myosin, heavy polypeptide 7, cardiac muscle, beta | NM_080728 | 5.35 | 0.003 | 0.014 |
| RIKEN cDNA 1600029D21 gene | BC022950 | 4.98 | 0.016 | 0.0001 |
| Glutathione S-transferase, alpha 2 (Yc2) | NM_008182 | 4.38 | 0.012 | 0.001 |
| Troponin I, skeletal, slow 1 | NM_021467 | 4.23 | 0.002 | 0.017 |
| Troponin T1, skeletal, slow | NM_011618 | 4.15 | 0.003 | 0.035 |
| Four and a half LIM domains 1 | BF466856 | 4.03 | 0.004 | 0.004 |
| Metallothionein 3 | NM_013603 | 3.88 | 0.006 | 0.026 |
| Prostaglandin reductase 2 | BE283373 | 3.79 | 0.007 | 0.002 |
| Myosin, light polypeptide 2, regulatory, cardiac, slow | NM_010861 | 3.56 | 0.002 | 0.047 |
| Troponin C, cardiac/slow skeletal | NM_009393 | 3.49 | 0.001 | 0.038 |
| DIX domain containing 1 | BB758432 | 3.39 | 0.009 | 0.004 |
| Flavin containing monooxygenase 5 | NM_010232 | 3.33 | 0.04 | 0.005 |
| zinc finger protein 697 | BC002224 | 3.28 | 0.02 | 0.012 |
| Park2 co-regulated | AK005771 | 3.19 | 0.007 | 0.001 |
| Kin of IRRE like 3 (Drosophila) | AK005197 | 3.17 | 0.055 | 0.025 |
| Potassium voltage-gated channel, subfamily Q, member 5 | AV362204 | 3.12 | 0.028 | 0.001 |
| DnaJ (Hsp40) homolog, subfamily A, member 4 | NM_021422 | 3.05 | 0.001 | 0.004 |
| Myomesin family, member 3 | AW553161 | 2.99 | 0.006 | 0.006 |
| ATPase, (Na+)/K+ transporting, beta 4 polypeptide | NM_133690 | 2.89 | 0.012 | 0.005 |
| Ankyrin repeat domain 2 (stretch responsive muscle) | NM_020033 | 2.86 | 0.0001 | 0.006 |
| Chemokine (C-X-C motif) receptor 6 | AF301018 | 2.84 | 0.015 | 0.028 |
| Cysteine and glycine-rich protein 3 | NM_013808 | 2.82 | 0.0001 | 0.007 |
| myosin, heavy polypeptide 2, skeletal muscle, adult | BC008538 | 2.8 | 0.0001 | 0.0001 |
| Troponin T2, cardiac | L47552 | 2.75 | 0.004 | 0.017 |
| Zinc finger protein 64 | BF020964 | 2.7 | 0.019 | 0.032 |
| UDP-Gal:betaGlcNAc beta 1,4-galactosyltransferase, polypeptide 4 | AF158746 | 2.62 | 0.019 | 0.007 |
| RIKEN cDNA 2310002L09 gene | AK009097 | 2.58 | 0.001 | 0.0001 |
| Tropomyosin 3, gamma | NM_022314 | 2.58 | 0.002 | 0.035 |
| Myogenin | NM_031189 | 2.57 | 0.001 | 0.004 |
| Prostaglandin-endoperoxide synthase 2 | M94967 | 2.54 | 0.017 | 0.011 |
| Myozenin 2 | NM_021503 | 2.53 | 0.001 | 0.013 |
| TatD DNase domain containing 1 | BB761179 | 2.53 | 0.002 | 0.003 |
| Transcribed locus | BM730637 | 2.53 | 0.008 | 0.001 |
| Transcribed locus | AV231357 | 2.51 | 0.001 | 0.0001 |
| Transcribed locus | AV346607 | 2.51 | 0.017 | 0.01 |
| Cysteine-rich C-terminal 1 | AK009010 | 2.5 | 0.033 | 0.009 |
| Glycogen synthase 1, muscle | NM_030678 | 2.49 | 0.001 | 0.0001 |
| Solute carrier family 22 (organic cation transporter), member 4 | BC010590 | 2.49 | 0.011 | 0.031 |
| Solute carrier family 16 (monocarboxylic acid transporters), member 3 | NM_030696 | 2.48 | 0.0001 | 0.0001 |
| Chloride intracellular channel 5 | BB610000 | 2.47 | 0.003 | 0.011 |
| Transmembrane protein 143 | AK013719 | 2.47 | 0.006 | 0.01 |
| HECT domain containing 2 | AW114007 | 2.46 | 0.013 | 0.034 |

FIG. 28B

| | | | | |
|---|---|---|---|---|
| UEV and lactate/malate dehyrogenase domains | NM_016855 | 2.46 | 0.014 | 0.007 |
| Cyclic AMP-regulated phosphoprotein, 21 | NM_033264 | 2.45 | 0.005 | 0.005 |
| Fibroblast growth factor 13 | AF020737 | 2.43 | 0.004 | 0.001 |
| RIKEN cDNA 8030451F13 gene | AW743000 | 2.43 | 0.001 | 0.006 |
| Cadherin 5 | NM_009868 | 2.41 | 0.009 | 0.013 |
| Mus musculus tumor-associated antigen 1 (Taa1), mRNA. | NM_009310 | 2.39 | 0.005 | 0.026 |
| TEA domain family member 4 | D87965 | 2.38 | 0.01 | 0.0001 |
| Transcribed locus | BB322227 | 2.38 | 0.001 | 0.007 |
| Lactate dehydrogenase B | AV219418 | 2.37 | 0.002 | 0.004 |
| LIM and cysteine-rich domains 1 | BC019124 | 2.37 | 0.0001 | 0.011 |
| Transcribed locus | BM730637 | 2.33 | 0.008 | 0.0001 |
| Rhomboid, veinlet-like 1 (Drosophila) | BC021549 | 2.32 | 0.004 | 0.002 |
| RIKEN cDNA 4833439L19 gene | NM_029241 | 2.32 | 0.002 | 0.002 |
| Smoothelin-like 1 | NM_024230 | 2.29 | 0.002 | 0.013 |
| Target of myb1-like 2 (chicken) | BM226574 | 2.29 | 0.01 | 0.003 |
| Tumor necrosis factor receptor superfamily, member 19 | AF167554 | 2.29 | 0.019 | 0.007 |
| Predicted gene, ENSMUSG00000074670 | BC002189 | 2.26 | 0.015 | 0.012 |
| Sterile alpha motif domain containing 4 | BB626348 | 2.26 | 0.012 | 0.036 |
| Ubiquitin-conjugating enzyme E2G 2 | AF296657 | 2.26 | 0.002 | 0.005 |
| Cell growth regulator with EF hand domain 1 | BC023116 | 2.25 | 0.005 | 0.005 |
| Heat shock protein family, member 7 (cardiovascular) | BG968304 | 2.23 | 0.0001 | 0.005 |
| Small proline-rich protein 1A | NM_009264 | 2.23 | 0.008 | 0.011 |
| FXYD domain-containing ion transport regulator 6 | AB032010 | 2.22 | 0.003 | 0.021 |
| Plasmacytoma variant translocation 1 | BI453402 | 2.2 | 0.033 | 0.042 |
| Uridine-cytidine kinase 2 | NM_030724 | 2.2 | 0.001 | 0.001 |
| DNA-damage-inducible transcript 4 | AK017926 | 2.19 | 0.001 | 0.011 |
| Expressed sequence AU040829 | BB079908 | 2.18 | 0.003 | 0.004 |
| Myosin, light polypeptide 4 | NM_010858 | 2.18 | 0.001 | 0.01 |
| Popeye domain containing 2 | NM_022318 | 2.18 | 0.001 | 0.002 |
| Dynamin 1-like | BC027538 | 2.14 | 0.006 | 0.003 |
| ARP1 actin-related protein 1 homolog B (yeast) | BG801851 | 2.13 | 0.001 | 0.002 |
| Integrin alpha 7 | NM_008398 | 2.13 | 0.001 | 0.001 |
| Sodium channel, voltage-gated, type V, alpha | BB516098 | 2.13 | 0.004 | 0.003 |
| SRY-box containing gene 17 | NM_011441 | 2.13 | 0.003 | 0.013 |
| Neural cell adhesion molecule 1 | NM_010875 | 2.12 | 0.005 | 0.017 |
| Potassium inwardly rectifying channel, subfamily J, member 11 | U73626 | 2.12 | 0.002 | 0.0001 |
| Suppressor of cytokine signaling 3 | BB241535 | 2.12 | 0.001 | 0.002 |
| Transcribed locus | AK017367 | 2.12 | 0.012 | 0.004 |
| ESTs | BB515192 | 2.11 | 0.002 | 0.018 |
| mitochondrial carrier homolog 2 | AV067008 | 2.11 | 0.0001 | 0.016 |
| Purinergic receptor P2Y, G-protein coupled 2 | NM_008773 | 2.11 | 0.004 | 0.003 |
| Solute carrier family 25 (mitochondrial carrier, phosphate carrier), member 25 | BC019978 | 2.11 | 0.001 | 0.013 |
| Transcribed locus, moderately similar to NP_766184.1 SEC24 related gene family, member C [Mus musculus] | AK018074 | 2.11 | 0.018 | 0.042 |
| EH-domain containing 2 | BC027084 | 2.1 | 0.004 | 0.011 |
| Leucine rich repeat protein 1, neuronal | NM_008516 | 2.1 | 0.005 | 0.027 |
| Gene model 129, (NCBI) | BB407125 | 2.09 | 0.005 | 0.004 |
| Transcribed locus | BB766817 | 2.09 | 0.01 | 0.037 |
| Coiled-coil domain containing 109A | AV259428 | 2.08 | 0.007 | 0.004 |

FIG. 28C

| | | | | |
|---|---|---|---|---|
| AHNAK nucleoprotein (desmoyokin) | AK009866 | 2.07 | 0.004 | 0.02 |
| CUB and zona pellucida-like domains 1 | NM_008411 | 2.07 | 0.016 | 0.002 |
| Keratin 18 | NM_010664 | 2.07 | 0.016 | 0.03 |
| Mus musculus RIKEN cDNA 1110055E19 gene (1110055E19Rik), mRNA. | NM_026839 | 2.07 | 0.0001 | 0.011 |
| Vitronectin | BB251864 | 2.06 | 0.013 | 0.026 |
| Solute carrier family 8 (sodium/calcium exchanger), member 3 | NM_080440 | 2.06 | 0.006 | 0.009 |
| ESTs | BB386239 | 2.04 | 0.011 | 0.036 |
| RIKEN cDNA 1700052N19 gene | NM_024261 | 2.04 | 0.009 | 0.003 |
| RIKEN cDNA 2900073G15 gene | NM_026064 | 2.04 | 0.001 | 0.003 |
| Transcribed locus | AW553649 | 2.04 | 0.025 | 0.03 |
| Transcribed locus | BB764453 | 2.04 | 0.004 | 0.002 |
| TBC1 domain family, member 1 | BB501891 | 2.03 | 0.01 | 0.014 |
| Calsequestrin 2 | NM_009814 | 2.02 | 0.002 | 0.001 |
| Coagulation factor II (thrombin) receptor-like 1 | NM_007974 | 2.02 | 0.006 | 0.027 |
| Myosin light chain 2, precursor lymphocyte-specific | NM_021611 | 2.02 | 0.012 | 0.028 |
| EGL nine homolog 3 (C. elegans) | BB284358 | 2.01 | 0.001 | 0.006 |
| CDNA sequence BC048679 | AV360837 | 2 | 0.016 | 0.023 |
| Methylcrotonoyl-Coenzyme A carboxylase 2 (beta) | BI155184 | 2 | 0.01 | 0.001 |
| Paired-like homeodomain transcription factor 2 | U80011 | 2 | 0.003 | 0.034 |
| TAF7 RNA polymerase II, TATA box binding protein (TBP)-associated factor | AV213552 | 2 | 0.015 | 0.002 |
| Claspin homolog (Xenopus laevis) | BG067086 | 0.5 | 0.003 | 0.022 |
| ESTs, Moderately similar to S12207 hypothetical protein (M.musculus) | BM119933 | 0.5 | 0.007 | 0.001 |
| Myosin Va | NM_010864 | 0.5 | 0.001 | 0.003 |
| Transcribed locus | BM213788 | 0.5 | 0.009 | 0.047 |
| Transcribed locus | BG067469 | 0.5 | 0.004 | 0.008 |
| Zinc finger, RAN-binding domain containing 3 | BM228797 | 0.5 | 0.002 | 0.006 |
| DnaJ (Hsp40) homolog, subfamily B, member 14 | BE952491 | 0.498 | 0.003 | 0.013 |
| ESTs | BB206454 | 0.498 | 0.004 | 0.005 |
| ESTs | BB467915 | 0.498 | 0.007 | 0.009 |
| Glia maturation factor, gamma | NM_022024 | 0.498 | 0.001 | 0.011 |
| RIKEN cDNA B430201A12 gene | BB325849 | 0.498 | 0.001 | 0.0001 |
| Solute carrier family 37 (glycerol-3-phosphate transporter), member 2 | BC022752 | 0.498 | 0.002 | 0.017 |
| Splicing factor proline/glutamine rich (polypyrimidine tract binding protein associated) | BI738328 | 0.498 | 0.001 | 0.005 |
| Tousled-like kinase 2 (Arabidopsis) | BM198864 | 0.498 | 0.008 | 0.016 |
| Transcribed locus | AA266723 | 0.498 | 0.004 | 0.025 |
| DNA segment, Chr 8, ERATO Doi 82, expressed | BM195829 | 0.495 | 0.003 | 0.029 |
| RIKEN cDNA 2810417H13 gene | AK017673 | 0.495 | 0.0001 | 0.005 |
| Transcribed locus | BB362579 | 0.495 | 0.009 | 0.019 |
| Transcribed locus | BB192700 | 0.495 | 0.004 | 0.025 |
| Activated leukocyte cell adhesion molecule | AV315205 | 0.493 | 0.009 | 0.007 |
| ESTs | BB499275 | 0.493 | 0.008 | 0.003 |
| F-box protein 5 | AK011820 | 0.493 | 0.003 | 0.014 |
| Transmembrane protein 106A | BC022145 | 0.493 | 0.001 | 0.005 |
| EST X83313 | BG065719 | 0.49 | 0.006 | 0.018 |
| ESTs | AI604411 | 0.49 | 0.006 | 0.005 |

FIG. 28D

| | | | | |
|---|---|---|---|---|
| ESTs, Weakly similar to NED4 MOUSE NEDD-4 PROTEIN (M.musculus) | AI593288 | 0.49 | 0.008 | 0.003 |
| Jumonji, AT rich interactive domain 1C (Rbp2 like) | BB165753 | 0.49 | 0.013 | 0.033 |
| Rho GTPase activating protein 9 | AU043488 | 0.49 | 0.007 | 0.006 |
| Shc SH2-domain binding protein 1 | NM_011369 | 0.49 | 0.002 | 0.006 |
| Sterol O-acyltransferase 1 | BG064396 | 0.49 | 0.001 | 0.003 |
| Transcribed locus | BB104669 | 0.49 | 0.003 | 0.009 |
| cyclin B1 | NM_007629 | 0.488 | 0.002 | 0.016 |
| FERM domain containing 4B | BB009122 | 0.488 | 0.001 | 0.009 |
| Fermitin family homolog 3 (Drosophila) | BG066664 | 0.488 | 0.001 | 0.004 |
| Testis-specific kinase 2 | BQ179435 | 0.488 | 0.005 | 0.001 |
| Transcribed locus | BB480970 | 0.488 | 0.004 | 0.007 |
| CAP, adenylate cyclase-associated protein 1 (yeast) | NM_007598 | 0.485 | 0.011 | 0.011 |
| CDNA sequence BC052328 | BM224662 | 0.485 | 0.001 | 0.007 |
| DBF4 homolog (S. cerevisiae) | NM_013726 | 0.485 | 0.001 | 0.004 |
| ESTs | BG071091 | 0.485 | 0.006 | 0.007 |
| FYN binding protein | BB157866 | 0.485 | 0.001 | 0.001 |
| Mucolipin 2 | AK014467 | 0.485 | 0.008 | 0.036 |
| RIKEN cDNA 4921513D23 gene | BB123487 | 0.485 | 0.005 | 0.005 |
| RIKEN cDNA 9430034F23 gene | AK020456 | 0.485 | 0.013 | 0.036 |
| Transcribed locus | AU020421 | 0.485 | 0.006 | 0.024 |
| Transcribed locus | AW537708 | 0.485 | 0.0001 | 0.003 |
| annexin A6 | AK013026 | 0.483 | 0.005 | 0.001 |
| ESTs | BB373572 | 0.483 | 0.007 | 0.015 |
| PR domain containing 1, with ZNF domain | NM_007548 | 0.483 | 0.006 | 0.005 |
| T-box 1 | AF326960 | 0.483 | 0.002 | 0.022 |
| Dedicator of cyto-kinesis 2 | NM_033374 | 0.481 | 0.001 | 0.021 |
| ESTs | BM199910 | 0.481 | 0.003 | 0.003 |
| Heme oxygenase (decycling) 1 | NM_010442 | 0.481 | 0.0001 | 0.006 |
| Interferon, alpha-inducible protein 27 | AY090098 | 0.481 | 0.001 | 0.007 |
| Leukocyte immunoglobulin-like receptor, subfamily B (with TM and ITIM domains), member 3 | U96693 | 0.481 | 0.002 | 0.004 |
| Liver glycogen phosphorylase | NM_133198 | 0.481 | 0.001 | 0.001 |
| RIKEN cDNA 2310045N14 gene | AK009831 | 0.481 | 0.002 | 0.016 |
| RIKEN cDNA A230054D04 gene | BB542960 | 0.481 | 0.004 | 0.039 |
| Transcribed locus | BB235876 | 0.481 | 0.004 | 0.003 |
| Transcribed locus | BM244144 | 0.481 | 0.006 | 0.004 |
| Transcribed locus | BB753814 | 0.481 | 0.01 | 0.012 |
| Transcribed locus, strongly similar to NP_780438.2 serine/arginine repetitive matrix 2 [Mus musculus] | BB821417 | 0.481 | 0.003 | 0.0001 |
| Baculoviral IAP repeat-containing 6 | BB527646 | 0.478 | 0.007 | 0.005 |
| Cytoskeleton-associated protein 4 | BB312117 | 0.478 | 0.001 | 0.0001 |
| Dynactin 5 | NM_011121 | 0.478 | 0.003 | 0.034 |
| Interferon induced transmembrane protein 1 | BC027285 | 0.478 | 0.002 | 0.025 |
| Receptor (calcitonin) activity modifying protein 2 | AF146523 | 0.478 | 0.0001 | 0.014 |
| Rho GTPase activating protein 17 | BB749468 | 0.478 | 0.005 | 0.041 |
| CD300 antigen like family member B | BB230267 | 0.476 | 0.002 | 0.004 |
| Epidermal growth factor receptor pathway substrate 8 | NM_007945 | 0.476 | 0.001 | 0.0001 |
| lysosomal-associated protein transmembrane 5 | BB218107 | 0.476 | 0.0001 | 0.001 |
| SERTA domain containing 4 | BQ174721 | 0.476 | 0.002 | 0.009 |

FIG. 28E

| Description | Accession | | | |
|---|---|---|---|---|
| Transcribed locus | BG076154 | 0.476 | 0.003 | 0.008 |
| Adipose differentiation related protein | NM_007408 | 0.474 | 0.0001 | 0.003 |
| Chitinase 3-like 3 | NM_009892 | 0.474 | 0.001 | 0.038 |
| Collagen, type XII, alpha 1 | AW412729 | 0.474 | 0.004 | 0.014 |
| Coronin, actin binding protein 1A | BB740218 | 0.474 | 0.001 | 0.007 |
| ESTs | BG075224 | 0.474 | 0.01 | 0.045 |
| Fc receptor, IgE, high affinity I, gamma polypeptide | NM_010185 | 0.474 | 0.0001 | 0.002 |
| Transcribed locus | BB202321 | 0.474 | 0.016 | 0.032 |
| Transcribed locus | C85455 | 0.474 | 0.005 | 0.015 |
| Tropomyosin 1, alpha | BM232388 | 0.474 | 0.001 | 0.008 |
| ESTs | BB039073 | 0.472 | 0.006 | 0.017 |
| Solute carrier family 25, member 30 | BB032012 | 0.472 | 0.002 | 0.001 |
| Transcribed locus | AI606033 | 0.472 | 0.005 | 0.031 |
| Transcribed locus | AV330236 | 0.472 | 0.01 | 0.014 |
| Transcribed locus | BM243379 | 0.472 | 0.001 | 0.001 |
| Twinfilin, actin-binding protein, homolog 1 (Drosophila) | BI662615 | 0.472 | 0.003 | 0.026 |
| Mus musculus, Similar to transgelin 2, clone MGC:6300 IMAGE:2654381, mRNA, complete cds | AV212626 | 0.469 | 0.001 | 0.023 |
| Coiled-coil domain containing 109B | NM_025779 | 0.467 | 0.002 | 0.007 |
| Complement component 3a receptor 1 | NM_009779 | 0.467 | 0.0001 | 0.002 |
| Membrane-spanning 4-domains, subfamily A, member 6B | NM_027209 | 0.467 | 0.0001 | 0.002 |
| Regulator of G-protein signaling 18 | BB139986 | 0.467 | 0.006 | 0.02 |
| RIKEN cDNA A630042L21 gene | BB233267 | 0.467 | 0.006 | 0.002 |
| Transcribed locus | BF715043 | 0.467 | 0.001 | 0.0001 |
| Transcribed locus | BB051012 | 0.467 | 0.011 | 0.022 |
| Transcribed locus | BG094104 | 0.467 | 0.005 | 0.002 |
| Transcribed locus | BB433596 | 0.467 | 0.007 | 0.023 |
| CD52 antigen | NM_013706 | 0.465 | 0.0001 | 0.005 |
| Deoxycytidine kinase | BB030204 | 0.465 | 0.001 | 0.005 |
| Epidermal growth factor-containing fibulin-like extracellular matrix protein 1 | BC023060 | 0.465 | 0.001 | 0.004 |
| expressed sequence AV025504 | BB115446 | 0.465 | 0.001 | 0.001 |
| Nuclear transcription factor, X-box binding-like 1 | NM_133921 | 0.465 | 0.002 | 0.011 |
| Transcribed locus | BM203526 | 0.465 | 0.005 | 0.021 |
| High mobility group AT-hook 2 | BB105328 | 0.463 | 0.016 | 0.001 |
| RAP2B, member of RAS oncogene family | BB390705 | 0.463 | 0.003 | 0.001 |
| Transcribed locus | BG074304 | 0.463 | 0.006 | 0.006 |
| UDP-Gal:betaGlcNAc beta 1,4-galactosyltransferase, polypeptide 6 | BG066773 | 0.463 | 0.001 | 0.001 |
| Bone marrow stromal cell antigen 1 | AI647987 | 0.461 | 0.005 | 0.007 |
| Platelet-derived growth factor, C polypeptide | NM_019971 | 0.461 | 0.003 | 0.02 |
| RIKEN cDNA 4930506M07 gene | BB559293 | 0.461 | 0.002 | 0.0001 |
| RIKEN cDNA 4932415G12 gene | AK015136 | 0.461 | 0.018 | 0.039 |
| Signal sequence receptor, gamma | AU022074 | 0.461 | 0.0001 | 0.039 |
| toll-like receptor 13 | BI655907 | 0.461 | 0.001 | 0.012 |
| Chemokine (C-C motif) ligand 9 | AF128196 | 0.459 | 0.0001 | 0.01 |
| EST | AV084904 | 0.459 | 0.0001 | 0.002 |
| ESTs | BG075606 | 0.459 | 0.007 | 0.013 |
| Sperm associated antigen 5 | BM208112 | 0.459 | 0.011 | 0.004 |
| Transcribed locus | BB827631 | 0.459 | 0.003 | 0.003 |

FIG. 28F

| | | | | |
|---|---|---|---|---|
| Transcribed locus | BF165681 | 0.459 | 0.002 | 0.005 |
| ESTs | BB425118 | 0.457 | 0.014 | 0.027 |
| ESTs, Weakly similar to JAK3 MOUSE TYROSINE-PROTEIN KINASE JAK3 (M.musculus) | BG063073 | 0.457 | 0.012 | 0.005 |
| Kinesin family member 2C | NM_134471 | 0.457 | 0.005 | 0.005 |
| Transcribed locus | BE690666 | 0.457 | 0.01 | 0.005 |
| 5-hydroxytryptamine (serotonin) receptor 2B | NM_008311 | 0.455 | 0.006 | 0.022 |
| ESTs | AU040352 | 0.455 | 0.007 | 0.003 |
| ESTs | AV369290 | 0.455 | 0.009 | 0.002 |
| RIKEN cDNA 6330500D04 gene | AV329070 | 0.455 | 0.006 | 0.004 |
| Solute carrier family 15, member 3 | NM_023044 | 0.455 | 0.002 | 0.05 |
| Asp (abnormal spindle)-like, microcephaly associated (Drosophila) | NM_009791 | 0.452 | 0.003 | 0.001 |
| Deleted in lymphocytic leukemia, 2 | AA189481 | 0.452 | 0.007 | 0.009 |
| DNA segment, Chr 10, ERATO Doi 276, expressed | BG066654 | 0.452 | 0.008 | 0.029 |
| ESTs, Weakly similar to GNMSLL retrovirus-related reverse transcriptase homolog - mouse retrotransposon (M.musculus) | AI506532 | 0.452 | 0.003 | 0.012 |
| Phosphatidylinositol-5-phosphate 4-kinase, type II, alpha | AK012196 | 0.452 | 0.003 | 0.001 |
| Protein phosphatase 1H (PP2C domain containing) | AU040848 | 0.452 | 0.003 | 0.001 |
| Structural maintenance of chromosomes 6 | BB056038 | 0.452 | 0.012 | 0.001 |
| Z-DNA binding protein 1 | AK008179 | 0.452 | 0.005 | 0.019 |
| Zwilch, kinetochore associated, homolog (Drosophila) | BC027435 | 0.452 | 0.002 | 0.023 |
| ESTs | BE980962 | 0.45 | 0.007 | 0.0001 |
| ESTs | BB394466 | 0.45 | 0.004 | 0.003 |
| expressed sequence AU015263 | BG070233 | 0.45 | 0.003 | 0.008 |
| Lysosomal acid lipase A | AI596237 | 0.45 | 0.001 | 0.013 |
| Schlafen 2 | NM_011408 | 0.45 | 0.001 | 0.011 |
| Transcribed locus | BF225802 | 0.45 | 0.0001 | 0.002 |
| Ect2 oncogene | NM_007900 | 0.448 | 0.002 | 0.003 |
| Topoisomerase (DNA) II alpha | BB749838 | 0.448 | 0.006 | 0.013 |
| Transcribed locus | BF147024 | 0.448 | 0.02 | 0.008 |
| growth arrest specific 1 /FL=gb:NM_008086.1 | BB550400 | 0.446 | 0.001 | 0.005 |
| Macrophage scavenger receptor 1 | L04274 | 0.446 | 0.01 | 0.02 |
| RIKEN cDNA 2310022G15 gene | BF783360 | 0.446 | 0.003 | 0.015 |
| Transcribed locus | BI685536 | 0.446 | 0.001 | 0.007 |
| Transcribed locus | BB229269 | 0.446 | 0.005 | 0.004 |
| Transcribed locus | AW537708 | 0.446 | 0.003 | 0.025 |
| Fatty acid binding protein 7, brain | NM_021272 | 0.444 | 0.007 | 0.003 |
| Gene model 885, (NCBI) | BE629676 | 0.444 | 0.004 | 0.004 |
| Neurobeachin like 1 | BB022773 | 0.444 | 0.006 | 0.009 |
| Six transmembrane epithelial antigen of prostate 2 | AK015015 | 0.444 | 0.004 | 0.017 |
| Thrombospondin 2 | NM_011581 | 0.444 | 0.001 | 0.006 |
| Transcribed locus, strongly similar to XP_141626.3 PREDICTED: similar to Ubiquitin-conjugating enzyme E2Q (putative) 2 [Mus m | AW550321 | 0.444 | 0.006 | 0.015 |
| Cysteinyl leukotriene receptor 1 | BC027102 | 0.442 | 0.006 | 0.018 |
| Fc receptor, IgG, high affinity I | AF143181 | 0.442 | 0.001 | 0.008 |
| Thyroid hormone receptor interactor 13 | AK010336 | 0.442 | 0.002 | 0.011 |
| Transcribed locus | BB262899 | 0.442 | 0.017 | 0.047 |
| Cathepsin C | BM237633 | 0.439 | 0.004 | 0.007 |
| CD180 antigen | NM_008533 | 0.439 | 0.004 | 0.004 |
| C-type lectin domain family 5, member a | NM_021364 | 0.439 | 0.007 | 0.005 |

FIG. 28G

| Epithelial stromal interaction 1 (breast) | BF020640 | 0.439 | 0.003 | 0.019 |
|---|---|---|---|---|
| Expressed sequence C79407 | BB540053 | 0.439 | 0.005 | 0.002 |
| Kinesin family member 22 | BC003427 | 0.439 | 0.006 | 0.02 |
| Myb-like, SWIRM and MPN domains 1 | BB045598 | 0.439 | 0.009 | 0.047 |
| Discs, large (Drosophila) homolog-associated protein 5 | BM250919 | 0.437 | 0.007 | 0.046 |
| Hyaluronan mediated motility receptor (RHAMM) | BC021427 | 0.437 | 0.003 | 0.002 |
| Maternal embryonic leucine zipper kinase | NM_010790 | 0.437 | 0.003 | 0.048 |
| Transforming growth factor, beta induced | NM_009369 | 0.437 | 0.0001 | 0.0001 |
| Pleckstrin | AF181829 | 0.435 | 0.001 | 0.004 |
| transforming growth factor, beta induced, 68 kDa | BB533460 | 0.435 | 0.0001 | 0.0001 |
| A disintegrin and metallopeptidase domain 12 (meltrin alpha) | NM_007400 | 0.433 | 0.002 | 0.001 |
| Collagen, type I, alpha 2 | BB150460 | 0.433 | 0.008 | 0.009 |
| Transcribed locus | BB490889 | 0.433 | 0.01 | 0.009 |
| Transcribed locus | BB380864 | 0.433 | 0.018 | 0.018 |
| ATPase, class V, type 10A | BM249532 | 0.431 | 0.008 | 0.039 |
| Formin 1 | BB164513 | 0.431 | 0.009 | 0.003 |
| Protein tyrosine phosphatase, receptor type, O | AF295638 | 0.431 | 0.008 | 0.009 |
| Transcribed locus | BB538816 | 0.431 | 0.006 | 0.008 |
| Baculoviral IAP repeat-containing 5 | BC004702 | 0.429 | 0.001 | 0.002 |
| Mitogen-activated protein kinase kinase kinase kinase 1 | BB546619 | 0.429 | 0.007 | 0.014 |
| N-acetylneuraminate pyruvate lyase | BC022734 | 0.429 | 0.001 | 0.017 |
| TAO kinase 1 | BM238077 | 0.429 | 0.008 | 0.003 |
| Apolipoprotein B editing complex 1 | BC003792 | 0.427 | 0.001 | 0.005 |
| DNA segment, Chr 10, ERATO Doi 709, expressed | BG069224 | 0.427 | 0.005 | 0.004 |
| Paternally expressed 3 | AB003040 | 0.427 | 0.001 | 0.002 |
| Transcribed locus | BG067008 | 0.427 | 0.006 | 0.006 |
| Transmembrane protein 97 | NM_133706 | 0.427 | 0.004 | 0.005 |
| Cyclin A2 | X75483 | 0.426 | 0.001 | 0.002 |
| Hypothetical protein LOC100043636 | BE688410 | 0.426 | 0.001 | 0.021 |
| Transcribed locus | AV349116 | 0.426 | 0.002 | 0.01 |
| BCL2-like 11 (apoptosis facilitator) | BB667581 | 0.424 | 0.001 | 0.001 |
| Exonuclease domain containing 1 | BB091183 | 0.424 | 0.009 | 0.038 |
| Ribosome binding protein 1 | NM_133626 | 0.424 | 0.001 | 0.028 |
| Transcribed locus | BM234702 | 0.424 | 0.005 | 0.032 |
| Transcribed locus | BB070941 | 0.424 | 0.007 | 0.011 |
| Sorting nexin 6 | BC025911 | 0.422 | 0.003 | 0.005 |
| Transmembrane protein 100 | NM_026433 | 0.422 | 0.001 | 0.046 |
| Tripartite motif-containing 59 | NM_025863 | 0.422 | 0.003 | 0.018 |
| Complement factor properdin | BB800282 | 0.418 | 0.001 | 0.005 |
| Fidgetin-like 1 | NM_021891 | 0.418 | 0.003 | 0.031 |
| Transcribed locus | BG066234 | 0.418 | 0.004 | 0.006 |
| tripartite motif-containing 34 | AF220142 | 0.418 | 0.003 | 0.029 |
| C-type lectin domain family 4, member a3 | AK014135 | 0.417 | 0.001 | 0.001 |
| Transcribed locus | BE692425 | 0.417 | 0.002 | 0.003 |
| Disabled homolog 2 (Drosophila) | AK017619 | 0.415 | 0.003 | 0.007 |
| promyelocytic leukemia | BB667149 | 0.415 | 0.005 | 0.022 |
| Versican | BM251152 | 0.415 | 0.003 | 0.002 |
| ESTs | BB735884 | 0.413 | 0.009 | 0.004 |
| Transcribed locus | BB420529 | 0.413 | 0.003 | 0.002 |

FIG. 28H

| Gene | Accession | Val1 | Val2 | Val3 |
|---|---|---|---|---|
| Embigin | BG064842 | 0.412 | 0.001 | 0.005 |
| ESTs | BM123108 | 0.412 | 0.017 | 0.049 |
| Interferon activated gene 204 | NM_008329 | 0.412 | 0.003 | 0.022 |
| Transcribed locus | BB367687 | 0.412 | 0.007 | 0.005 |
| Transcribed locus, moderately similar to XP_001477892.1 PREDICTED: hypothetical protein [Mus musculus] | BG862223 | 0.412 | 0.003 | 0.008 |
| UDP glucuronosyltransferase 1 family, polypeptide A6B | D87867 | 0.412 | 0.0001 | 0.001 |
| E1A binding protein p400 | BM236717 | 0.408 | 0.006 | 0.007 |
| RIKEN cDNA 5830411K21 gene | BM220939 | 0.408 | 0.002 | 0.007 |
| Transmembrane protein 8 (five membrane-spanning domains) | NM_021793 | 0.408 | 0.005 | 0.018 |
| Coagulation factor XIII, A1 subunit | NM_028784 | 0.407 | 0.0001 | 0.002 |
| ESTs, Weakly similar to TYROSINE-PROTEIN KINASE JAK3 (M.musculus) | BB441213 | 0.407 | 0.008 | 0.007 |
| 5-nucleotidase domain containing 2 | BC011230 | 0.405 | 0.002 | 0.002 |
| Alport syndrome, mental retardation, midface hypoplasia and elliptocytosis chromosomal region gene 1 homolog (human) | BM235514 | 0.405 | 0.006 | 0.009 |
| Diaphanous homolog 3 (Drosophila) | NM_019670 | 0.405 | 0.01 | 0.037 |
| ESTs, Weakly similar to phosphatase (Caenorhabditis elegans) (C.elegans) | BG075843 | 0.405 | 0.003 | 0.03 |
| Follistatin | NM_008046 | 0.405 | 0.005 | 0.036 |
| inner centromere protein | BB418702 | 0.405 | 0.001 | 0.002 |
| ROD1 regulator of differentiation 1 (S. pombe) | BB519382 | 0.405 | 0.002 | 0.016 |
| Centromere protein N | BM230253 | 0.403 | 0.002 | 0.012 |
| IKAROS family zinc finger 1 | AV317621 | 0.403 | 0.002 | 0.004 |
| Leukocyte specific transcript 1 | U72644 | 0.403 | 0.002 | 0.0001 |
| Transcribed locus | BM116703 | 0.403 | 0.012 | 0.027 |
| Membrane-spanning 4-domains, subfamily A, member 8A | NM_022430 | 0.4 | 0.01 | 0.025 |
| Budding uninhibited by benzimidazoles 1 homolog, beta (S. cerevisiae) | AU045529 | 0.398 | 0.003 | 0.014 |
| Transcribed locus | BG061923 | 0.397 | 0.003 | 0.006 |
| Colony stimulating factor 3 receptor (granulocyte) | NM_007782 | 0.395 | 0.002 | 0.004 |
| C-type lectin domain family 4, member d | NM_010819 | 0.395 | 0.001 | 0.007 |
| RIKEN cDNA E130016E03 gene | AW547464 | 0.395 | 0.022 | 0.032 |
| Schlafen 8 | BC024709 | 0.395 | 0.006 | 0.039 |
| RIKEN cDNA 4930428B01 gene | BB167877 | 0.394 | 0.008 | 0.013 |
| Transcribed locus, strongly similar to NP_033509.1 ubiquitously transcribed tetratricopeptide repeat gene, X chromosome [Mus | BB306686 | 0.394 | 0.014 | 0.014 |
| Zinc finger E-box binding homeobox 2 | NM_015753 | 0.394 | 0.001 | 0.003 |
| RIKEN cDNA 4831429J16 gene | BB702047 | 0.392 | 0.001 | 0.005 |
| Toll-like receptor 1 | AF316985 | 0.392 | 0.003 | 0.004 |
| Mannose receptor, C type 1 | NM_008625 | 0.391 | 0.0001 | 0.002 |
| WW domain containing adaptor with coiled-coil | BM240080 | 0.391 | 0.003 | 0.015 |
| Transcribed locus | BB460274 | 0.389 | 0.009 | 0.005 |
| Meteorin, glial cell differentiation regulator-like | BB544962 | 0.386 | 0.009 | 0.015 |
| T-box18 | AK012980 | 0.386 | 0.004 | 0.015 |
| Transcribed locus | BB236216 | 0.386 | 0.003 | 0.008 |
| ESTs | BE853428 | 0.385 | 0.006 | 0.004 |
| RIKEN cDNA 0610025L06 gene | AV010467 | 0.385 | 0.001 | 0.0001 |
| CD244 natural killer cell receptor 2B4 | NM_018729 | 0.382 | 0.007 | 0.005 |
| Ecotropic viral integration site 2a | AI122415 | 0.382 | 0.002 | 0.001 |

FIG. 28I

| | | | | |
|---|---|---|---|---|
| RNA binding motif protein 47 | BB400564 | 0.382 | 0.004 | 0.031 |
| CD5 antigen-like | NM_009690 | 0.379 | 0.005 | 0.003 |
| kit oncogene | X65997 | 0.379 | 0.005 | 0.048 |
| Dermatan sulfate epimerase | BM207218 | 0.377 | 0.002 | 0.002 |
| RIKEN cDNA 6720463M24 gene | AK020138 | 0.375 | 0.008 | 0.016 |
| ESTs | BB462614 | 0.372 | 0.009 | 0.036 |
| Transmembrane protein 176A | AU040201 | 0.372 | 0.003 | 0.008 |
| WNT1 inducible signaling pathway protein 2 | NM_016873 | 0.372 | 0.002 | 0.0001 |
| ESTs | AI785329 | 0.368 | 0.011 | 0.023 |
| Transcribed locus | BB455909 | 0.368 | 0.004 | 0.0001 |
| Membrane-spanning 4-domains, subfamily A, member 6D | NM_026835 | 0.366 | 0.001 | 0.002 |
| Signal-regulatory protein beta 1 | AI662854 | 0.365 | 0.001 | 0.0001 |
| Structural maintenance of chromosomes 2 | BI684556 | 0.365 | 0.007 | 0.0001 |
| Chemokine (C-C motif) receptor 5 | D83648 | 0.364 | 0.001 | 0.004 |
| Latent transforming growth factor beta binding protein 2 | NM_013589 | 0.364 | 0.002 | 0.001 |
| MARCKS-like 1 | NM_010807 | 0.362 | 0.002 | 0.031 |
| Transcribed locus | BB336138 | 0.362 | 0.006 | 0.01 |
| Transcribed locus | BM241342 | 0.361 | 0.003 | 0.021 |
| Vav 1 oncogene | NM_011691 | 0.361 | 0.004 | 0.001 |
| Zinc finger CCCH type containing 12D | BB508669 | 0.361 | 0.007 | 0.004 |
| Transcribed locus | BB468551 | 0.358 | 0.005 | 0.005 |
| ESTs | BM240056 | 0.357 | 0.012 | 0.001 |
| RIKEN cDNA 4930547N16 gene | BM205349 | 0.357 | 0.011 | 0.027 |
| Glucosaminyl (N-acetyl) transferase 1, core 2 | AK017462 | 0.356 | 0.003 | 0.0001 |
| ESTs | BB147698 | 0.351 | 0.006 | 0.001 |
| Chemokine (C-X-C motif) ligand 12 | BC006640 | 0.348 | 0.0001 | 0.01 |
| C-type lectin domain family 4, member n | AF240358 | 0.348 | 0.006 | 0.011 |
| Mus musculus, clone IMAGE:3492506, mRNA, partial cds | AW763751 | 0.345 | 0.004 | 0.01 |
| Transmembrane and coiled coil domains 1 | BB470329 | 0.342 | 0.014 | 0.029 |
| Fc receptor-like S, scavenger receptor | BC016551 | 0.341 | 0.001 | 0.0001 |
| Interferon induced transmembrane protein 6 | BB193024 | 0.341 | 0.003 | 0.003 |
| Interleukin 1 receptor, type I | NM_008362 | 0.34 | 0.001 | 0.0001 |
| RIKEN cDNA 8430436C05 gene | AU016566 | 0.339 | 0.004 | 0.005 |
| Similar to SIRP beta 1 cell surface protein | BB224524 | 0.338 | 0.002 | 0.005 |
| C-type lectin domain family 4, member a2 | BC006623 | 0.337 | 0.001 | 0.001 |
| Kinesin family member 20B | BB200034 | 0.337 | 0.004 | 0.0001 |
| hematological and neurological expressed sequence 1 | AV067695 | 0.336 | 0.0001 | 0.04 |
| ribonuclease L (2, 5-oligoisoadenylate synthetase-dependent) | BF714880 | 0.333 | 0.002 | 0.002 |
| Serine/threonine kinase 17b (apoptosis-inducing) | AI661948 | 0.333 | 0.007 | 0.012 |
| Immunoglobulin superfamily, member 6 | NM_030691 | 0.33 | 0.002 | 0.001 |
| ESTs | AW909042 | 0.329 | 0.009 | 0.004 |
| Allograft inflammatory factor 1 | NM_019467 | 0.325 | 0.001 | 0.004 |
| Transcribed locus | BM239436 | 0.325 | 0.008 | 0.009 |
| Insulin-like growth factor binding protein 5 | NM_010518 | 0.324 | 0.001 | 0.0001 |
| CD163 antigen | NM_053094 | 0.323 | 0.001 | 0.034 |
| Potassium intermediate/small conductance calcium-activated channel, subfamily N, member 4 | BG865910 | 0.321 | 0.001 | 0.012 |
| G-protein coupled receptor 65 | NM_008152 | 0.316 | 0.003 | 0.0001 |
| Mus musculus growth arrest specific 1 (Gas1), mRNA | BB550400 | 0.312 | 0.0001 | 0.005 |
| Chemokine (C-C motif) ligand 12 | U50712 | 0.307 | 0.003 | 0.013 |

FIG. 28J

| | | | | |
|---|---|---|---|---|
| ESTs | BB488200 | 0.306 | 0.003 | 0.006 |
| C-type lectin domain family 4, member e | NM_019948 | 0.304 | 0.004 | 0.011 |
| Pro-platelet basic protein | NM_023785 | 0.303 | 0.003 | 0.004 |
| Epstein-Barr virus induced gene 2 | BM242490 | 0.301 | 0.003 | 0.003 |
| Chemokine (C-C motif) receptor 2 | BB148128 | 0.299 | 0.001 | 0.001 |
| TBC1 domain family, member 9 | BE853276 | 0.294 | 0.008 | 0.037 |
| Membrane-spanning 4-domains, subfamily A, member 4C | NM_029499 | 0.293 | 0.002 | 0.003 |
| Placenta-specific 8 | AF263458 | 0.289 | 0.001 | 0.003 |
| Transcribed locus | BB183534 | 0.284 | 0.003 | 0.001 |
| ESTs | BB040443 | 0.281 | 0.002 | 0.009 |
| Protein kinase, cAMP dependent regulatory, type II beta | BB216074 | 0.275 | 0.005 | 0.023 |
| Transcribed locus | BE632903 | 0.275 | 0.008 | 0.022 |
| RIKEN cDNA 2900062L11 gene | AK013740 | 0.273 | 0.012 | 0.034 |
| S100 calcium binding protein A8 (calgranulin A) | NM_013650 | 0.261 | 0.001 | 0.001 |
| Collagen and calcium binding EGF domains 1 | BB197647 | 0.258 | 0.007 | 0.002 |
| Cytochrome P450, family 1, subfamily b, polypeptide 1 | BI251808 | 0.253 | 0.002 | 0.003 |
| Chemokine (C-C motif) ligand 8 | NM_021443 | 0.222 | 0.001 | 0.029 |
| Transcribed locus | BB205102 | 0.206 | 0.01 | 0.01 |
| Formyl peptide receptor 2 | NM_008039 | 0.198 | 0.005 | 0.0001 |
| Matrix metallopeptidase 9 | NM_013599 | 0.198 | 0.004 | 0.001 |
| S100 calcium binding protein A9 (calgranulin B) | NM_009114 | 0.195 | 0.001 | 0.001 |
| Schlafen 4 | AF099975 | 0.195 | 0.002 | 0.001 |
| Mus musculus membrane-spanning 4-domains, subfamily A, member 9 (Ms4a9), mRNA. | NM_022429 | 0.192 | 0.002 | 0.001 |
| DEXH (Asp-Glu-X-His) box polypeptide 58 | AF316999 | 0.189 | 0.013 | 0.045 |
| hypothetical protein LOC215866 | BC002257 | 0.173 | 0.004 | 0.026 |
| Chemokine (C-X-C motif) ligand 5 | NM_009141 | 0.128 | 0.003 | 0.01 |
| Secreted frizzled-related protein 2 | NM_009144 | 0.128 | 0.001 | 0.0001 |
| ESTs | BB160675 | 0.083 | 0.047 | 0.04 |
| ESTs | AU019852 | 0.074 | 0.017 | 0.0001 |
| Cell adhesion molecule with homology to L1CAM | NM_007697 | 0.073 | 0.023 | 0.002 |
| Transient receptor potential cation channel, subfamily M, member 3 | BB377721 | 0.059 | 0.032 | 0.001 |
| Membrane-spanning 4-domains, subfamily A, member 4B | BB199001 | 0.051 | 0.033 | 0.026 |

FIG. 29A

Table 2: Differentially expressed genes at day 7 of nitrite therapy

| Gene Name | Accession # | ratio | SEM | P Value |
|---|---|---|---|---|
| Matrix metallopeptidase 13 | NM_008607 | 47.04 | 0.064 | 0.047 |
| Secreted frizzled-related protein 2 | NM_009144 | 16.54 | 0.034 | 0.033 |
| Chemokine (C-C motif) ligand 8 | NM_021443 | 12.03 | 0.012 | 0.032 |
| RIKEN cDNA 1500015O10 gene | BB426248 | 10.41 | 0.026 | 0.024 |
| Complement component 2 (within H-2S) | NM_013484 | 8.98 | 0.046 | 0.005 |
| Paired related homeobox 2 | AK019971 | 8.9 | 0.064 | 0.049 |
| Matrix metallopeptidase 3 | NM_010809 | 7.88 | 0.032 | 0.031 |
| Adiponectin, C1Q and collagen domain containing | NM_009605 | 7.84 | 0.003 | 0.017 |
| Collagen triple helix repeat containing 1 | AK003674 | 7.82 | 0.007 | 0.045 |
| CDNA sequence AB124611 | BM246462 | 7.3 | 0.037 | 0.043 |
| Lymphocyte cytosolic protein 2 | BC006948 | 6.28 | 0.038 | 0.041 |
| Proteoglycan 4 (megakaryocyte stimulating factor, articular superficial zone protein) | NM_021400 | 5.96 | 0.003 | 0.023 |
| Perilipin | BB144871 | 5.71 | 0.021 | 0.036 |
| Chondroadherin | NM_007689 | 5.62 | 0.008 | 0.021 |
| ESTs | BG067883 | 5.49 | 0.057 | 0.003 |
| expressed sequence AW743884 | BB114398 | 5.45 | 0.007 | 0.045 |
| Phosphoenolpyruvate carboxykinase 1, cytosolic | AW106963 | 5.29 | 0.023 | 0.025 |
| Sushi-repeat-containing protein, X-linked 2 | BC028307 | 5.23 | 0.01 | 0.049 |
| Protein tyrosine phosphatase, receptor type, O | NM_011216 | 5.12 | 0.017 | 0.021 |
| CD52 antigen | NM_013706 | 5.08 | 0.006 | 0.045 |
| PYD and CARD domain containing | BG084230 | 4.97 | 0.013 | 0.048 |
| expressed sequence AI323359 | AI323359 | 4.84 | 0.004 | 0.046 |
| Twist gene homolog 1 (Drosophila) | NM_011658 | 4.77 | 0.044 | 0.04 |
| Protein tyrosine phosphatase, receptor type, F | BF235516 | 4.76 | 0.015 | 0.038 |
| Transcribed locus | AV223337 | 4.64 | 0.031 | 0.008 |
| Integrin, beta-like 1 | BC020152 | 4.54 | 0.004 | 0.003 |
| Thrombospondin 1 | AI385532 | 4.44 | 0.002 | 0.038 |
| Collagen, type XI, alpha 1 | NM_007729 | 4.43 | 0.011 | 0.018 |
| Coiled-coil domain containing 80 | BG074158 | 4.38 | 0.007 | 0.011 |
| Complement component 4B (Childo blood group) | NM_009780 | 4.34 | 0.005 | 0.026 |
| Angiopoietin-like 7 | BC023373 | 4.27 | 0.005 | 0.035 |
| Solute carrier family 41, member 2 | BC026874 | 4.24 | 0.026 | 0.018 |
| Fatty acid desaturase 3 | BE652876 | 4.24 | 0.02 | 0.025 |
| Terf1 (TRF1)-interacting nuclear factor 2 | BM238063 | 4.19 | 0.039 | 0.018 |
| Transcribed locus | AK012530 | 4.05 | 0.024 | 0.006 |
| Cell death-inducing DFFA-like effector c | BB221402 | 3.99 | 0.02 | 0.01 |
| Alport syndrome, mental retardation, midface hypoplasia and elliptocytosis chromosomal region gene 1 homolog (human) | BM235514 | 3.95 | 0.034 | 0.046 |
| Stearoyl-Coenzyme A desaturase 1 | NM_009127 | 3.94 | 0.001 | 0.049 |
| Parathyroid hormone receptor 1 | BC013446 | 3.89 | 0.024 | 0.033 |
| Transcribed locus | BB631473 | 3.8 | 0.031 | 0.011 |
| Transcribed locus | AV341509 | 3.8 | 0.027 | 0.013 |
| fibromodulin | AV290700 | 3.76 | 0.003 | 0.009 |
| 3-phosphoglycerate dehydrogenase | AA561726 | 3.68 | 0.011 | 0.027 |

FIG. 29B

| | | | | |
|---|---|---|---|---|
| Transcribed locus | BB549310 | 3.64 | 0.022 | 0.041 |
| Leukocyte-associated Ig-like receptor 1 | AK017222 | 3.64 | 0.021 | 0.04 |
| Tenomodulin | AF291655 | 3.63 | 0.001 | 0.03 |
| Matrix metallopeptidase 14 (membrane-inserted) | NM_008608 | 3.53 | 0.001 | 0.05 |
| Fibulin 1 | NM_010180 | 3.43 | 0.014 | 0.038 |
| Nuclear receptor binding protein 2 | BC012437 | 3.42 | 0.008 | 0.023 |
| Interferon, alpha-inducible protein 27 | AY090098 | 3.32 | 0.002 | 0.005 |
| Tumor necrosis factor, alpha-induced protein 8 | NM_134131 | 3.31 | 0.009 | 0.044 |
| Transcribed locus | BB164127 | 3.28 | 0.019 | 0.049 |
| Protein kinase, cAMP dependent regulatory, type II beta | BB216074 | 3.28 | 0.015 | 0.021 |
| phosphatidylethanolamine binding protein 1 | AK008037 | 3.28 | 0.03 | 0.049 |
| RIKEN cDNA 1200002N14 gene | BC021433 | 3.27 | 0.006 | 0.043 |
| KDEL (Lys-Asp-Glu-Leu) endoplasmic reticulum protein retention receptor 3 | NM_134090 | 3.25 | 0.005 | 0.046 |
| LIM domain and actin binding 1 | C81400 | 3.14 | 0.004 | 0.027 |
| Fatty acid desaturase 2 | NM_019699 | 3.12 | 0.016 | 0.022 |
| Chemokine (C-X-C motif) ligand 9 | NM_008599 | 3.11 | 0.008 | 0.017 |
| G-protein signalling modulator 2 (AGS3-like, C. elegans) | BC021308 | 3.1 | 0.01 | 0.044 |
| RIKEN cDNA E130112L23 gene | BI412259 | 3.08 | 0.013 | 0.009 |
| Nicotinamide N-methyltransferase | AK006371 | 3.08 | 0.005 | 0.038 |
| Leucine-rich repeat kinase 1 | BC027199 | 3.08 | 0.007 | 0.035 |
| Prostaglandin I2 (prostacyclin) synthase | NM_008968 | 3.06 | 0.005 | 0.001 |
| Receptor (TNFRSF)-interacting serine-threonine kinase 1 | AA186144 | 3.05 | 0.009 | 0.039 |
| Interferon regulatory factor 7 | NM_016850 | 3.05 | 0.005 | 0.022 |
| Transferrin | AF440692 | 3.04 | 0.003 | 0.028 |
| RIKEN cDNA 2610528G05 gene | BB530515 | 3.02 | 0.003 | 0.025 |
| Transcribed locus | BB420529 | 3.01 | 0.018 | 0.042 |
| Ras association (RalGDS/AF-6) domain family member 2 | AK018504 | 2.99 | 0.013 | 0.042 |
| ESTs | AU067733 | 2.97 | 0.026 | 0.027 |
| Adenomatosis polyposis coli down-regulated 1 | BB770932 | 2.96 | 0.015 | 0.005 |
| Interleukin 2 receptor, gamma chain | L20048 | 2.95 | 0.005 | 0.039 |
| DCN1, defective in cullin neddylation 1, domain containing 5 (S. cerevisiae) | BE824946 | 2.92 | 0.027 | 0.014 |
| Myosin IXb | NM_015742 | 2.91 | 0.006 | 0.031 |
| Collagen, type I, alpha 2 | BF227507 | 2.91 | 0.0001 | 0.031 |
| Connective tissue growth factor | NM_010217 | 2.89 | 0.001 | 0.03 |
| Solute carrier family 39 (metal ion transporter), member 6 | BB825002 | 2.86 | 0.005 | 0.036 |
| RIKEN cDNA 9030425E11 gene | BG072972 | 2.84 | 0.006 | 0.033 |
| Adenosine monophosphate deaminase 2 (isoform L) | AV330806 | 2.84 | 0.009 | 0.043 |
| tropomyosin 3, gamma | AV311925 | 2.81 | 0.008 | 0.037 |
| Ring finger protein 26 | BC004739 | 2.8 | 0.011 | 0.018 |
| RIKEN cDNA 2610002J02 gene | AV218922 | 2.8 | 0.01 | 0.032 |
| Collagen, type XXIII, alpha 1 | AI429655 | 2.79 | 0.014 | 0.036 |
| Biglycan | BC019502 | 2.76 | 0.0001 | 0.049 |
| Ceramide kinase | BI905090 | 2.75 | 0.009 | 0.044 |
| ATPase, class V, type 10A | BM249532 | 2.75 | 0.025 | 0.02 |

FIG. 29C

| | | | | |
|---|---|---|---|---|
| Myosin IE | AK018649 | 2.74 | 0.007 | 0.038 |
| Ring finger protein 135 | AK010429 | 2.67 | 0.012 | 0.026 |
| RIKEN cDNA 3321401G04 gene | BF228051 | 2.67 | 0.017 | 0.033 |
| ESTs | BM220188 | 2.67 | 0.033 | 0.046 |
| ABI gene family, member 3 (NESH) binding protein | BC026627 | 2.67 | 0.003 | 0.03 |
| Serine (or cysteine) peptidase inhibitor, clade B, member 1a | AF426024 | 2.66 | 0.002 | 0.048 |
| Microtubule associated monoxygenase, calponin and LIM domain containing 1 | NM_138315 | 2.65 | 0.012 | 0.032 |
| Caspase 4, apoptosis-related cysteine peptidase | NM_007609 | 2.65 | 0.014 | 0.033 |
| Transcribed locus | BM951910 | 2.64 | 0.01 | 0.028 |
| SPC24, NDC80 kinetochore complex component, homolog (S. cerevisiae) | BF577722 | 2.63 | 0.021 | 0.028 |
| Transcribed locus | AI461392 | 2.62 | 0.015 | 0.01 |
| Transcribed locus | BF662057 | 2.61 | 0.008 | 0.047 |
| Matrix metallopeptidase 2 | BF147716 | 2.61 | 0.001 | 0.04 |
| Guanine nucleotide binding protein (G protein), alpha inhibiting 1 | BQ174580 | 2.61 | 0.007 | 0.0001 |
| Solute carrier family 1 (neutral amino acid transporter), member 5 | NM_009201 | 2.6 | 0.003 | 0.03 |
| G-protein signalling modulator 1 (AGS3-like, C. elegans) | BC026486 | 2.59 | 0.018 | 0.042 |
| Serine (or cysteine) peptidase inhibitor, clade F, member 1 | NM_011340 | 2.58 | 0.0001 | 0.026 |
| ESTs | BB017018 | 2.58 | 0.019 | 0.002 |
| Forkhead box P1 | BG962849 | 2.57 | 0.012 | 0.049 |
| CD163 antigen | NM_053094 | 2.57 | 0.006 | 0.008 |
| Cardiotrophin-like cytokine factor 1 | BB825816 | 2.57 | 0.033 | 0.031 |
| Frizzled homolog 2 (Drosophila) | BB371406 | 2.56 | 0.008 | 0.043 |
| RIKEN cDNA 1110018H23 gene | AK003777 | 2.55 | 0.011 | 0.04 |
| Endothelin receptor type A | AW558570 | 2.55 | 0.01 | 0.04 |
| Amine oxidase, copper containing 3 | NM_009675 | 2.52 | 0.004 | 0.042 |
| Immunoglobulin superfamily, member 8 | AF411055 | 2.51 | 0.005 | 0.028 |
| Granulin | AV166504 | 2.5 | 0.0001 | 0.045 |
| S-phase kinase-associated protein 2 (p45) | AV259620 | 2.49 | 0.017 | 0.01 |
| Mitochondrial ribosomal protein S6 | BM729431 | 2.49 | 0.004 | 0.005 |
| Kruppel-like factor 16 | NM_078477 | 2.48 | 0.013 | 0.013 |
| Tubulin, beta 5 | BG064086 | 2.47 | 0.003 | 0.05 |
| ESTs | AW553802 | 2.47 | 0.017 | 0.044 |
| Prickle-like 2 (Drosophila) | BQ177191 | 2.45 | 0.01 | 0.007 |
| MAM domain containing 2 | AK004794 | 2.45 | 0.006 | 0.038 |
| Septin 5 | AF033350 | 2.44 | 0.007 | 0.024 |
| Transcribed locus | BB275943 | 2.43 | 0.002 | 0.021 |
| Cell division cycle associated 4 | AF322238 | 2.43 | 0.006 | 0.033 |
| Echinoderm microtubule associated protein like 5 | BB650819 | 2.42 | 0.022 | 0.045 |
| Procollagen C-endopeptidase enhancer protein | BB250811 | 2.41 | 0.0001 | 0.039 |
| CDNA sequence BC023892 | BE687858 | 2.41 | 0.005 | 0.034 |
| Wnt inhibitory factor 1 | BC004048 | 2.4 | 0.022 | 0.009 |
| Transmembrane protein 206 | NM_025864 | 2.4 | 0.02 | 0.028 |
| Keratocan | NM_008438 | 2.39 | 0.004 | 0.019 |
| Neurobeachin like 1 | BB022773 | 2.38 | 0.015 | 0.024 |

FIG. 29D

| | | | | |
|---|---|---|---|---|
| Interferon activated gene 204 | NM_008329 | 2.38 | 0.015 | 0.037 |
| S100 calcium binding protein A10 (calpactin) | AV295650 | 2.37 | 0.001 | 0.033 |
| Protein phosphatase 1H (PP2C domain containing) | AU040848 | 2.37 | 0.01 | 0.037 |
| Solute carrier family 25 (mitochondrial carrier, adenine nucleotide translocator), member 5 | C81442 | 2.36 | 0.002 | 0.05 |
| Myelin basic protein expression factor 2, repressor | U13262 | 2.36 | 0.017 | 0.006 |
| Transcribed locus | BG061923 | 2.35 | 0.011 | 0.026 |
| SH3 domain protein D19 | NM_012059 | 2.34 | 0.002 | 0.049 |
| Follistatin | NM_008046 | 2.33 | 0.007 | 0.024 |
| Guanidinoacetate methyltransferase | AF015887 | 2.32 | 0.001 | 0.037 |
| ESTs | AI987844 | 2.31 | 0.011 | 0.022 |
| Signal peptide, CUB domain, EGF-like 2 | BI133839 | 2.3 | 0.005 | 0.013 |
| ESTs | BB361398 | 2.3 | 0.016 | 0.026 |
| Transcribed locus | BM241342 | 2.27 | 0.011 | 0.024 |
| Chordin-like 1 | AV144145 | 2.27 | 0.013 | 0.021 |
| Myosin, heavy polypeptide 9, non-muscle | NM_022410 | 2.25 | 0.002 | 0.044 |
| Transcribed locus, strongly similar to NP_001019474.1 Lix1 homolog (mouse)-like [Rattus norvegicus] | BM502719 | 2.24 | 0.003 | 0.05 |
| Transcribed locus | AV352768 | 2.24 | 0.018 | 0.035 |
| Ubiquitin specific peptidase 7 | BM247366 | 2.23 | 0.006 | 0.006 |
| Transcribed locus | BB218653 | 2.23 | 0.01 | 0.034 |
| RIKEN cDNA 4933407H18 gene | BB476293 | 2.23 | 0.004 | 0.005 |
| Transmembrane protein 120A | AV069499 | 2.22 | 0.007 | 0.025 |
| Transcribed locus | BM234702 | 2.22 | 0.012 | 0.034 |
| SEC14 and spectrin domains 1 | AV276619 | 2.22 | 0.005 | 0.011 |
| Ubiquitin associated protein 2-like | AA833196 | 2.2 | 0.033 | 0.001 |
| Transcribed locus | BQ033755 | 2.2 | 0.015 | 0.049 |
| Integrin beta 3 | AV352983 | 2.19 | 0.02 | 0.042 |
| Growth differentiation factor 10 | L42114 | 2.19 | 0.005 | 0.004 |
| Transcribed locus | AV235415 | 2.18 | 0.014 | 0.02 |
| Tissue factor pathway inhibitor | AF004833 | 2.18 | 0.006 | 0.039 |
| Ring finger protein 215 | C77903 | 2.18 | 0.006 | 0.032 |
| Rho GTPase activating protein 18 | BB667215 | 2.18 | 0.005 | 0.02 |
| Neurotrophic tyrosine kinase, receptor, type 2 | AK018789 | 2.17 | 0.006 | 0.007 |
| Coiled-coil domain containing 102A | BB375402 | 2.17 | 0.012 | 0.049 |
| Ankyrin repeat domain 29 | AV370837 | 2.17 | 0.014 | 0.034 |
| Zinc finger, CCHC domain containing 11 | BG060248 | 2.16 | 0.017 | 0.014 |
| Transcribed locus | AK017223 | 2.16 | 0.015 | 0.011 |
| Pleckstrin homology domain containing, family O member 1 | NM_023320 | 2.16 | 0.002 | 0.034 |
| Glycoprotein m6b | AF254879 | 2.16 | 0.004 | 0.038 |
| Transcribed locus | BM243944 | 2.15 | 0.016 | 0.029 |
| Transcribed locus | BM239436 | 2.14 | 0.025 | 0.026 |
| Ring finger protein 213 | AW556558 | 2.14 | 0.001 | 0.022 |
| RIKEN cDNA 4933439C10 gene | AV205521 | 2.14 | 0.012 | 0.038 |
| ESTs, Weakly similar to RIKEN cDNA 5730493B19 (Mus musculus) (M.musculus) | AU040379 | 2.14 | 0.012 | 0.005 |
| ATPase, Ca++ transporting, cardiac muscle, slow twitch 2 | BG063183 | 2.14 | 0.015 | 0.022 |

FIG. 29E

| | | | | |
|---|---|---|---|---|
| TYRO3 protein tyrosine kinase 3 | AB000828 | 2.13 | 0.034 | 0.029 |
| RIKEN cDNA 1110034A24 gene | BB815668 | 2.13 | 0.015 | 0.009 |
| Transmembrane protein 68 | BC016240 | 2.12 | 0.006 | 0.016 |
| Sema domain, immunoglobulin domain (Ig), short basic domain, secreted, (semaphorin) 3B | NM_009153 | 2.12 | 0.007 | 0.038 |
| Protein kinase N1 | AI463328 | 2.12 | 0.007 | 0.045 |
| Insulin-like growth factor binding protein 4 | BB787243 | 2.12 | 0.0001 | 0.019 |
| expressed sequence AA407331 | AA407331 | 2.12 | 0.014 | 0.038 |
| RNA binding motif protein 43 | BC003333 | 2.11 | 0.009 | 0.047 |
| expressed sequence AI197429 | BI082172 | 2.11 | 0.013 | 0.04 |
| CDNA sequence BC067047 | BB794978 | 2.11 | 0.003 | 0.011 |
| BTB and CNC homology 2 | BB529913 | 2.11 | 0.013 | 0.04 |
| Kelch domain containing 5 | BB795533 | 2.1 | 0.009 | 0.026 |
| Carbohydrate (N-acetylgalactosamine 4-0) sulfotransferase 14 | AK011230 | 2.1 | 0.004 | 0.019 |
| Rho GTPase activating protein 4 | NM_138630 | 2.09 | 0.018 | 0.027 |
| Phosphodiesterase 3B, cGMP-inhibited | AV270888 | 2.09 | 0.004 | 0.024 |
| NLR family, CARD domain containing 5 | AV277444 | 2.09 | 0.01 | 0.031 |
| La ribonucleoprotein domain family, member 6 | NM_026235 | 2.09 | 0.014 | 0.01 |
| Zinc finger with KRAB and SCAN domains 3 | BQ084812 | 2.07 | 0.006 | 0.031 |
| ESTs | BB115513 | 2.07 | 0.016 | 0.031 |
| ESTs | BB541054 | 2.07 | 0.016 | 0.049 |
| Transcribed locus | AV230978 | 2.06 | 0.015 | 0.025 |
| HpaII tiny fragments locus 9c | NM_008307 | 2.06 | 0.009 | 0.033 |
| ESTs | BB162048 | 2.06 | 0.016 | 0.015 |
| Transcribed locus | BB414446 | 2.05 | 0.002 | 0.023 |
| Interleukin 6 signal transducer | BI102913 | 2.05 | 0.002 | 0.008 |
| 3-ketodihydrosphingosine reductase | AK018155 | 2.05 | 0.005 | 0.048 |
| Transcribed locus | BB034265 | 2.04 | 0.004 | 0.049 |
| Transcribed locus | AK017680 | 2.04 | 0.006 | 0.017 |
| Single-stranded DNA binding protein 2 | AK005150 | 2.04 | 0.015 | 0.012 |
| Signal transducer and activator of transcription 1 | AW214029 | 2.04 | 0.006 | 0.042 |
| Ras-related associated with diabetes | NM_019662 | 2.04 | 0.005 | 0.042 |
| Nischarin | BB025231 | 2.04 | 0.003 | 0.019 |
| Lysophosphatidic acid receptor 1 | U70622 | 2.04 | 0.003 | 0.019 |
| Diacylglycerol kinase, eta | AV276089 | 2.03 | 0.011 | 0.036 |
| Transcribed locus | AV340292 | 2.02 | 0.025 | 0.0001 |
| Transcribed locus | AV272196 | 2.02 | 0.013 | 0.04 |
| Poly (ADP-ribose) polymerase family, member 14 | BC021340 | 2.02 | 0.004 | 0.009 |
| Histocompatibility 2, T region locus 23 | NM_010398 | 2.02 | 0.001 | 0.017 |
| Frequenin homolog (Drosophila) | BE990928 | 2.02 | 0.003 | 0.045 |
| Dedicator of cytokinesis 8 | NM_028785 | 2.02 | 0.006 | 0.043 |
| Cyclin D1 | NM_007631 | 2.02 | 0.002 | 0.032 |
| Tia1 cytotoxic granule-associated RNA binding protein-like 1 | BM122619 | 2.01 | 0.003 | 0.022 |
| matrilin 2 | BB338441 | 2.01 | 0.006 | 0.025 |
| Epidermal growth factor receptor pathway substrate 8 | NM_007945 | 2 | 0.003 | 0.044 |
| Inhibitor of Bruton agammaglobulinemia tyrosine kinase | BM250711 | 0.5 | 0.002 | 0.037 |
| Transcribed locus | AW546142 | 0.498 | 0.003 | 0.018 |

FIG. 29F

| | | | | |
|---|---|---|---|---|
| Transcribed locus | AV236736 | 0.498 | 0.01 | 0.002 |
| progestin and adipoQ receptor family member III | AK018174 | 0.498 | 0.01 | 0.021 |
| Kelch domain containing 6 | AK014702 | 0.495 | 0.011 | 0.011 |
| Xenotropic and polytropic retrovirus receptor 1 | AV337591 | 0.493 | 0.002 | 0.047 |
| Potassium voltage gated channel, Shab-related subfamily, member 1 | BB324482 | 0.488 | 0.002 | 0.016 |
| Myosin, heavy polypeptide 1, skeletal muscle, adult | AJ002522 | 0.488 | 0.001 | 0.044 |
| RIKEN cDNA 1190003M12 gene | AK004474 | 0.485 | 0.006 | 0.022 |
| Ariadne ubiquitin-conjugating enzyme E2 binding protein homolog 1 (Drosophila) | BB354785 | 0.485 | 0.004 | 0.047 |
| Fas (TNF receptor superfamily member 6) | BG976607 | 0.483 | 0.001 | 0.001 |
| Glutamic pyruvate transaminase (alanine aminotransferase) 2 | BG069993 | 0.481 | 0.0001 | 0.025 |
| Transcribed locus | AK018397 | 0.472 | 0.004 | 0.031 |
| ESTs, Weakly similar to ZF90 MOUSE ZINC FINGER PROTEIN 90 (M.musculus) | C76431 | 0.472 | 0.016 | 0.008 |
| Transcribed locus | BB081359 | 0.469 | 0.007 | 0.005 |
| Gene model 967, (NCBI) | AW457804 | 0.469 | 0.007 | 0.012 |
| Patatin-like phospholipase domain containing 8 | BB076314 | 0.467 | 0.003 | 0.012 |
| Zinc finger protein 644 | AU015726 | 0.465 | 0.009 | 0.025 |
| Insulin-like growth factor 2 mRNA binding protein 3 | BG092043 | 0.461 | 0.002 | 0.032 |
| Solute carrier family 7 (cationic amino acid transporter, y+ system), member 2 | BF533509 | 0.455 | 0.01 | 0.018 |
| AF4/FMR2 family, member 1 | BB586268 | 0.455 | 0.008 | 0.034 |
| Transcribed locus | C79043 | 0.452 | 0.002 | 0.006 |
| Kinesin family member 21A | BB342219 | 0.45 | 0.002 | 0.044 |
| Glycerol-3-phosphate dehydrogenase 1 (soluble) | BC019391 | 0.45 | 0.0001 | 0.041 |
| UEV and lactate/malate dehyrogenase domains | NM_016855 | 0.441 | 0.006 | 0.001 |
| G protein-coupled receptor 137C | BQ175524 | 0.433 | 0.008 | 0.001 |
| D-aspartate oxidase | BC006690 | 0.433 | 0.001 | 0.03 |
| Adenylate kinase 1 | BE373450 | 0.431 | 0.007 | 0.037 |
| ESTs | BB165757 | 0.418 | 0.009 | 0.025 |
| Minichromosome maintenance complex component 9 | AV312905 | 0.413 | 0.005 | 0.021 |
| ESTs, Moderately similar to I49130 reverse transcriptase - mouse (M.musculus) | BB080140 | 0.412 | 0.007 | 0.031 |
| Sortilin-related receptor, LDLR class A repeats-containing | BI648081 | 0.391 | 0.004 | 0.015 |
| RIKEN cDNA 3222402P14 gene | BB283973 | 0.391 | 0.0001 | 0.023 |
| Protein kinase, cAMP dependent regulatory, type II alpha | AV112640 | 0.366 | 0.001 | 0.028 |
| Pregnancy-specific glycoprotein 28 | AF113598 | 0.36 | 0.004 | 0.006 |
| Cytochrome P450, family 4, subfamily x, polypeptide 1 | BB171122 | 0.358 | 0.017 | 0.029 |
| Nicotinamide phosphoribosyltransferase | AW989410 | 0.357 | 0.002 | 0.042 |
| Melanin-concentrating hormone receptor 1 | BE647763 | 0.35 | 0.008 | 0.014 |
| TEA domain family member 1 | BB546942 | 0.347 | 0.009 | 0.017 |
| ESTs | BB821700 | 0.344 | 0.01 | 0.009 |
| Murine (DBA2) mRNA fragment for gag related peptide | BB662083 | 0.339 | 0.002 | 0.027 |
| Aquaporin 4 | AW489155 | 0.336 | 0.004 | 0.03 |
| Transmembrane protein 106B | AK018015 | 0.333 | 0.013 | 0.042 |
| Solute carrier family 38, member 4 | AK003626 | 0.321 | 0.0001 | 0.048 |

FIG. 29G

| Description | Accession | | | |
|---|---|---|---|---|
| Transcribed locus, strongly similar to NP_062686.1 ring-box 1 [Mus musculus] | AV038578 | 0.299 | 0.003 | 0.025 |
| Calcium/calmodulin-dependent protein kinase II alpha | X14836 | 0.292 | 0.002 | 0.015 |
| Hypothetical protein LOC100042207 | AK017182 | 0.28 | 0.005 | 0.016 |
| Transmembrane 7 superfamily member 3 | AV114231 | 0.27 | 0.012 | 0.005 |
| EST X83313 | BG065719 | 0.253 | 0.005 | 0.042 |
| Transcribed locus | AV268386 | 0.216 | 0.007 | 0.019 |
| ESTs, Moderately similar to YO11 MOUSE HYPOTHETICAL PROTEIN ORF-1137 (M.musculus) | AV309800 | 0.211 | 0.002 | 0.007 |
| Tubulin tyrosine ligase-like family, member 7 | AK014905 | 0.19 | 0.008 | 0.03 |
| ESTs, Weakly similar to JAK3 MOUSE TYROSINE-PROTEIN KINASE JAK3 (M.musculus) | BG083989 | 0.109 | 0.002 | 0.021 |
| ESTs, Weakly similar to GNMSLL retrovirus-related reverse transcriptase homolog - mouse retrotransposon (M.musculus) | AI506532 | 0.087 | 0.002 | 0.021 |
| ESTs | BB099075 | 0.084 | 0.004 | 0.002 |

USE OF NITRITE SALTS IN TREATING TISSUE DAMAGE

CROSS-REFERENCE TO RELATED APPLICATIONS

This application is a divisional application of U.S. patent application Ser. No. 14/104,411, filed on Dec. 12, 2013, which is a continuation of U.S. patent application Ser. No. 13/378,530, filed on Jun. 5, 2012, which is a United States National Stage Application of International Application No. PCT/US2010/036269, filed on May 26, 2010, which claims benefit of the filing date of U.S. Provisional Patent Application No. 61/268,926, filed on Jun. 18, 2009, each of which is hereby incorporated by reference in their entirety.

FEDERALLY SPONSORED RESEARCH OR DEVELOPMENT

The work described below was supported by Grant No. HL80482, which was awarded by the National Institutes of Health. The Government has certain rights in the invention.

TECHNICAL FIELD

This invention relates to methods and compositions useful for treating tissue damage, and more particularly to treating tissue necrosis.

BACKGROUND

Multicellular organisms are made up of tissues, i.e., organized aggregates of specialized groups of cells of similar form and function. Animal tissues include connective tissue, muscle tissue, nervous tissue and epithelial tissue. Regardless of the kind of tissue, tissue damage, whether by infection, trauma, or disease, contributes significantly to human morbidity and mortality. There is a continuing need for therapeutic strategies that lead to successful treatment of damaged tissue.

SUMMARY

The present invention is based, in part, on our discovery of compositions and methods that can be used to treat tissue damage, including damage caused by cardiovascular disease, infection or trauma. Tissue damage generally occurs when some of the cells in a localized area given tissue become injured or die, so that the tissue itself looses part or all or its the ability to function. Severe tissue damage can result in tissue necrosis, i.e., the death of all or substantially all of the cells in a localized area. The tissue damage encompassed by the methods of the claims can stem from any a wide range of medical conditions that result in cellular injury or cell death, for example, disorders such as peripheral artery disease, type 1 or type 2 diabetes, atherosclerotic cardiovascular disease, intermittent claudication (which can manifest as cramping pain in the extremities due to inadequate blood supply), critical limb ischemic disease, stroke, myocardial infarction, inflammatory bowel disease, peripheral neuropathy, rheumatoid arthritis, lupus, bacterial infections, fungal infections, fasciitis, and cellulitis; traumatic injuries such as wounds, burns, lacerations, contusions, frostbite, envenomation, bone fractures, infections, or surgical procedures; congenital malformations such as hernias, cardiac defects and gastrointestinal defects. Thus, tissue damage can occur in a variety of tissue types including, for example, skeletal muscle, smooth muscle, cardiac muscle, neuronal tissue, skin, mesenchymal tissue, connective tissue, gastrointestinal tissue and bone.

Also contemplated are compositions and methods to stimulate tissue regeneration. The compositions and methods can be used to stimulate tissue regeneration following damage to a tissue or organ caused by such conditions as trauma, scarring, abnormal protein deposition, amyloidoses, ischemia or diabetes, infections, or surgical procedures; congenital malformations such as hernias, cardiac defects and gastrointestinal defects that result in damage to the tissue.

Also provided are compositions and methods to treat inflammatory diseases. The inflammatory diseases encompassed by the methods of this invention can stem from a wide range of medical conditions that cause inflammation. Inflammation refers to all phases of the process of inflammation, including the initial signaling events, antigen presentation, dendritic cell activation, antibody production, T-cell activation, B-cell activation and cytokine expression. One type of inflammatory disease which can be treated by the compositions and methods described herein are immunoinflammatory diseases. Examples of immunoinflammatory diseases include such conditions as rheumatoid arthritis, juvenile rheumatoid arthritis, osteoarthritis, transplant rejection, sepsis, acute respiratory distress syndrome, asthma, and cancer. Another type of inflammatory disease which can be treated by the composition and methods described herein are autoimmune diseases. Examples of autoimmune diseases include such conditions as multiple sclerosis, psoriasis, inflammatory bowel disease, glomerulonephritis, lupus, uveitis, and chronic hepatitis. Other inflammatory diseases can also be treated by the compositions and methods described in this invention, including such conditions caused by trauma, oxidative stress, cell death, irradiation damage, ischemia, reperfusion, cancer, transplant rejection, and viral infection.

Regardless of whether the methods are described with respect to a particular medical condition or tissue type, the methods can be carried out by administering to a subject (e.g., a human patient) in need of treatment a pharmaceutically acceptable composition comprising inorganic nitrite or a pharmaceutically acceptable salt thereof. The inorganic nitrite or a pharmaceutically acceptable salt thereof can be formulated in various ways and can include pharmaceutically acceptable carriers. For ease of reading, we will not repeat the phrase "or a pharmaceutically acceptable salt thereof" on every occasion. It is to be understood that where inorganic nitrite can be used, a pharmaceutically acceptable salt of the compound may also be used.

Accordingly, the invention features physiologically acceptable compositions of inorganic nitrite and methods by which the compositions can be administered to a patient diagnosed as having, for example, tissue damage. These methods can include the steps of a) identifying a subject (e.g., a human patient) who is experiencing or is likely to experience tissue damage; and b) providing to the subject a composition including inorganic nitrite for a time and in an amount sufficient to reduce the tissue damage. The nitrite can result in the differential expression of genes involved in tissue repair responses, e.g., pathways or genes involved in cardiovascular system development and function, tissue morphology, carbohydrate metabolism; skeletal muscle development, tissue development; cellular assembly and organization, angiogenesis and molecular transport with the resulting remodeling of the damaged tissue. Such remodeling can include for example, the growth of new blood vessels in the damaged tissue and proliferation of muscle cells.

Patients amenable to being treated with inorganic nitrite can also be treated with nitrate. We may use the terms "subject," "individual" and "patient" interchangeably. While the present methods are certainly intended for application to human patients, the invention is not so limited. Domesticated animals, including, for example cats, dogs, horses, cows and other domesticated animals can also be treated.

The pharmaceutically acceptable compositions of the invention include inorganic nitrite, e.g., a salt or ester of nitrous acid ($HNO_2$) or a pharmaceutically acceptable salt thereof. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred.

Suitable pharmaceutically acceptable salts can include, for example, sodium nitrite, potassium nitrite, or calcium nitrite. The invention is not so limited however and lists of exemplary salts are found in *Remington's Pharmaceutical Sciences,* 17th ed., Mack Publishing Company, Easton, Pa., 1985, p. 1418 and *Journal of Pharmaceutical Science,* 66, 2 (1977), each of which is incorporated herein by reference in its entirety. It will also be understood that certain nitrite compounds of the present invention may exist in solvated, for example hydrated, as well as unsolvated forms. Nitrite has the chemical formula $NO_2$ and may exist as an ion in water. Sodium nitrite has the chemical formula $NaNO_2$ and typically dissolves in water to form the sodium ion Na+ and the nitrite ion $NO_2$. It will further be understood that the present invention encompasses all such solvated forms of the nitrite compounds.

The inorganic nitrite is administered for a time and in an amount sufficient to result the reduction of tissue damage. The effect on tissue damage may be monitored indirectly, i.e., by monitoring a clinical endpoint. For example, the nitrite may be administered until a symptom of tissue damage, e.g., pain, swelling, skin discoloration, ulceration, neuropathy, or defective tissue wound healing, improves. The assessment of clinical benefit may entail comparison of the damaged tissue with the corresponding non-damaged tissue. Choice of specific clinical endpoints may depend, in part, upon the nature of the underlying medical condition, e.g., cessation or amelioration of intermittent claudication may be useful for patients with peripheral artery disease or diabetes; healing of skin ulcers may be useful for patients with defective wound healing, and relief from gastrointestinal pain, diarrhea and constipation may be useful for patient suffering from bowel ischemia, enhancement of protein expression through profiling of a patient's blood might be used to monitor therapeutic benefit in patients with amyloidosis or ischemia; enhancement of cardiac function may be useful for patients with damage to heart tissue; and reduction in scarring in post-surgical patients. Revascularization can be monitored directly, via imaging techniques such as contrast angiography, contrast pulse sequence (CPS) ultrasound imaging for high-resolution perfusion or detection of biomarkers. The course of treatment can also be monitored by assessing the levels of expression of particular genes or gene families associated with tissue regeneration, tissue remodeling, tissue morphology, cardiovascular function, carbohydrate metabolism, antigen presentation, cell or humoral mediated immunity, skeletal muscle development, cardiovascular development, tissue development, cellular assembly and organization, carbohydrate metabolism, molecular transport, neurological disease, cancer, nervous system development, cellular development and/or inflammatory disease.

In some embodiments, the nitrite may be administered until a symptom of inflammation improves. The assessment of clinical benefit may entail comparison of the inflamed tissue or joint with the corresponding non-inflamed tissue or joint or comparing the inflamed tissue, joint or organ to a normal tissue joint or organ. Cytokine profiles can also be generated from blood samples obtained from patients and analyzed for reduction of cytokine levels to those found in normal conditions. Choice of specific clinical endpoints may depend, in part, upon the nature of the underlying medical condition, e.g., inhibition of cytokine expression through profiling of a patients blood might be used to monitor therapeutic benefit in patients with sepsis or asthma; reduction of swelling and pain in joints may be useful for patients with arthritis; and relief from gastrointestinal pain, diarrhea and constipation may be useful for patient suffering from irritable bowel disease.

The amount of inorganic nitrite per dose can vary. For example, a subject can receive from about 0.05 µg/kg up to about 5000 µg/kg, e.g., about 0.05, 1, 5, 10, 25, 50, 100, 200, 250, 300, 400, 450, 500, 550, 600, 650, 700, 750, 800, 850, 900, 1000, 1250, 1500, 2000, 2500, 3000, 3500, 4000, 4500 or 5000 µg/kg. For example, a subject can receive up to or up to about 165 µg/kg, 16.5 µg/kg, or 8.25 µg/kg. Generally, we administer nitrite in an amount such that the circulating concentration does not exceed 1.0 µM (i.e., the nitrite is administered in a dose sufficient to produce a circulating concentration of nitrite in the subject that does not exceed 1.0 µM). For example, the nitrite can be administered in an amount such that the circulating concentration does not exceed 0.0005 µM, 0.001 µM, 0.002 µM, 0.003 µM, 0.004 µM, 0.005 µM, 0.01 µM, 0.02 µM, 0.03 µM, 0.04 µM, 0.05 µM, 0.1 µM, 0.15 µM, 0.2 µM, 0.25 µM, 0.3 µM, 0.35 µM, 0.4 µM, 0.45 µM, 0.5 µM, 0.55 µM, 0.6 µM, 0.65 µM, 0.7 µM, 0.75 µM, 0.8 µM, 0.85 µM, 0.9 µM, 0.95 µM, or 1.0 µM. Thus, exemplary dosages can produce a circulating concentration of nitrite in the subject of up to or up to about 0.03 µM, 0.003 µM, or 0.0015 µM.

The frequency of treatment may also vary. The subject can be treated one or more times per day (e.g., once, twice, three, four, five, or six times per day) or every so-many hours (e.g., about every 2, 4, 6, 8, 12, or 24 hours). The time course of treatment may be of varying duration, e.g., for two, three, four, five, six, seven, eight, nine, ten, fifteen, twenty, twenty five, thirty, thirty-five, forty, forty-five, fifty, fifty-five, sixty, sixty-five, seventy or more days. For example, the treatment can be twice a day for three days, twice a day for seven days, twice a day for ten days. Treatment cycles can be repeated at intervals, for example weekly, bimonthly or monthly, which are separated by periods in which no treatment is given. The treatment can be a single treatment or can last as long as the life span of the subject (e.g., many years).

The compositions can be administered to a subject in a variety of ways. For example, the compositions can be administered transdermally or injected (infused) intravenously, subcutaneously, sublingually, intracranially, intramuscularly, intraperitoneally, or intrapulmonarily. Oral formulations are also within the scope of the present invention. The treatment regime can vary depending upon various factors typically considered by one of ordinary skill in the art. These factors include the route of administration, the nature of the formulation, the nature of the patient's illness, the subject's size, weight, surface area, age, gender, other drugs being administered to the patient, and the judgment of the attending physician. The compositions can be administered along with or in addition to other treatments for tissue damage or, e.g., drug therapy, immunotherapy, or surgery (e.g., aspirin therapy, statin therapy, or antihypertensive therapy) or other treatments for the underlying cause of the tissue damage, e.g., antibiotics, antifungals.

Disorders amenable to the methods of the invention can include any disorder that presents with tissue damage. Conditions that present with tissue damage include, for example peripheral artery disease, diabetes, atherosclerotic cardiovascular disease, intermittent claudication, critical limb ischemic disease, defective wound healing, stroke, myocardial infarction, inflammatory bowel disease, a bone fracture, a bone infection, or peripheral neuropathy, avascular necrosis, rheumatoid arthritis, lupus, a bacterial infection, a fungal infection, fasciitis, or cellulitis, trauma, scarring, abnormal protein deposition, amyloidoses, or surgical procedures; congenital malformations such as hernias, cardiac defects and gastrointestinal defects.

Disorders amenable to the methods of the invention can include any disorder that presents with tissue necrosis or any disorder or condition that puts the patient at risk for tissue necrosis, for example peripheral artery disease, diabetes, atherosclerotic cardiovascular disease, intermittent claudication, critical limb ischemic disease, defective wound healing, stroke, myocardial infarction, inflammatory bowel disease, a bone fracture, a bone infection, or peripheral neuropathy, avascular necrosis, an autoimmune disease, a bacterial infection, a fungal infection, fasiculitis, or cellulitis.

Disorders amenable to the methods of the invention can include conditions that result in inflammation, for example, immunoinflammatory diseases such as rheumatoid arthritis, juvenile rheumatoid arthritis, osteoarthritis, transplant rejection, sepsis, acute respiratory distress syndrome, asthma, and cancer; autoimmune diseases, such as multiple sclerosis, psoriasis, inflammatory bowel disease, glomerulonephritis, lupus, uveitis, and chronic hepatitis, or inflammation resulting from trauma, oxidative stress, cell death, irradiation damage, ischemia, reperfusion, cancer, transplant rejection, and viral infection.

Accordingly, disclosed herein is a method of treating tissue damage in a subject, the method comprising: identifying a subject who has tissue damage; and administering to the subject a pharmaceutical composition comprising inorganic nitrite or a pharmaceutically acceptable salt thereof, wherein the nitrite is administered for a time and in an amount sufficient to reduce said tissue damage. The method can further include monitoring whether the subject experiences reduced tissue damage. The subject can be a mammal; the mammal can be human.

The pharmaceutically acceptable salt of inorganic nitrite is sodium nitrite, potassium nitrite, or calcium nitrite. The nitrite can be administered one or more times a day for example, for at least about two to about twenty days; for at least about two days; at least about three days; at least about four days; at least about five days; at least about six days; at least about seven days; at least about 10 days; or at least about 15 days.

The nitrite can be administered until a symptom of tissue damage in the subject improves. The symptom of tissue damage can include pain, skin pallor, numbness, swelling, ulceration, neuropathy, erythema, decreased plantar sensation, or defective tissue wound healing.

The amount of nitrate can be a dose of about 1 µg/kg to about 5000 µg/kg; about 0.5 µg/kg to about 1000 µg/kg; about 0.5 µg/kg to about 500 µg/kg; about 0.5 µg/kg to about 250 µg/kg; about 0.5 µg/kg to about 100 µg/kg; or about 0.5 µg/kg to about 50 µg/kg; about 165 µg/kg; about 16.5 µg/kg; or about 8.25 µg/kg. The nitrite can be administered to a circulating concentration in the subject of about 0.0005 µM to about 1.0 µM; about 0.001 µM to about 0.03 µM, of about 0.01 µM to about 0.05 µM, or about 0.05 to about 0.5 uM; about 0.5 µM, 0.3 µM, 0.03 µM; of about 0.003 µM; or of about 0.0015 µM.

In another embodiment, the nitrite or pharmaceutically acceptable salt thereof can be administered intraperitoneally, intravenously, subcutaneously, intramuscularly, transdermally, sublingually, or orally. The subject can have peripheral artery disease, diabetes, atherosclerotic cardiovascular disease, intermittent claudication, critical limb ischemic disease, defective wound healing, stroke, myocardial infarction, inflammatory bowel disease, a bone fracture, a bone infection, or peripheral neuropathy, avascular necrosis, rheumatoid arthritis, lupus, a bacterial infection, a fungal infection, fasciitis, or cellulitis. The diabetes can be type 1 or type 2 diabetes.

In another aspect, the tissue damage includes skeletal muscle, smooth muscle, cardiac muscle, neuronal tissue, skin, mesenchymal tissue, connective tissue, gastrointestinal tissue or bone.

In another embodiment, the method further includes administering an anti-ischemic therapy. an antimicrobial agent, an analgesic agent, an anti-inflammatory agent, a chemotherapeutic agent or a growth factor.

In another aspect, the tissue damage can be a wound. The wound can include skin, muscle, or a connective tissue and be the result of a traumatic injury, a congenital malformation, or a surgical procedure. The nitrite can be administered until the wound substantially heals.

In another embodiment, disclosed is a method of treating tissue necrosis in a subject, the method comprising: a) identifying a subject who has or who is at risk for tissue necrosis; and b) administering to the subject a pharmaceutical composition comprising inorganic nitrite or a pharmaceutically acceptable salt thereof, wherein the nitrite is administered for a time and in an amount sufficient to reduce said necrosis. The method can further include monitoring whether the subject experiences reduced necrosis. The subject can be a mammal; the mammal can be human.

The pharmaceutically acceptable salt of inorganic nitrite is sodium nitrite, potassium nitrite, or calcium nitrite. The nitrite can be administered one or more times a day for example, for at least about two to about twenty days; for at least about two days; at least about three days; at least about four days; at least about five days; at least about six days; at least about seven days; at least about 10 days; or at least about 15 days.

The nitrite can be administered until a symptom of tissue damage in the subject improves. The symptom of tissue damage can include pain, skin pallor, numbness, swelling, ulceration, neuropathy, erythema, decreased plantar sensation, gangrene or defective tissue wound healing.

The amount of nitrate can be a dose of about 1 µg/kg to about 5000 µg/kg; about 0.5 µg/kg to about 1000 µg/kg; about 0.5 µg/kg to about 500 µg/kg; about 0.5 µg/kg to about 250 µg/kg; about 0.5 µg/kg to about 100 µg/kg; or about 0.5 µg/kg to about 50 µg/kg; about 165 µg/kg; about 16.5 µg/kg; or about 8.25 µg/kg. The nitrite can be administered to a circulating concentration in the subject of about 0.0005 µM to about 1.0 µM; about 0.001 µM to about 0.03 µM, of about 0.01 µM to about 0.05 µM, or about 0.05 to about 0.5 uM; about 0.5 µM, 0.3 µM, 0.03 µM; of about 0.003 µM; or of about 0.0015 µm.

In another embodiment, the nitrite or pharmaceutically acceptable salt thereof can be administered intraperitoneally, intravenously, subcutaneously, intramuscularly, transdermally, sublingually, or orally. The subject can have peripheral artery disease, diabetes, atherosclerotic cardiovascular disease, intermittent claudication, critical limb ischemic disease, defective wound healing, stroke, myocardial infarction, inflammatory bowel disease, a bone fracture, a bone infection, or peripheral neuropathy, avascular necrosis, an autoimmune disease, a bacterial infection, a fungal infection, fasiculitis, or cellulitis. The diabetes can be type 1 or type 2 diabetes.

In another aspect, the tissue necrosis includes skeletal muscle, smooth muscle, cardiac muscle, neuronal tissue, skin, mesenchymal tissue, connective tissue, gastrointestinal tissue or bone. In another embodiment, the method further includes administering an anti-ischemic therapy, an antimicrobial agent, an analgesic agent, an anti-inflammatory agent, a chemotherapeutic agent or a growth factor.

In another aspect, the tissue necrosis can be a wound. The wound can include skin, muscle, or a connective tissue and be the result of a traumatic injury, a congenital malformation, or a surgical procedure. The nitrite can be administered until the wound substantially heals. In another aspect, the method further includes administering a surgical treatment. The surgical treatment can be surgical debridement, surgical drainage or tissue grafting.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 7A depicts nitric oxide production in iliac vein smooth muscle cells following growth for 24 hours in normoxic conditions; FIG. 7B depicts nitric oxide production in iliac vein smooth muscle cells following growth for 24 hours in hypoxic conditions.

FIG. 9A depicts nitric oxide production in aortic smooth muscle cells following growth for 24 hours in normoxic conditions; FIG. 9B depicts nitric oxide production in aortic smooth muscle cells following growth for 24 hours in hypoxic conditions.

FIG. 11A depicts nitric oxide production in coronary artery endothelial cells following growth for 24 hours in normoxic conditions; FIG. 11B depicts nitric oxide production in coronary artery endothelial cells following growth for 24 hours in hypoxic conditions.

FIGS. 13A and 13B depict an analysis of nitric oxide production in umbilical vein endothelial cells grown in various concentrations of sodium nitrite for 24 hours. FIG. 13A depicts nitric oxide production in umbilical vein endothelial cells following growth for 24 hours in normoxic conditions; FIG. 13B depicts nitric oxide production in umbilical vein endothelial cells following growth for 24 hours in hypoxic conditions.

FIG. 15A depicts nitric oxide production in smooth muscle and endothelial cells following growth for 24 hours in hypoxic conditions in the presence of 500 uM sodium nitrite. FIG. 15B depicts nitric oxide production in smooth muscle and endothelial cells following growth for 24 hours in hypoxic conditions in the presence of 100 uM sodium nitrite.

FIGS. 18A and 18B depict the results of an analysis of the effect of chronic sodium nitrite treatment on mouse weight and blood glucose levels in an aged diabetes mouse model. FIG. 18A depicts body weight in aged diabetic mice receiving chronic sodium nitrite treatment. FIG. 18B depicts blood glucose levels in aged diabetic mice receiving chronic sodium nitrite treatment.

FIG. 19A depicts sodium cholesterol levels in aged diabetic mice receiving chronic sodium nitrite treatment. FIG. 19B depicts serum LDL levels in aged diabetic mice receiving chronic sodium nitrite treatment.

FIG. 21A depicts vascular density in aged diabetic mice receiving chronic sodium nitrite treatment. FIG. 21B depicts cell proliferation index in aged diabetic mice receiving chronic sodium nitrite treatment.

FIG. 22A depicts the hindlimbs of animals in the PBS control group. FIG. 22B depicts the hindlimbs of animals in the chronic sodium nitrite treatment group.

FIG. 24A depicts NO production in cells treated with 100 uM sodium nitrite. FIG. 24B depicts NO production in cells treated with 0.01 uM sodium nitrite.

FIGS. 25A and 25B depict the results of an analysis of myogenin gene expression in ischemic muscle. FIG. 25A depicts the results of an analysis of in vivo myogenin expression in ischemic grastrocnemius muscle following chronic sodium nitrite treatment. FIG. 25B depicts the results of an analysis of myogenin expression in C2C12 myoblast cells under hypoxic conditions in the presence of decreasing concentrations of sodium nitrite.

FIG. 26A depicts expression profiles at day 3 of sodium nitrite treatment. FIG. 26B depicts expression profiles at day 7 of sodium nitrite treatment.

FIG. 27 depicts a key to the symbols in FIGS. 1-6.

FIGS. 28A to 28J are a table listing the genes identified at day 3 of chronic sodium nitrite treatment in a mouse ischemic hindlimb model.

FIGS. 29A to 29G are a table listing the genes identified at day 7 of chronic sodium nitrite treatment in a mouse ischemic hindlimb model. Like reference symbols in the various drawings indicate like elements.

DETAILED DESCRIPTION

Figure 1:
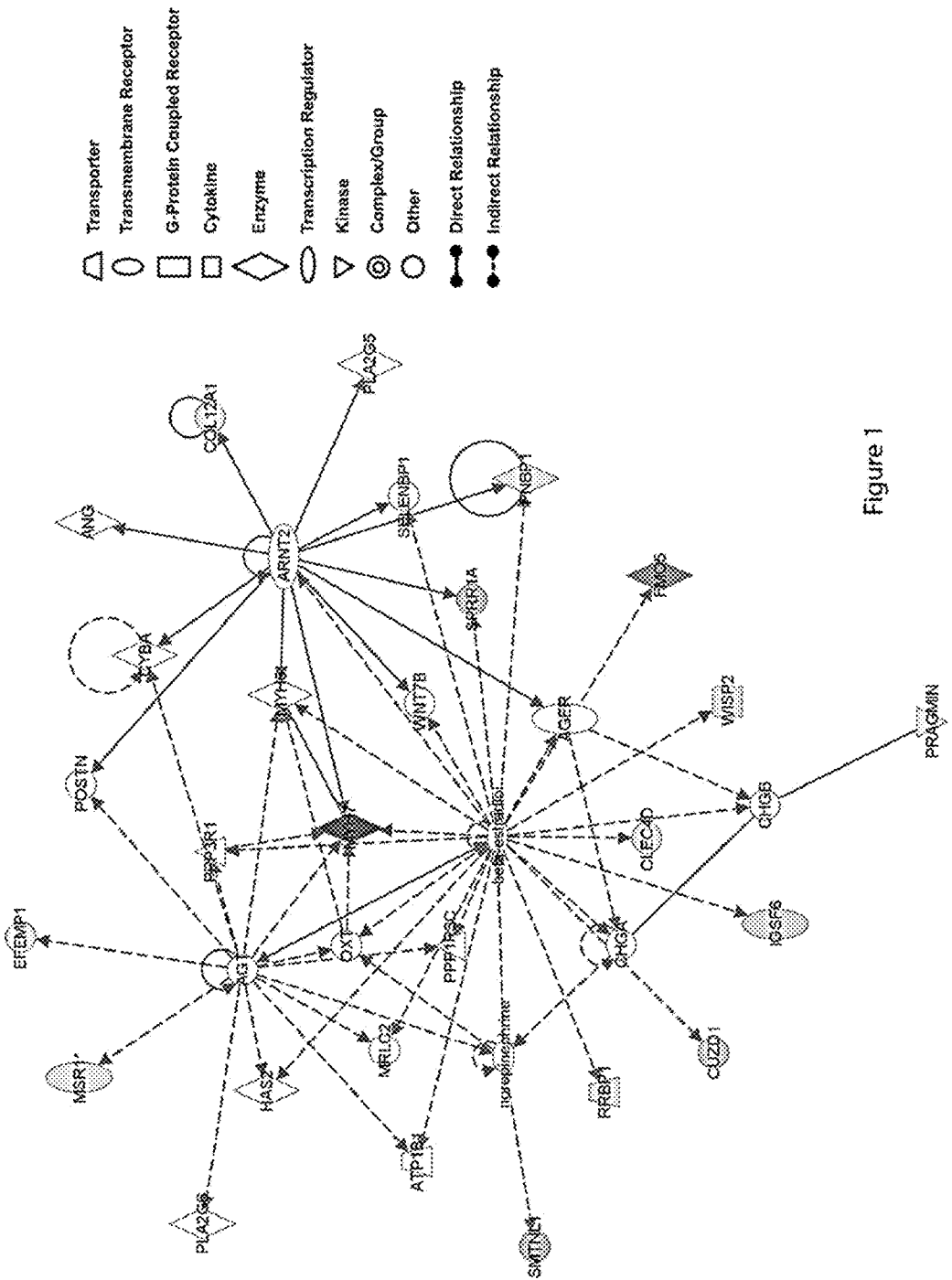
FIG. 1 depicts the results of a gene array analysis demonstrating that chronic sodium nitrite treatment altered the expression of genes involved in cardiovascular system development and function, tissue morphology, and carbohydrate metabolism. Genes enhanced following sodium nitrite administration included flavin containing monoxygenase 5, smoothelin like 1, mysoin heavy chain 7, CUB zona pellucida like domains 1 and small proline rich protein 1A. Genes inhibited include collagen 12, 1A, C-type lectin domain family 4D, formin binding protein 1, macrophage scavenger receptor 1, EGF containing fibulin-like extracellular matrix protein 1, immunoglobulin superfamily member 6, homolog of rat pragma of Rnd2, ribosomal binding protein 1 homolog (180 kDa) and WNT1 inducible signaling pathway protein 2.

We further describe below the present methods for treatment of tissue damage. These methods can be applied to, and are expected to benefit subjects having any of a variety of medical conditions that can give rise to tissue damage. The methods are based, inter alia, on the inventor's discovery that administration of inorganic nitrite or a pharmaceutical composition comprising inorganic nitrite to a subject having tissue damage results in the selective reduction of symptoms of tissue damage and tissue necrosis and the inhibition or enhancement of genes associated with tissue remodeling and tissue regeneration.

Compositions

The pharmaceutically acceptable compositions of the invention include inorganic nitrite, e.g., a salt or ester of nitrous acid ($HNO_2$) or a pharmaceutically acceptable salt thereof. The nitrite ion is $NO_2-$. More generally, a nitrite compound is either a salt or an ester of nitrous acid. Nitrite salts can include, without limitation, salts of alkali metals, e.g., sodium, potassium; salts of alkaline earth metals, e.g., calcium, magnesium, and barium; and salts of organic bases, e.g., amine bases and inorganic bases. Compounds of the invention also include all isotopes of atoms occurring in the intermediate or final compounds. Isotopes include those atoms having the same atomic number but different mass numbers. For example, isotopes of hydrogen include tritium and deuterium. The term, "compound," as used herein with respect to any inorganic nitrite or pharmaceutically acceptable salt thereof and is meant to include all stereoisomers, geometric iosomers, tautomers, and isotopes of the structures depicted. All compounds, and pharmaceuticaly acceptable salts thereof, are also meant to include solvated or hydrated forms.

The compounds of the present invention can be prepared in a variety of ways known to one of ordinary skill in the art of chemical synthesis. The compounds of the present invention can be synthesized using the methods described below, together with synthetic methods known in the art of synthetic chemistry or variations thereon as appreciated by one of ordinary skill in the art. Methods for preparing nitrite salts are well known in the art and a wide range of precursors and nitrite salts are readily available commercially. Nitrites of the alkali and alkaline earth metals can be synthesized by reacting a mixture of nitrogen monoxide (NO) and nitrogen dioxide ($NO_2$) with a corresponding metal hydroxide solution, as well as through the thermal decomposition of the corresponding nitrate. Other nitrites are available through the reduction of the corresponding nitrates.

The present compounds can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one of ordinary skill in the art by routine optimization procedures.

Regardless of their original source or the manner in which they are obtained, the compounds of the invention can be formulated in accordance with their use. For example, the compounds can be formulated within compositions for application to cells in tissue culture or for administration to a patient. When employed as pharmaceuticals, any of the present compounds can be administered in the form of pharmaceutical compositions. These compositions can be prepared in a manner well known in the pharmaceutical art, and can be administered by a variety of routes, depending upon whether local or systemic treatment is desired and upon the area to be treated.

Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal or intramuscular injection or infusion; or intracranial, e.g., intrathecal or intraventricular administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids, powders, and the like. Conventional pharmaceutical carriers, aqueous, powder or oily bases, thickeners and the like may be necessary or desirable.

This invention also includes pharmaceutical compositions which contain, as the active ingredient, one or more of the compounds described herein in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semisolid, or liquid material (e.g., nonnal saline), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. As is known in the art, the type of diluent can vary depending upon the intended route of administration. The resulting compositions can include additional agents, such as preservatives. The compounds may also be applied to a surface of a device (e.g., a catheter) or contained within a pump, patch, or other drug delivery device. The therapeutic agents of the invention can be administered alone, or in a mixture, in the presence of a pharmaceutically acceptable excipient or carrier (e.g., physiological saline). The excipient or carrier is selected on the basis of the mode and route of administration. Suitable pharmaceutical carriers, as well as pharmaceutical necessities for use in pharmaceutical formulations, are described in provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The pharmaceutical compositions can be formulated so as to provide quick, sustained or delayed release of the active ingredient after administration to the patient by employing procedures known in the art.

The compositions can be formulated in a unit dosage form, each dosage containing, for example, from about 0.1 mg to about 50 mg, from about 0.1 mg to about 40 mg, from about 0.1 mg to about 20 mg, from about 0.1 mg to about 10 mg, from about 0.2 mg to about 20 mg, from about 0.3 mg to about 15 mg, from about 0.4 mg to about 10 mg, from about 0.5 mg to about 1 mg; from about 0.5 mg to about 100 mg, from about 0.5 mg to about 50 mg, from about 0.5 mg to about 30 mg" from about 0.5 mg to about 20 mg, from about 0.5 mg to about 10 mg, from about 0.5 mg to about 5 mg; from about 1 mg from to about 50 mg, from about 1 mg to about 30 mg" from about 1 mg to about 20 mg, from about 1 mg to about 10 mg, from about 1 mg to about 5 mg; from about 5 mg to about 50 mg, from about 5 mg to about 20 mg, from about 5 mg to about 10 mg; from about 10 mg to about 100 mg, from about 20 mg to about 200 mg, from about 30 mg to about 150 mg, from about 40 mg to about 100 mg, from about 50 mg to about 100 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above 10 containing from, for example, 0.1 to about 500 mg of the active ingredient of the present invention.

The tablets or pills of the present invention can be coated or otherwise compounded to provide a dosage form affording the advantage of prolonged action. Exemplary methods of such formulations are described in U.S. application No. 61/251,483, which is herein incorporated by reference. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release.

A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described herein and/or known in the art. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine.

Solution, suspension, or powder compositions can be administered orally or nasally from devices which deliver the formulation in an appropriate manner.

The compositions administered to a patient can be in the form of one or more of the pharmaceutical compositions described above. These compositions can be sterilized by conventional sterilization techniques or may be sterile filtered. Aqueous solutions can be packaged for use as is, or lyophilized, the lyophilized preparation being combined with a sterile aqueous carrier prior to administration. The pH of the compound preparations typically will be between about 3 and 11, for example, between about 5 to 9, between 6 and 7, between 7 and 8. It will be understood that use of certain of the foregoing excipients, carriers, or stabilizers will result in the formation of pharmaceutical salts.

The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration.

Methods of Treatment

Tissue damage is associated with a wide range of medical conditions that result in cellular injury and/or damage to the extracellular matrix which surrounds the cells in some tissue types and may be the result of disease, injury, or of an unknown cause, and may be influenced by one's genetic constitution. Regardless of the medical condition leading to tissue damage, a patient who has damaged tissue is a candidate for treatment with the pharmaceutically acceptable compositions comprising inorganic nitrite described herein. Treatment can completely or partially abolish some or all of the signs and symptoms of tissue damage, decrease the severity of the symptoms, delay their onset, or lessen the progression or severity of subsequently developed symptoms.

Tissue Damage and Regeneration

As described further below, the compositions of the invention are administered for a time and in an amount sufficient to reduce tissue damage or a symptom of tissue damage improves. Symptoms of tissue damage may vary depending upon the nature of the damage and the tissue type involved, but can include pain, skin pallor, numbness, swelling, ulceration, neuropathy, erythema, decreased plantar sensation, or defective tissue wound healing. We may use the terms "tissue regeneration," "tissue repair" and "tissue remodeling" interchangeably. Tissue regeneration refers to all phases of the process of regeneration, including, for example the initial signaling events, induction of endothelial cell proliferation, enhancement of gene expression of genes involved in cell proliferation, tissue morphology and development, carbohydrate metabolism, cell assembly, molecular transport and induction of stem or progenitor cell growth and differentiation.

When tissues become damaged, an ordered series of physiological events must take place in a timely fashion for successful tissue regeneration to occur. The first events, termed the inflammatory phase, include blood clotting as well as the arrival at the site of damaged cells that remove bacteria, debris and damaged tissue. Later, circulating stem cells migrate to the site and differentiate into tissue-specific cell types. Finally, the differentiated cells begin to produce and deposit new extracellular matrix (ECM), a complex mixture of carbohydrates and proteins that provides support and anchorage for cells. The nature of tissue regeneration and repair depends in part on the extent of the damage, that is, the damaged cells themselves can be repaired in a process sometimes termed resolution, the dead cells can be replaced with the same cell type (regeneration), or the lost tissue can be replaced with scar tissue in a process termed fibrosis. These processes may occur simultaneously or sequentially.

The methods and compositions described herein can be used to treat any of a wide range of disorders in which amelioration or repair of tissue damage is needed. Tissue defects can arise from diverse medical conditions, including, for example, congenital malformations, traumatic injuries, infections, and oncologic resections. Thus, the compositions can be used to promote regeneration and repair in any soft tissue, e.g., tissues that connect, support, or surround other structures and organs of the body. The methods and compositions can also be used to promote bone repair, e.g., as a periosteal graft to support bone or an articular graft to drive cartilage repair. Soft tissue can be any non-osseous tissue. Soft tissue can also be epithelial tissue, which covers the outside of the body and lines the organs and cavities within the body. Examples of epithelial tissue include, but are not limited to, simple squamous epithelia, stratified squamous epithelia, cuboidal epithelia, or columnar epithelia.

Soft tissue can also be connective tissue, which functions to bind and support other tissues. One example of connective tissue is loose connective tissue (also known as areolar connective tissue). Loose connective tissue, which functions to bind epithelia to underlying tissues and to hold organs in place, is the most widely distributed connective tissue type in vertebrates. It can be found in the skin beneath the dermis layer; in places that connect epithelium to other tissues; underneath the epithelial tissue of all the body systems that have external openings; within the mucus membranes of the digestive, respiratory, reproductive, and urinary systems; and surrounding the blood vessels and nerves. Loose connective tissue is named for the loose "weave" of its constituent fibers which include collagenous fibers, elastic fibers (long, thread-like stretchable fibers composed of the protein elastin) and reticular fibers (branched fibers consisting of one or more types of very thin collagen fibers). Connective tissue can also be fibrous connective tissue, such as tendons, which attach muscles to bone, and ligaments, which joint bones together at the joints. Fibrous connective tissue is composed primarily of tightly packed collagenous fibers, an arrangement that maximizes tensile strength. Soft tissue can also be muscle tissue. Muscle tissue includes: skeletal muscle, which is responsible for voluntary movements; smooth muscle, which is found in the walls of the digestive tract, bladder arteries and other internal organs; and cardiac muscle, which forms the contractile wall of the heart.

The methods and compositions can be used to promote regeneration and repair of soft tissue in many different organ systems that fulfill a range of physiological functions in the body. These organ systems can include, but are not limited to, the muscular system, the genitourinary system, the gastroenterological system, the integumentary system, the circulatory system and the respiratory system. The compositions are particularly useful for support of regeneration of endothelial, muscle, cardiovascular tissue and epithelial tissue. The compositions and methods of the invention enhance the expression of genes associated with tissue remodeling and muscle growth, modulate the expression of genes associated with inflammation, and differentially stimulate new blood vessel growth as described in WO 2009/065142, which is herein incorporated by reference.

Tissue Necrosis

A particularly severe form of tissue damage is tissue necrosis. We tend to use the terms "tissue necrosis" and "necrosis" interchangeably. Symptoms of tissue necrosis may vary depending upon the nature of the damage and the tissue type involved, but can include pain, skin pallor, numbness, swelling, ulceration, neuropathy, erythema, decreased plantar sensation, defective tissue wound healing, skin blackening, gangrene and exudation. Tissue necrosis is associated with a wide range of medical conditions that result in cellular injury may be the result of disease, injury, infection, envenomation, toxins or of an unknown cause, and may be influenced by one's genetic constitution. Unlike apoptosis, which is a highly regulated, often beneficial process of cell death, necrosis typically begins with cell swelling, chromatin digestion, disruption of the plasma membrane and organelle membranes. Late necrosis is characterized by extensive DNA hydrolysis, vacuolation of the endoplasmic reticulum, organelle breakdown, and cell lysis. The release of intracellular content, particularly lysosomal enzymes, after plasma membrane rupture triggers death of surrounding cells. Tissue necrosis can require surgical removal, or debridement, and may in some cases necessitate amputation of the affected area; severe necrosis may in some cases, result in death.

Histologically, there are a number of different morphological patterns of necrosis: 1) coagulative necrosis, typically seen in hypoxic (low oxygen) environments, such as an infarction. Cell outlines remain after cell death and can be observed by light microscopy; 2) liquefactive necrosis (or colliquative necrosis) which is usually associated with cellular destruction and pus formation (e.g. pneumonia), is typical of bacterial or fungal infections because of their ability to stimulate an inflammatory reaction; 3) gummatous necrosis is restricted to necrosis involving spirochaetal infections (e.g. syphilis); 4) haemorrhagic necrosis, due to blockage of the venous drainage of an organ or tissue (e.g. in testicular torsion); 5) caseous necrosis, a specific form of coagulation necrosis typically caused by mycobacteria (e.g. tuberculosis), fungi, and some foreign substances; 6) fatty necrosis results from the action of lipases on fatty tissues (e.g. acute pancreatitis, breast tissue necrosis); and 7) fibrinoid necrosis, caused by immune-mediated vascular damage is marked by deposition of fibrin-like proteinaceous material in arterial walls.

Disorders or conditions associated with tissue necrosis or that put a patient at risk for tissue necrosis, for example, peripheral artery disease, diabetes, atherosclerotic cardiovascular disease, intermittent claudication, critical limb ischemic disease, defective wound healing, stroke, myocardial infarction, inflammatory bowel disease, a bone fracture, a bone infection, or peripheral neuropathy, avascular necrosis, an autoimmune disease, a bacterial infection, e.g., a Group A *streptococcus* infection, Bacillaceae infections such as *Bacillus anthracis*, a fungal infection, venomous spider bites, venomous snake bites, frostbite, osteonecrosis, fasiculitis, or cellulitis Nitric Oxide The methods and compositions provided herein can induce the preferential formation of nitric oxide in damaged tissue. Nitric oxide (NO) has been shown to positively regulate endothelial cell responses, can stimulate tissue regeneration, enhance stem cell growth and proliferation and alter inflammatory responses. NO increases the expression of various angiogenic factors, including YEOF, which, together with other mediators, increases NO levels via a positive feedback mechanism. In addition to stimulating the growth of endothelial cells, NO can also protect tissues against ischemic damage by slowing cellular respiration. NO has been shown to modulate several endothelial cell signaling pathways for example, Erk 112 and PKC. In the present invention, NO is found to accelerate tissue healing and recovery by augmenting angiogenic responses involving redox dependent pathways while diminishing inflammatory responses.

The primary enzyme responsible for NO production in the cardiovascular system is endothelial nitric oxide synthase (eNOS) which is regulated by numerous molecules and signaling pathways. Importantly, eNOS activity is also largely responsible for systemic NO production as the amount of enzyme expression is often directly proportional to NO metabolite levels. NO readily diffuses across lipid bilayers and its biological fate is dictated predominately by reactions with metalloproteins and other free radical species; the classic example being activation of the heme enzyme soluble guanylate cyclase (sGC) which initiates a signal cascade leading to vessel dilation and platelet inhibition. In addition, NO may also be oxidized through various mechanisms resulting in the formation of nitrite which can be further oxidized to nitrate ($NO_3$)—.

Both nitrite and nitrate are involved in regulating production of NO from NOS independent pathways. Inorganic nitrite can undergo a one electron reduction back to NO through various mechanisms with oxygen-binding heme proteins (hemoglobin and myoglobin), deoxyhemoglobin, deoxymyoglobin, xanthine oxidoreductase, endothelial nitric oxide synthase, acidic disproportionation, and members of the mitochondrial electron transport chain, e.g., mitochondrial heme proteins all being potential electron donors. The ability of nitrite to be reduced back to NO classifies it as a unique NO donor under biological conditions, e.g., tissue ischemia, in which many of these potential reducing agents are active. NO interacts with several intracellular targets to form various NO-containing species including S-nitrosothiols, C— or N—S-nitroso compounds, and nitrosylheme adducts. Moreover, these nitro so-products may serve as a biological reservoir for NO, which can be liberated under certain conditions Administration The present methods for treating tissue damage are carried out by administering an inorganic nitrite for a time and in an amount sufficient to result a reduction in tissue damage. The amount and frequency of administration of the compositions can vary depending on, for example, what is being administered, the state of the patient, and the manner of administration. In therapeutic applications, compositions can be administered to a patient suffering from tissue damage in an amount sufficient to relieve or least partially relieve the symptoms of tissue damage and its complications. In some embodiments, compositions can be administered to a patient suffering from a condition that carries a risk for tissue necrosis in an amount sufficient to reduce the likelihood of tissue necrosis. The dosage is likely to depend on such variables as the type and extent of progression of the tissue damage, any associated inflammatory conditions, the amount of damage in the tissue, the severity of the inflammation or tissue damage, the age, weight and general condition of the particular patient, the relative biological efficacy of the composition selected, formulation of the excipient, the route of administration, and the judgment of the attending clinician. Effective doses can be extrapolated from dose response curves derived from in vitro or animal model test system. An effective dose is a dose that produces a desirable clinical outcome by, for example, improving a sign or symptom of tissue damage or inflammation or reversing or slowing tissue damage progression.

The amount of inorganic nitrite per dose can vary. For example, a subject can receive from about 0.05 µg/kg to about 5000 µg/kg, e.g., about 0.05, 1, 5, 10, 25, 50, 100, 200, 250, 300, 400, 450, 500, 550, 600, 650, 700, 750, 800, 850, 900, 1000, 1250, 1500, 2000, 2500, 3000, 3500, 4000, 4500 or 5000 µg/kg. Generally, we administer nitrite in an amount such that the circulating concentration does not exceed 1.0 µM, e.g., 0.0005 µM, 0.001 µM, 0.002 µM, 0.003 µM, 0.004 µM, 0.005 µM, 0.01 µM, 0.02 µM, 0.03 µM, 0.04 µM, 0.05 µM, 0.1 µM, 0.15 µM, 0.2 µM, 0.25 µM, 0.3 µM, 0.35 µM, 0.4 µM, 0.45 µM, 0.5 µM, 0.55 µM, 0.6 µM, 0.65 µM, 0.7 µM, 0.75 µM, 0.8 µM, 0.85 µM, 0.9 µM, 0.95 µM, or 1.0 µM. Thus, exemplary dosages can include 8.25 µg/kg, 16.5 µg/kg or 165 µg/kg and exemplary circulating plasma concentrations can include 0.0015 µM, 0.003 µM or 0.030 µM, 0.30 µM or 0.50 µM.

The frequency of treatment may also vary. The subject can be treated one or more times per day (e.g., once, twice, three, four or more times) or every so-many hours (e.g., about every 2, 4, 6, 8, 12, or 24 hours). The time course of treatment may be of varying duration, e.g., for two, three, four, five, six, seven, eight, nine, ten, fifteen, twenty, twenty five, thirty, thirty-five, forty, forty-five, fifty, fifty-five, sixty, sixty-five, seventy or more days. For example, the treatment can be twice a day for three days, twice a day for seven days, twice a day for ten days. Treatment cycles can be repeated at intervals, for example weekly, bimonthly or monthly, which are separated by periods in which no treatment is given. The treatment can be a single treatment or can last as long as the life span of the subject (e.g., many years).

Method of the invention are applicable to any of a wide range of medical conditions which have as their underlying feature a persistent or progressive tissue damage due in part to reduction of oxygen levels in a tissue or organ. Thus, the methods are applicable to treatment of tissue damage associated with a disorder, with a trauma or an environmental stress. The reduction in oxygen levels can be, for example, the result of a progressive blockage of an artery due to hardening and/or loss of elasticity due to an atheromatous plaque or the presence of a clot. Reduction of oxygen levels in a tissue can also be the result of an environmental insult, for example, a traumatic injury or surgical procedure that interrupts the blood flow to a tissue or organ. Typically, the oxygen tension of a wound quickly and progressively decreases with the development of varying degrees of hypoxia throughout the wound region. Environmental conditions that induce hypoxia are also within the scope of the invention.

Disorders encompassed by the invention include, for example, cardiovascular disease, peripheral artery disease, arteriosclerosis, atherosclerotic cardiovascular disease, myocardial infarction, critical limb ischemic disease, stroke, acute coronary syndrome, intermittent claudication, diabetes, including type 1 and type 2 diabetes, skin ulcers, peripheral neuropathy, inflammatory bowel disease, ulcerative colitis, Crohn's disease, intestinal ischemia, and chronic mesenteric ischemia.

The methods of the invention are also applicable to tissue damage associated with a trauma, for example, a traumatic injury such as a wound, laceration, burn, contusion, bone fracture or chronic infection. Also encompassed by the invention are tissue injuries sustained as part of any surgical procedure, for example, endarterectomy. Procedures involving tissue or organ transplantation are within the scope of the invention. Examples include vascular bypass grafts, heart, liver, lung, pancreatic islet cell transplantation as well as transplantation of tissues generated ex vivo for implantation in a host. The methods of the invention are also useful for treating tissue damage brought about by exposure to an environmental insult, for example, chronic exposure to hypoxic conditions e.g., high altitude, or sustained aerobic exertion.

The methods provided herein are applicable to any of a wide range of tissue types including, for example, muscle, smooth muscle, skeletal muscle, cardiac muscle, neuronal tissue, skin, mesechymal tissue, connective tissue, gastrointestinal tissue or bone. Soft tissue, such as epithelial tissue, e.g., simple squamous epithelia, stratified squamous epithelia, cuboidal epithelia, or columnar epithelia, loose connective tissue (also known as areolar connective tissue), fibrous connective tissue, such as tendons, which attach muscles to bone, and ligaments, which join bones together at the joints.

The methods of the invention can include the steps of identifying a subject (e.g., a human patient) who is experiencing tissue damage or who is experiencing or is likely to experience tissue necrosis. Since tissue damage can result from a wide range of medical conditions all of which have as their underlying feature a persistent reduction of oxygen levels in a tissue, the specific signs and symptoms will vary depending upon factor or factors responsible for the reduction of oxygen levels.

Tissue damage can result from chronic tissue ischemia in peripheral artery disease (PAD), a form of peripheral vascular disease in which there is partial or total blockage of an artery, usually due to atherosclerosis in a vessel or vessels leading to a leg or arm, can include intermittent claudication, that is, fatigue, cramping, and pain in the hip, buttock, thigh, knee, shin, or upper foot during exertion that goes away with rest, claudication during rest, numbness, tingling, or coldness in the lower legs or feet, neuropathy, or defective tissue wound healing. PAD in the lower limb is often associated with diabetes, particularly type 2 diabetes. Arm artery disease is usually not due to atherosclerosis but to other conditions such as an autoimmune disease, a blood clot, radiation therapy, Raynaud's disease, repetitive motion, and trauma. Common symptoms when the arm is in motion include discomfort, heaviness, tiredness, cramping and finger pain. PAD can be diagnosed by performing one or more diagnostic tests including, for example, an ankle brachial index (ABI) test, angiography, ultrasound, or MRI analysis.

Myocardial ischemia can have few or no symptoms, although typically, it is associated with a symptoms such as angina, pain, fatigue elevated blood pressure. Diagnostic tests for myocardial ischemia include: angiography, resting, exercise, or ambulatory electrocardiograms; scintigraphic studies (radioactive heart scans); echocardiography; coronary angiography; and, rarely, positron emission tomography.

The method of the invention can also be used in conjunction with other remedies known in the art that are used to treat tissue damage including, drug therapy, surgery, anti-inflammatory agents, antibodies, exercise, or lifestyle changes. The choice of specific treatment may vary and will depend upon the severity of the tissue damage, the subject's general health and the judgment of the attending clinician. The present compositions can also be formulated in combination with one or more additional active ingredients, which can include any pharmaceutical agent such antihypertensives, anti-diabetic agents, statins, anti-platelet agents (clopidogrel and cilostazol), antibodies, immune suppressants, anti-inflammatory agents, antibiotics, chemotherapeutics, and the like. The compositions and methods described herein can be administered in conjunction with standard therapies for tissue necrosis including removal of the necrotic tissue by surgical means, chemical removal, via an enzymatic debriding agent, or removal by maggot therapy.

EXAMPLES

Example 1 Materials and Methods

Animals and Reagents.

Unless otherwise stated, male wild type (C57BL16J) mice weighing 20-25 gm and age 2-3 months were used. The mice were bred and housed at the Association for Assessment and Accreditation of Laboratory Animal Care, International accredited LSUHSC-Shreveport animal resource facility and maintained according to the National Research Council's Guide for Care and Use of Laboratory Animals. All experimental protocols were approved by the LSU Institutional Animal Care and Use Committee. Sodium nitrite, sodium nitrate, phosphate buffered saline (PBS), and all other chemicals were purchased from Sigma Chemical (St Louis, Mo.).

Hind-Limb Ischemia Model.

Hind limb ischemia was induced by ligating the left common femoral artery proximal to origin of profunda femoris artery according to Senthilkumar, A., Smith, R. D., Khitha, J., Arora, N., Veerareddy, S., Langston, W., Chidlow, 1H., Jr., Barlow, S. c., Teng, x., Patel, R. P., et al. 2007. Arterioscler Thromb Vasc Biol 27: 1947-1954. Mice were anesthetized with intraperitoneal injection of ketamine (100 mglkg) and xylazine (8 mglkg); surgery was performed under aseptic conditions. The common femoral vein and femoral nerve were dissected away from the artery. Two ligatures were placed in the common femoral artery proximal to the profunda femoris artery and then transected between the two ligations. The incision was then closed and the ligation was immediately verified by laser Doppler measurement of tissue blood flow. Following Hind-limb ligation was performed on mice which received either PBS or sodium nitrite (165 µg/kg) twice daily injection.

Gene Analysis.

RNA isolation and microarray hybridization: Total RNA was isolated from either PBS or sodium nitrite (165 µg/kg) treated gastrocnemius muscle tissues specimens at day 3 or day 7 post-ischemia using the RNeasy Midi Kit (Qiagen, Chatswort, Calif.). RNA integrity was checked using the Agilent 2100 Bioanalyzer (Agilent Technologies, Palo Alto, Calif.). The RNA integrity number (RIN) for all specimens used for gene array analysis was between 8-9. Double stranded cDNA was synthesized from 5 ug total RNA using a Superscript cDNA synthesis Kit (Invitrogen, Carlsbad, Calif.) and purified using the Gene Chip Sample Cleanup Module (Affymetrix, Santa Vlara, Calif.). After biotin-labeling, the cDNA were fragmented at 94° C. and hybridized to the GeneChip® Mouse Genome 430 2.0 Array (Affymetrix), which contains 39,000 fully annotated transcripts of the mouse genome. After washing and staining, the arrays were scanned using GeneChip Scanner 3000 (Affymetrix) and hybridization efficiency determined by housekeeping control and spike control probe sets. Analysis of all control probe sets received a pass call demonstrating consistent hybridization efficiency across all specimens.

Microarray data normalization and analysis. Array data were globally scaled to a target intensity value of 500 to compare individual array experiments. To determine differentially expressed genes between PBS and nitrite treatment, data were log transformed and uploaded into Genesifter program (www.genesifter.net). Identification of significant changes in gene expression were determined using a pair-wise comparison of PBS versus nitrite therapy gene array data at each individual time point with the following criteria: a minimal 2-fold difference in expression with no maximal threshold limit, a hybridization quality cutoff of 1, and an unpaired student t-test between treatment groups followed by Benjamini and Hochberg post test to limit false discovery rates.

Genes which were significantly altered as identified by Genesifter analysis were uploaded into Ingenuity software (www.ingenuity.com) to perform network analysis using the Ingenuity Pathway Knowledge Base, which is a data base created from data mining for expression and functional relationships between molecules extracted from previously published peer reviewed papers found in NCBI Pubmed, Medline, and several other databases. The resulting output of network analysis was broken down according to the genetic composition of networks, the biological function of the networks, the number of interrelated network relationships, as well as statistical analysis of individual networks.

Cell System

A contained hypoxia tissue culture system was used allowing the long term culturing of cells in hypoxia (24 hrs). A fluorescent plate reader in hypoxic chamber measured NO formation using the fluorescent dye DAF-FM. The primary human vascular cell cultures used to monitor sodium nitrite activity were iliac vein smooth muscle cell, aortic smooth muscle cell, coronary artery endothelial cell and umbilical vein endothelial cell.

Example 2 the Effect of Chronic Sodium Nitrite Treatment on Gene Expression in a Mouse Hindlimb Ischemia Model We examined the effect of chronic sodium nitrite treatment on ischemic tissue gene expression in the mouse hind-limb ischemia model described in Example 1. Induction of chronic hind limb ischemia was performed according to the method in Example 1. Sodium nitrite treatment (165 µg/kg) or PBS control treatments was begun the afternoon after hind limb ligation via intraperitoneal injection. Nitrite doses were given once in the morning (8 am) and a second in the afternoon (5 pm) with muscle tissue harvested on the morning of the $4^{th}$ and $8^{th}$ days (to give an entire 3 and 7 day period for study). Four muscle specimens from individual mice were harvested per treatment cohort per time point for a total of 16 individual specimens for gene array analysis. Harvested tissue was immediately frozen in liquid nitrogen for subsequent total RNA isolation. Laser doppler blood flow measurements were taken from non-ischemic and ischemic hind limbs prior to tissue collection to determine the amount of ischemic tissue perfusion using a Vasamedics Laserflo BPM2 deep tissue penetrating doppler device. Percent restoration of blood flow was determined by dividing the ischemic hind limb blood flow by the non-ischemic hind limb blood flow and multiplying by 100. Statistical analysis of changes in tissue blood flow between treatment groups at specific time points were performed with an unpaired students t-test using Prism software (Graphpad).

Figures 26A, 26B:
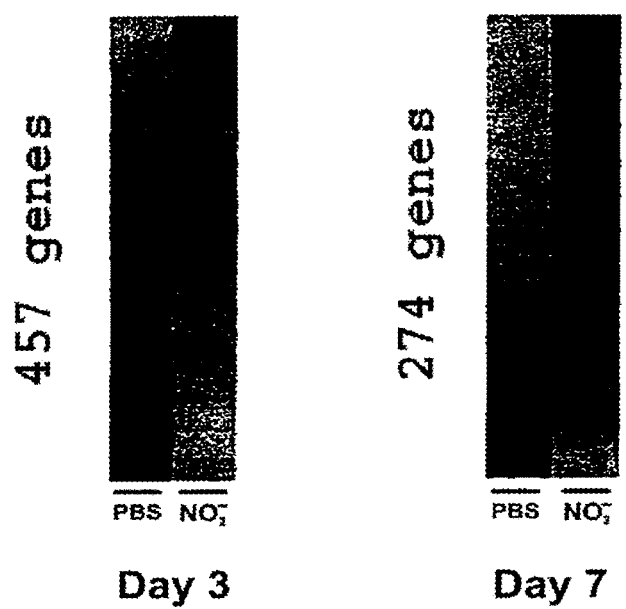
FIGS. 26A and 26B depict the results of a heat map analysis of gene expression profiles in sodium nitrite treated and PBS control treated ischemic tissue.

Heat map results of PBS control and sodium nitrite gene expression profiles at day 3 are shown in FIG. 26A. 457 distinct gene expression profiles were significantly altered, with sodium nitrite treatment eliciting a large down regulation of 346 genes compared to up-regulation of 111 genes. Conversely, sodium nitrite therapy differentially impacted the expression profile of 274 genes at day 7 of ischemia as shown in FIG. 26B. However, the majority of these genes were up-regulated (219 genes) compared to fewer that were down-regulated (55 genes). Table 1 (shown in FIGS. 28A to 28J) and 2 (shown in FIGS. 29A to 29G) list the genes, expression levels, and p-values which were identified at days 3 and 7, respectively. Together, these data revealed an unexpected gene expression profile pattern whereby nitrite treatment mediated a large and preferential down-regulation of gene expression at day 3 which transitioned to a smaller yet positively up-regulated group of genes at day 7.

Figure 2:
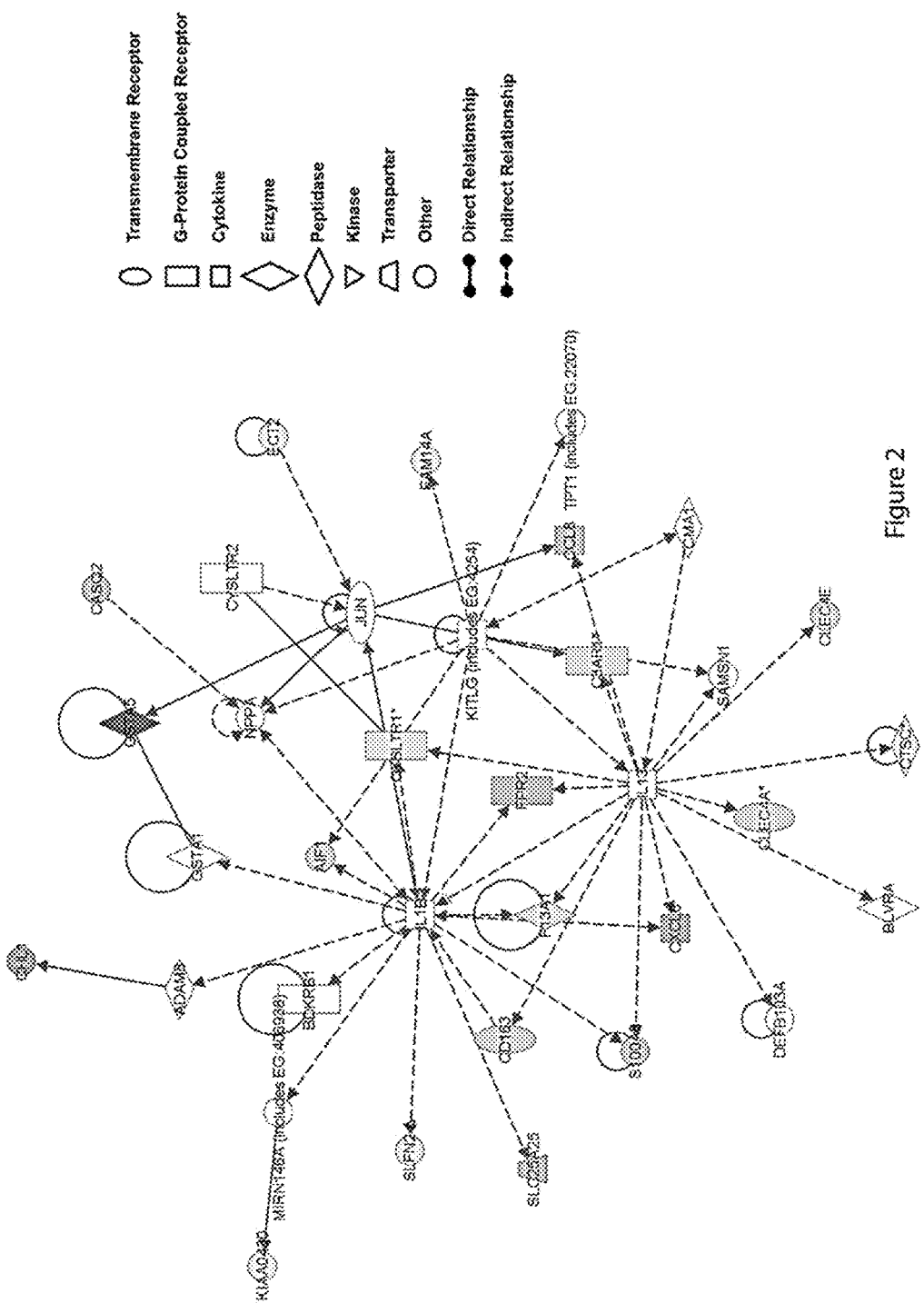
FIG. 2 depicts the results of a gene array analysis demonstrating that chronic sodium nitrite treatment altered the expression of genes involved in antigen presentation, cell mediated immunity, and humoral mediated immunity. Genes enhanced following sodium nitrite administration include calsequestrin 2, GST alpha 5, and solute carrier family member 25. Genes inhibited include allograft inflammatory factor 1, complement component 3a receptor 1, CD163, CAM homology to L1CAM, C-type lectin domain family 4, A, C-type lectin domain family 4, E, cathepsin C, CXCL6, cysteinyl leukotriene receptor 1, epithelial cell transforming sequence 2 oncogene, coagulation factor 13, A1, interferon, alpha induced protein 27-like 2, formyl peptide receptor 2, KIAA0430, S100 calcium binding protein A8, and SLFN2.
Figure 3:
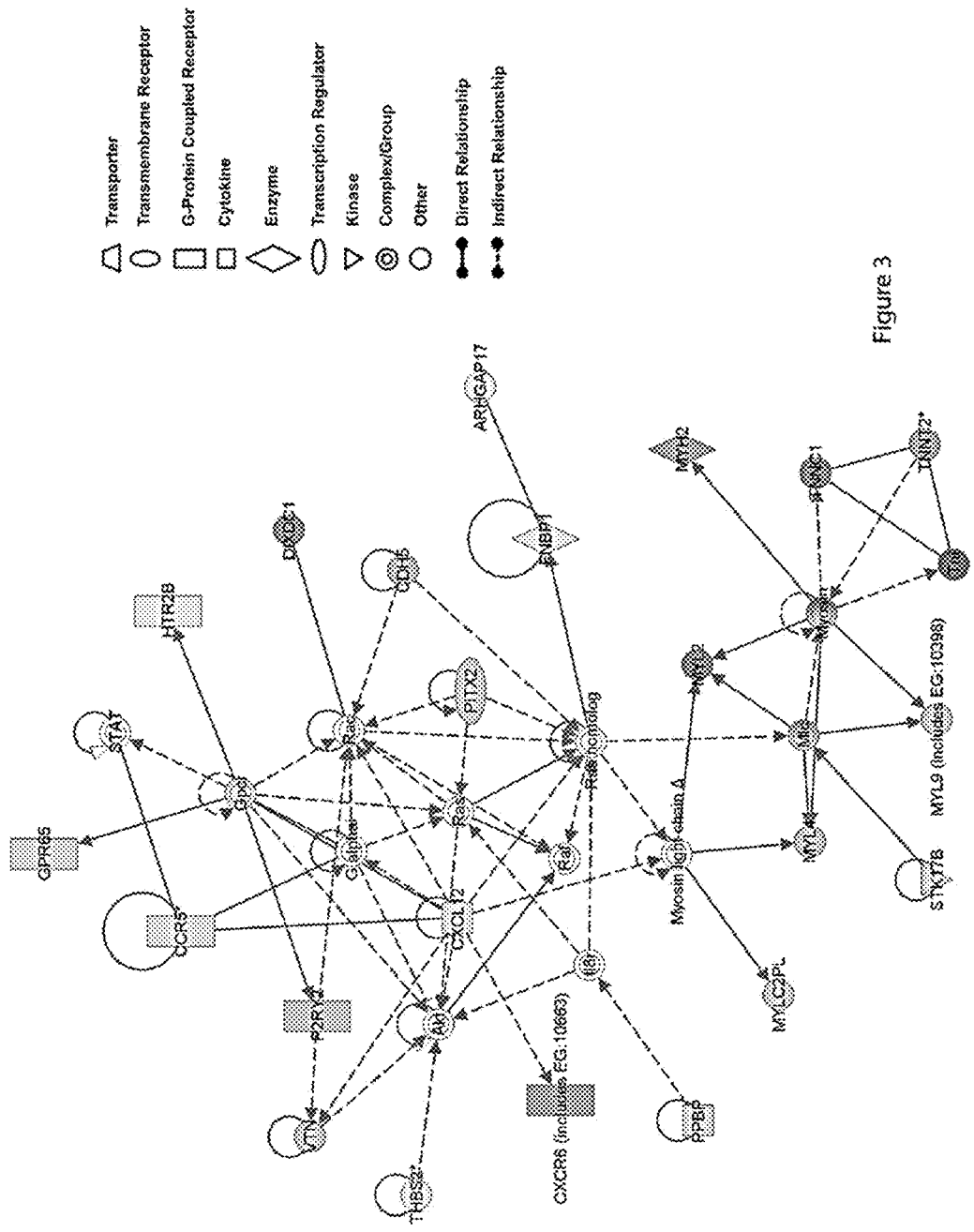
FIG. 3 depicts the results of a gene array analysis demonstrating that chronic sodium nitrite treatment altered the expression of genes involved in cardiovascular development and function, skeletal muscle development, and tissue development. Genes enhanced following sodium nitrite administration include CXCR6, VE-cadherin, DIX domain containing 1, myosin, heavy chain 2, myosin, light chain 2, myosin, light chain 4, myosin, light chain 9, P2rY2, paired like homeodomain 2, troponin C, type 1, troponin T, type 2 and vitronectin. Genes inhibited include Rho Gtpase activating protein 17, CCR5, CXCL12, CXCL7, formin binding protein 1, G protein coupled receptor 65, 5-HT receptor 2B, serine/threonine kinase 17b and thrombospondin 2.
Figure 4:
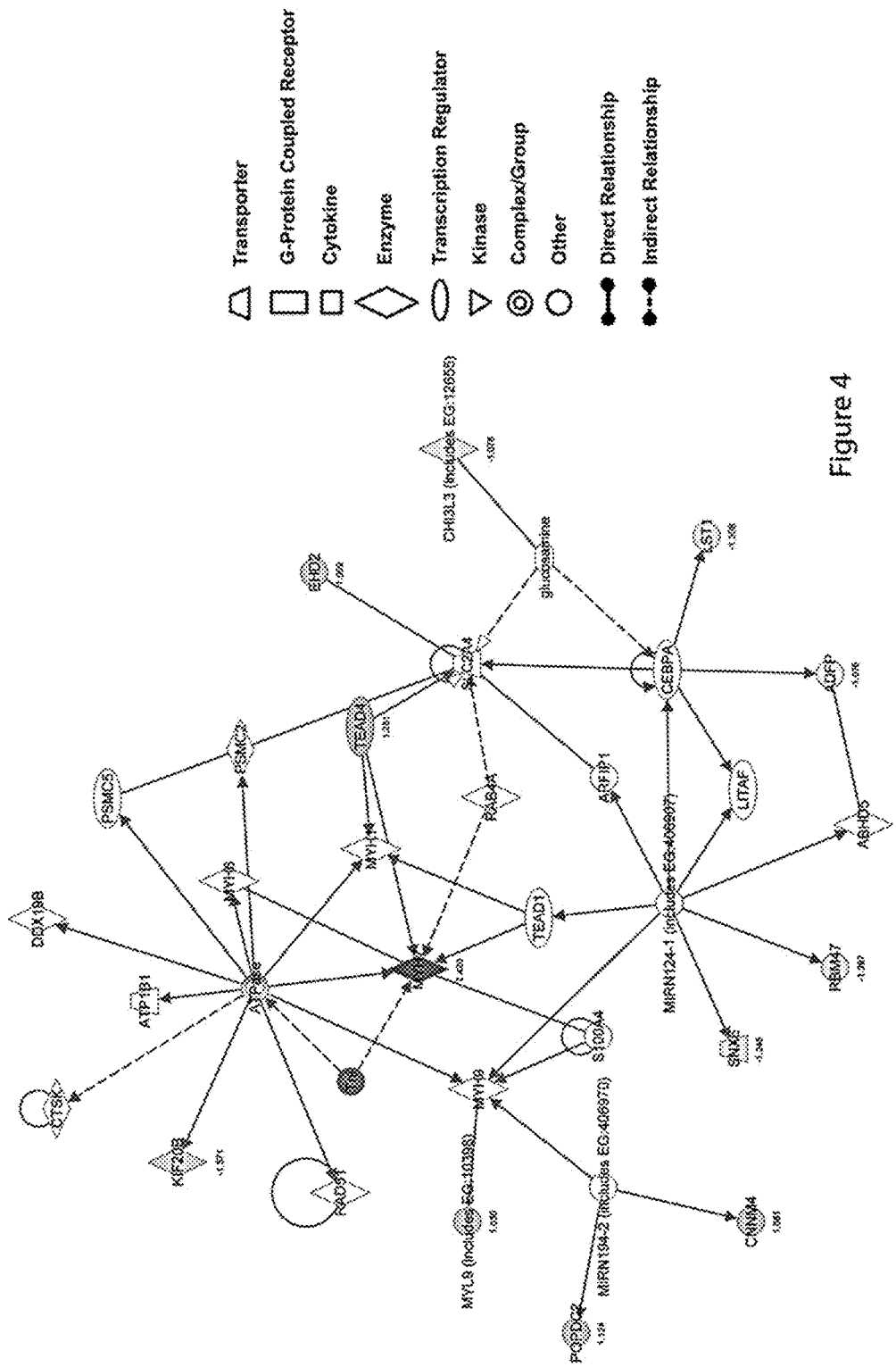
FIG. 4 depicts the results of a gene array analysis demonstrating that chronic sodium nitrite treatment altered the expression of genes involved in cellular assembly and organization, carbohydrate metabolism and molecular transport. Genes enhanced following sodium nitrite administration include cyclin M4, EH domain containing 2, myosin heavy chain 7, myosin light chain 9 regulatory, popeye domain containing 2 and TEA domain family member 4. Genes inhibited include adipose differentiated-related protein, chitinase 3-like 3, kinesin family member 20B, leukocyte specific transcript 1, RNA binding motif protein 47 and sorting nexin 6.
Figure 5:
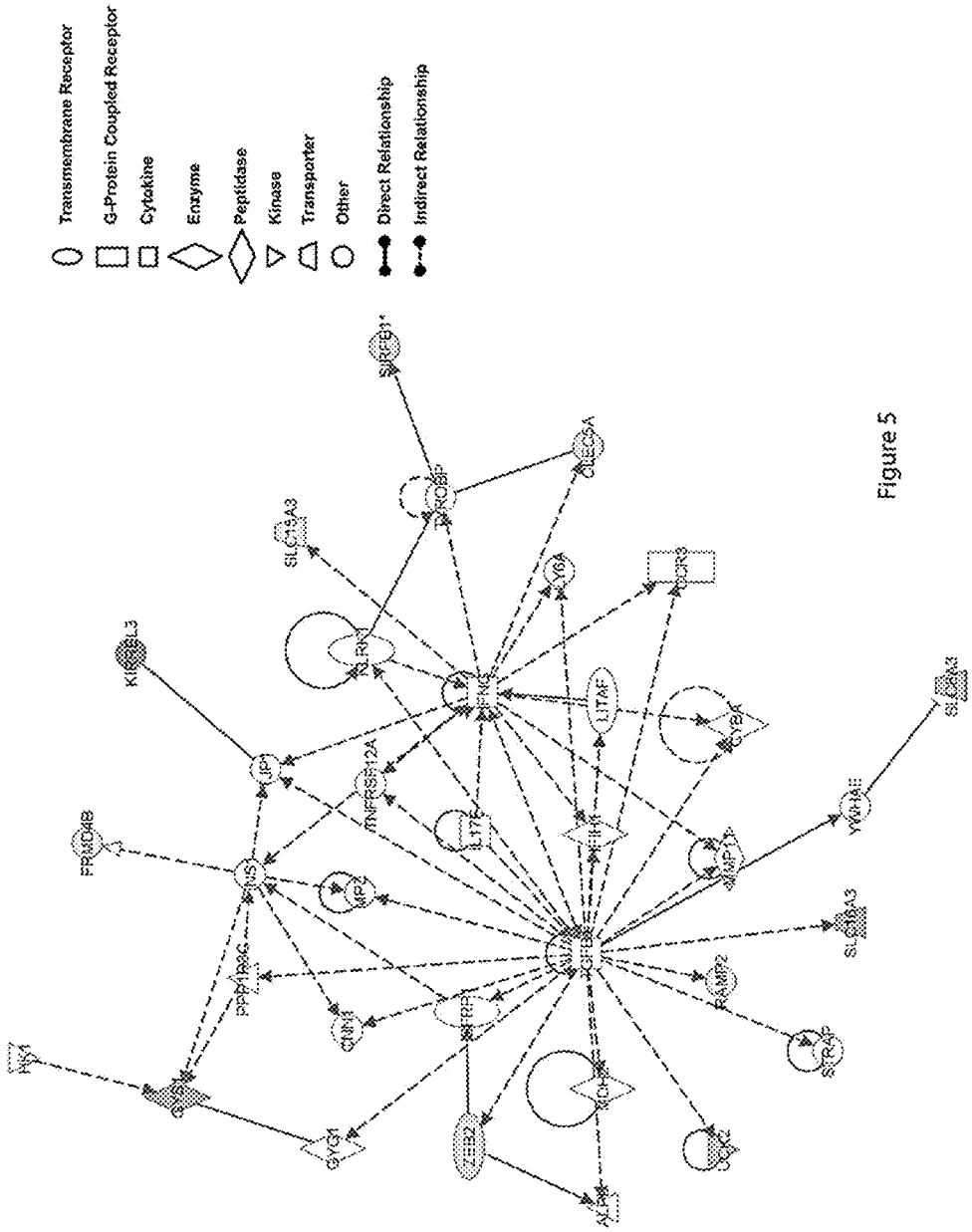
FIG. 5 depicts the results of a gene array analysis demonstrating that chronic sodium nitrite treatment altered the expression of genes involved in inflammatory response, neurological disease and cellular development. Genes enhanced following sodium nitrite administration include glycogen syntase 1 (muscle), kin of IRRE like 3, solute carrier family 16, member 3, solute carrier family 8, member 3 and uridine-cytidine kinase 2. Genes inhibited include C-type lectin domain family 5, A, FERM domain containing 4B, receptor (G protein coupled) activity modifying protein 2, signal-regulatory protein beta 1, solute carrier family 15, member 3 and zinc finger E-box binding homeobox 2.
Figure 6:
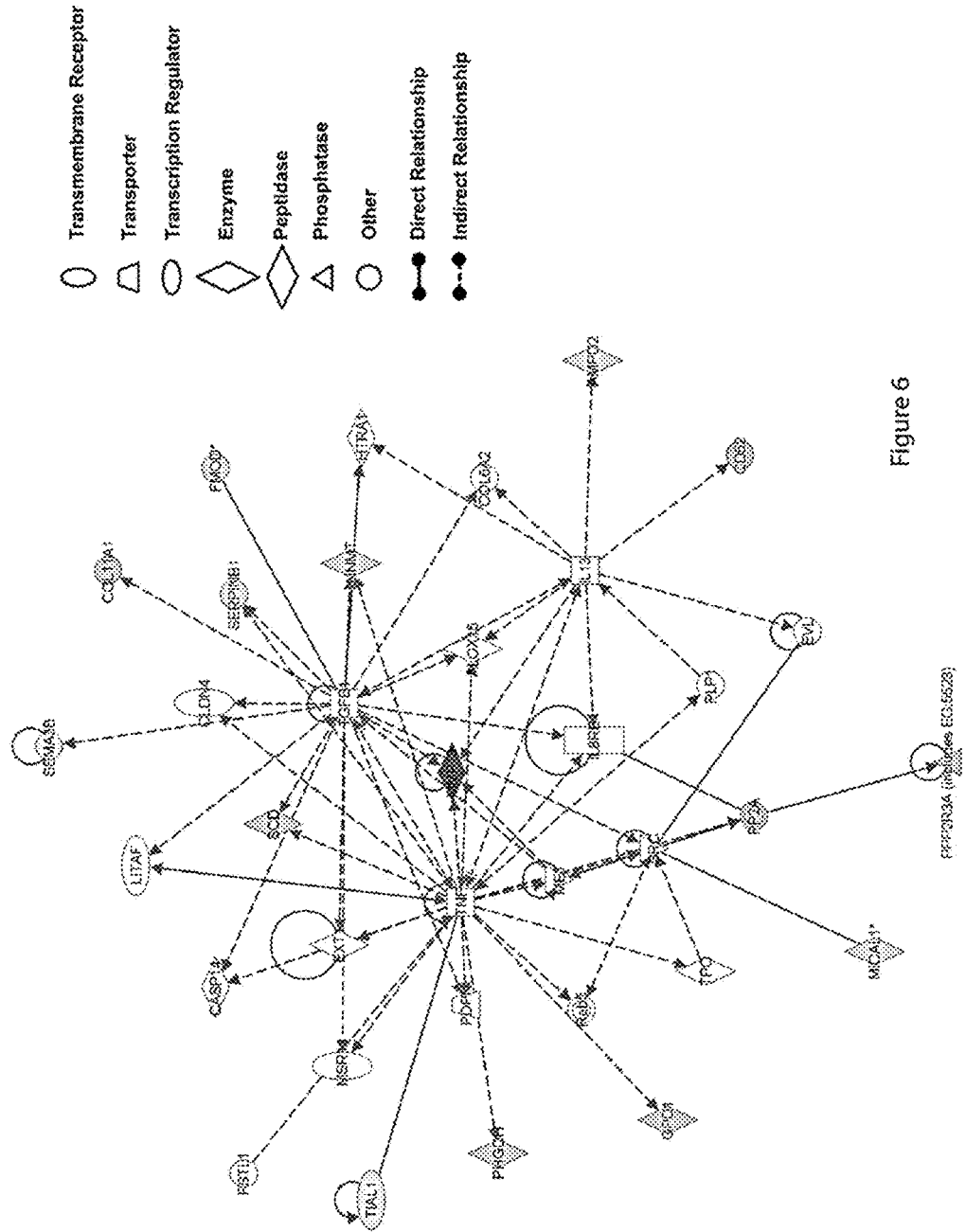
FIG. 6 depicts the results of a gene array analysis demonstrating that chronic sodium nitrite treatment altered the expression of genes involved in cancer, nervous system development and function and tissue morphology. Genes enhanced following sodium nitrite administration include adenosine monophosphate deaminase 2, CD52, collagen 11, alpha 1, fibromodulin, microtubule associated monoxygenase, calponin and LIM domain containing 1, matrix metalloproteinase 13, nicotinamide N-methyltransferase, phosphoglyerate dehydrogenase, stearoyl CoA desaturase, semaphorin 3B, serpin peptidase inhibitor, member 1 and TIA1 cytotoxic granule assoc RNA binding protein 1. Genes inhibited include glycerol-3-phosphate dehydrogenase and protein phosphatase 2, reg subunit B.

Results of the Ingenuity network analysis are shown in FIGS. 1-6. FIG. 1 shows that at day 3, chronic sodium nitrite treatment enhanced expression of genes involved in cardiovascular system development and function, tissue morphology, and carbohydrate metabolism. FIG. 1 also shows that at day 3, chronic sodium nitrite treatment inhibited expression of genes associated with innate and acquired immune responses at day 3. FIG. 2 shows that at day 3, chronic sodium nitrite treatment altered the expression of genes involved in antigen presentation, cell mediated immunity, and humoral mediated immunity. FIG. 3 shows that at day 3, chronic sodium nitrite treatment altered the expression of genes involved in cardiovascular development and function, skeletal muscle development, and tissue development. FIG. 4 shows that at day 3, chronic sodium nitrite treatment altered the expression of genes involved in cellular assembly and organization, carbohydrate metabolism and molecular transport. FIG. 5 shows that at day 3, chronic sodium nitrite treatment altered the expression of genes involved in inflammatory response, neurological disease and cellular development. FIG. 6 shows that at day 7, chronic sodium nitrite treatment altered the expression of genes involved in cancer, nervous system development and function and tissue morphology. Chronic sodium nitrite treatment enhanced expression of genes associated with tissue remodeling at day 7. These findings suggested that chronic sodium nitrite treatment accelerated tissue healing and recovery by augmenting angiogenic responses involving redox dependent pathways while diminishing inflammatory responses.

Figure 7A:
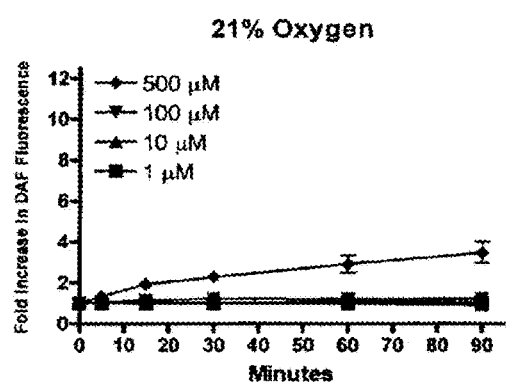
FIGS. 7A and 7B depict an analysis of nitric oxide production in iliac vein smooth muscle cells grown in various concentrations of sodium nitrite for 24 hours.
Figure 7B:
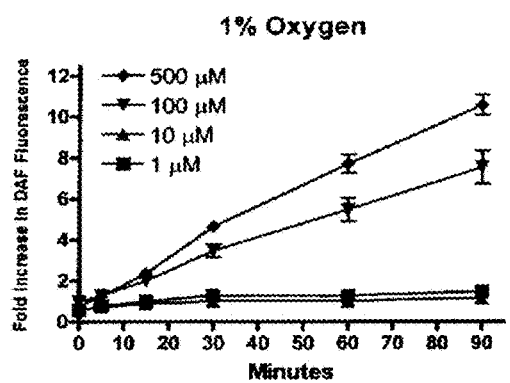
Figure 8:
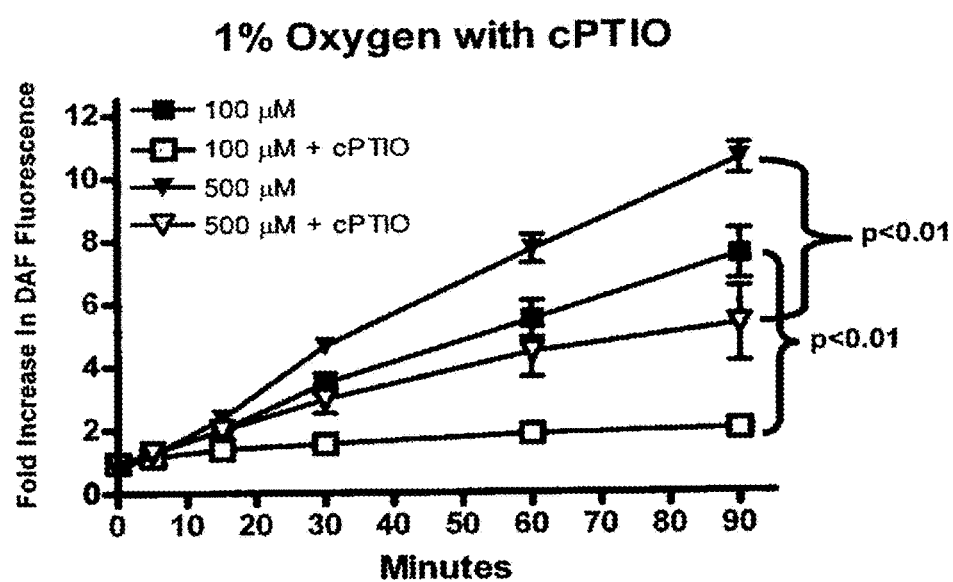
FIG. 8 depicts an analysis of the effect of the NO scavenger, cPTIO, on nitric oxide production in illiac vein smooth muscle cells.
Figure 9A:
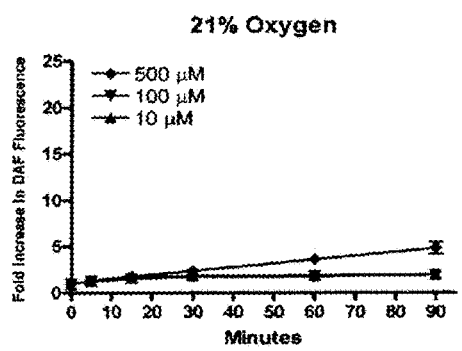
FIGS. 9A and 9B depict an analysis of nitric oxide production in aortic smooth muscle cells grown in various concentrations of sodium nitrite for 24 hours.
Figure 9B:
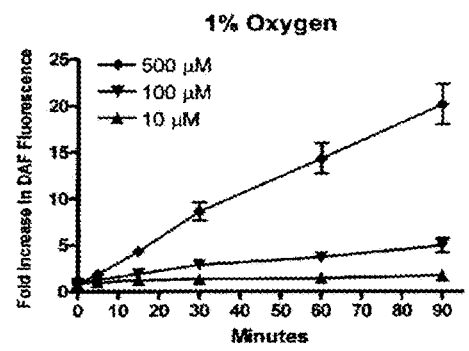
Figure 10:
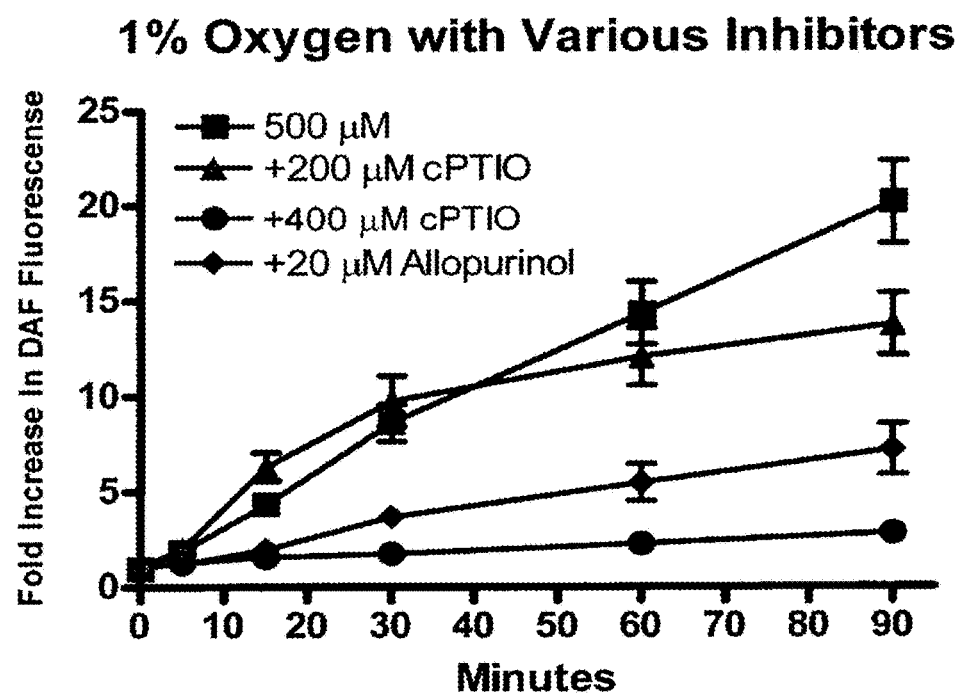
FIG. 10 depicts an analysis of the effect of various inhibitors on nitric oxide production in aortic smooth muscle cells.
Figure 11A:
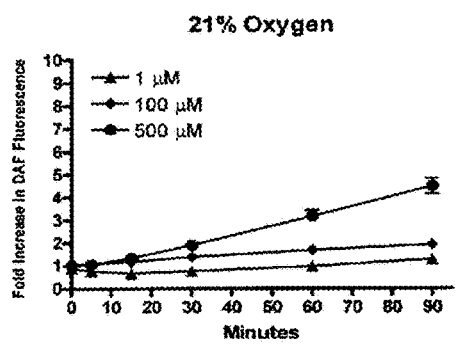
FIGS. 11A and 11B depict an analysis of nitric oxide production in coronary artery endothelial cells grown in various concentrations of sodium nitrite for 24 hours.
Figure 11B:
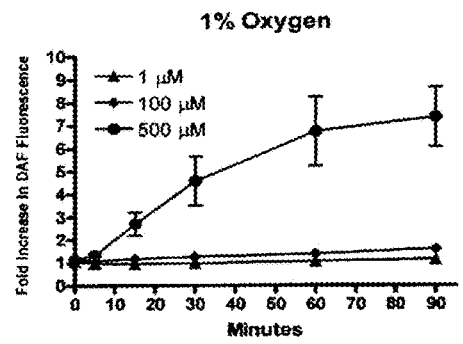
Figure 12:
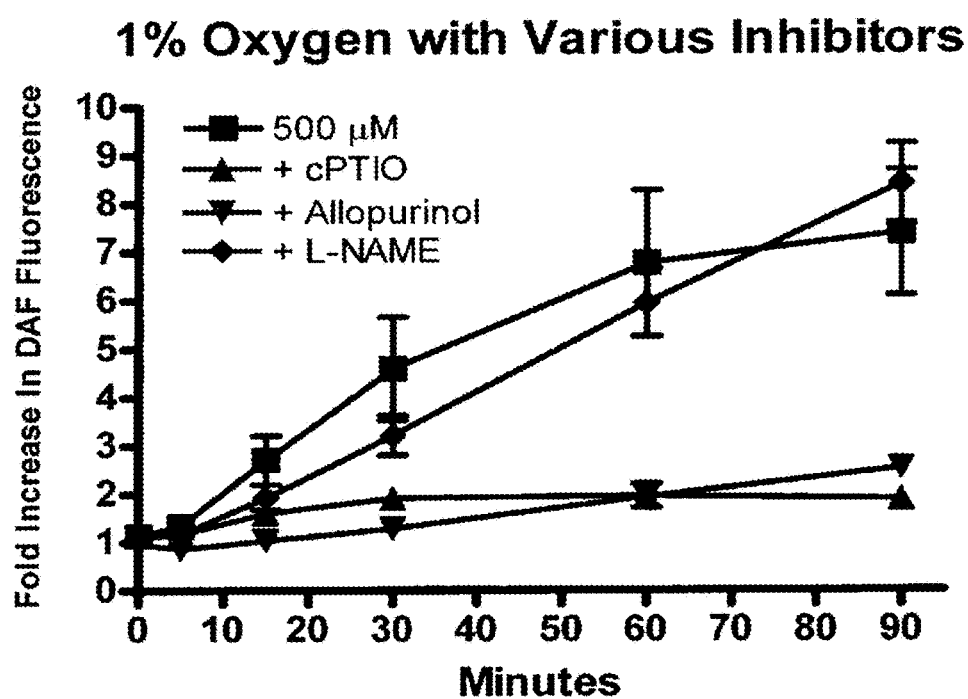
FIG. 12 depicts an analysis of the effect of various inhibitors on nitric oxide production in coronary artery endothelial cells.
Figure 14:
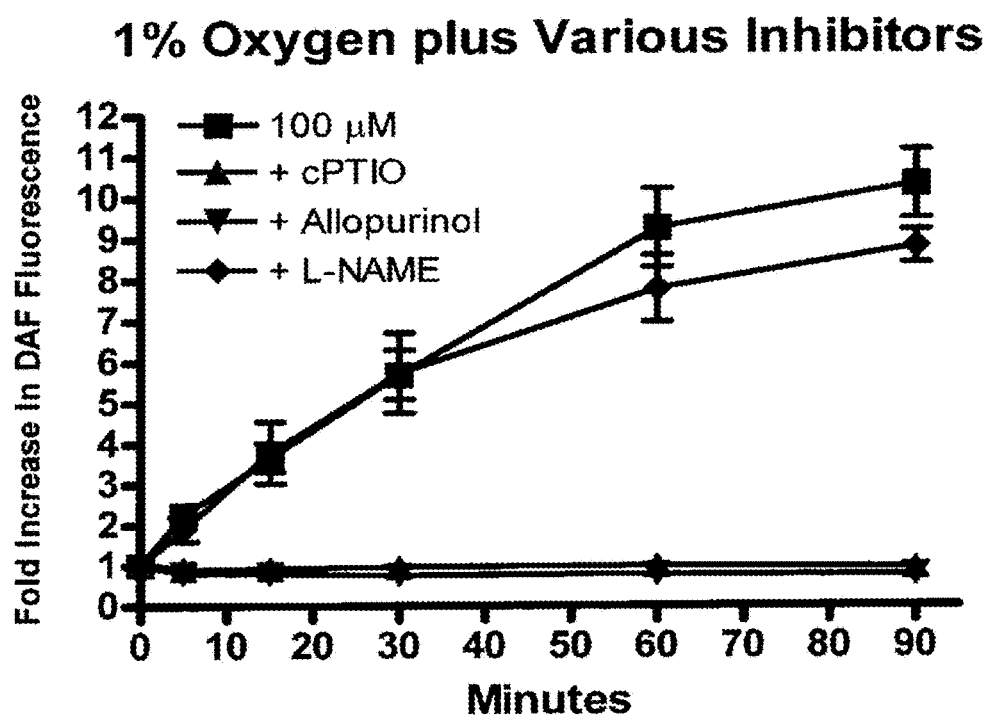
FIG. 14 depicts an analysis of the effect of various inhibitors on nitric oxide production in umbilical vein endothelial cells.
Figure 15A:
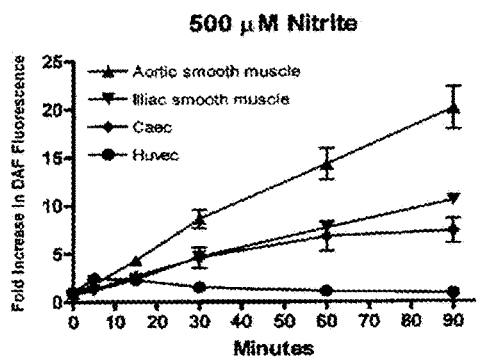
FIGS. 15A and 15B depicts an analysis of nitric oxide production in smooth muscle and endothelial cells grown in various concentrations of sodium nitrite for 24 hours.
Figure 15B:
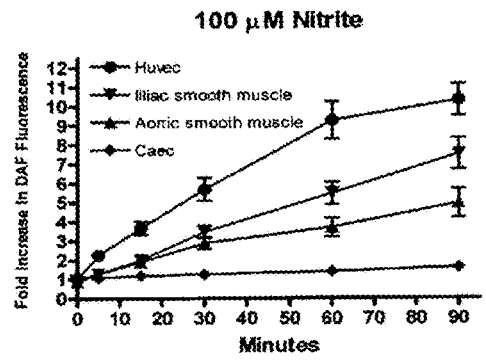
Figure 16:
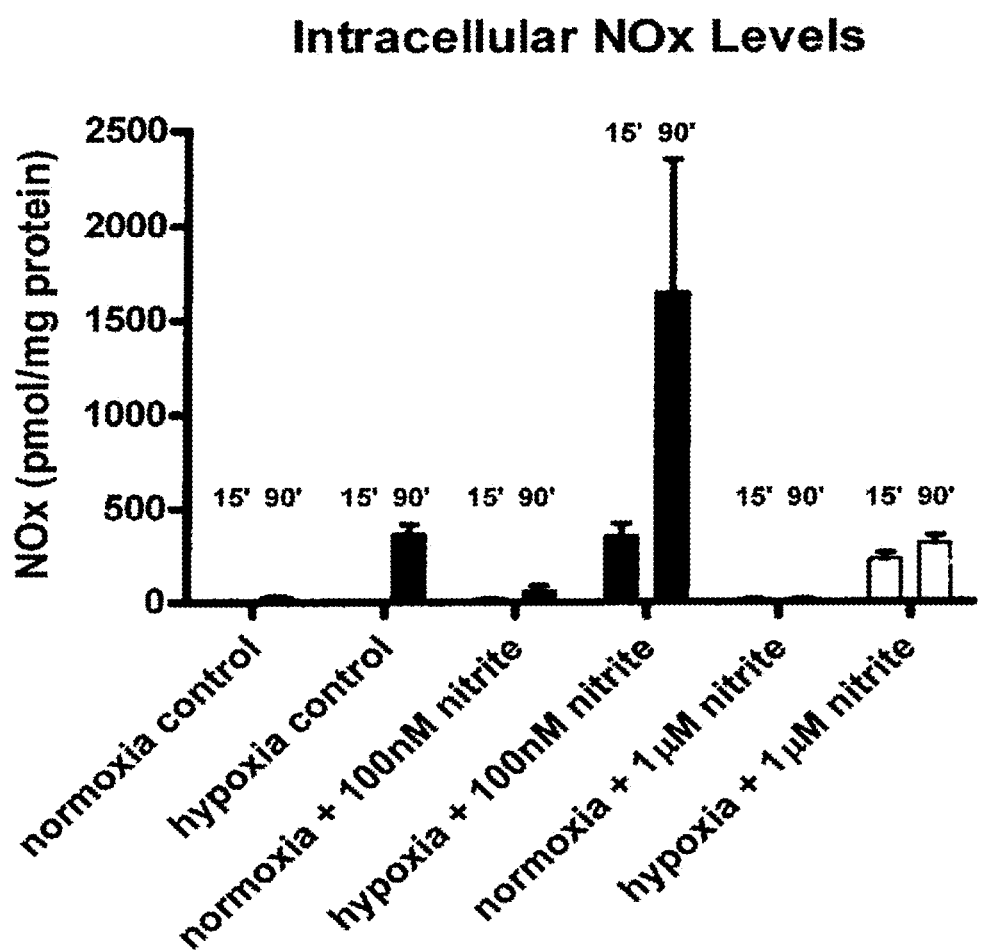
FIG. 16 depicts the chemiluminescent detection of nitrite/nitric oxide during hypoxia.

Example 3 Sodium Nitrite Reduction to Nitric Oxide in Human Iliac Vein Smooth Muscle Cells, Aortic Smooth Muscle Cells, Coronary Artery Endothelial Cells and Umbilical Vein Endothelial Cells Human iliac vein smooth muscle cells, aortic smooth muscle cells, coronary artery endothelial cells and umbilical vein endothelial cells were cultured in normal 21% or low oxygen (1%) conditions in the presence or absence of increasing doses of sodium nitrite and intracellular nitric oxide levels were determined as described in Example 1. The effect of specific inhibitors of NO production, carboxy PTIO (2-(4-Carboxyphenyl)-4,4,5,5-tetramethylimidazoline-1-oxyl-3-oxide), allopurinol and L-NAME, was also analyzed. Both smooth muscle and endothelial cells reduced nitrite to NO under hypoxic conditions. Results for iliac vein smooth muscle cells are shown in FIGS. 7A, 7B and 8; results for aortic smooth muscle cells are shown in FIGS. 9A, 9B and 10; results for coronary artery cells are shown in FIGS. 11A, 11B and 12, results for umbillical vein cells are shown in FIGS. 13A, 13B and 14. Results for the different cell types at 500 uM and 100 uM sodium nitrite are shown in FIGS. 15A and 15B respectively. Nitrite reduction by smooth muscle cells required higher concentrations of exogenous nitrite resulting in large increases in DAF fluorescence. Endothelial cells also reduced nitrite to NO at lower concentrations of exogenous nitrite. NO levels were also measured in cultured cells under hypoxic and normoxic conditions in the presence or absence of either 100 nM or 1 uM sodium nitrite. As shown in FIG. 16, exposure to lower concentrations, but not higher concentrations, of sodium nitrite resulted in a significant increase in intracellular NO levels.

Figure 17:
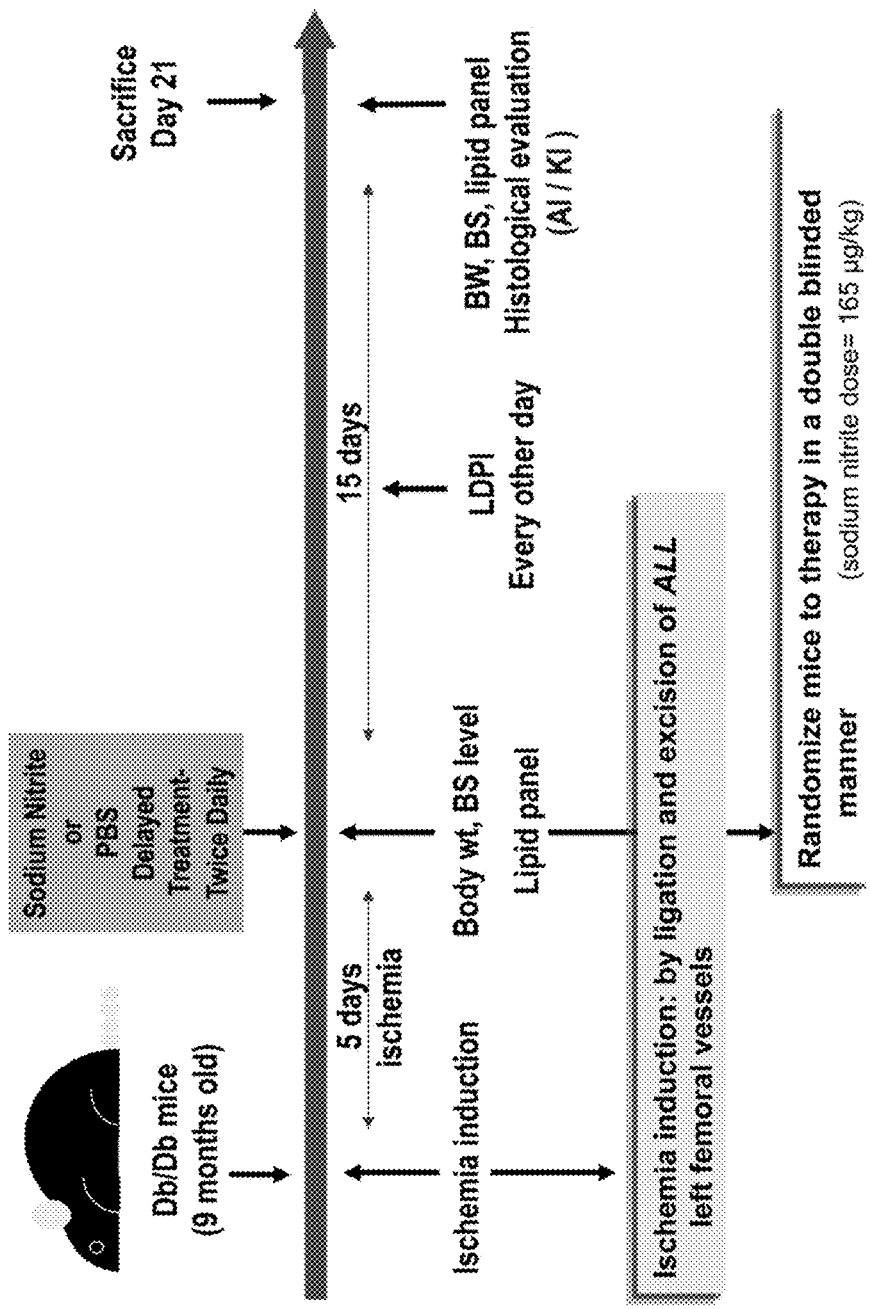
FIG. 17 depicts the experimental design of a study analyzing the effect of delayed chronic sodium nitrite treatment in an aged diabetes mouse model.

Example 4 Chronic Sodium Nitrite Treatment Restored Ischemic Hind Limb Blood Flow in an Aged Diabetic Mouse Model The effect of chronic sodium nitrite treatment on ischemic hind limb blood flow was assayed in an aged diabetic mouse model according to the experimental design shown in FIG. 17.

B6.BKS-Lepr$^{db/db}$ diabetic mice were purchased from Jackson's laboratory and housed in the animal center of LSU Health Sciences Center for 6 months. Surgical hind limb ischemia was created in 9 month-old male (Db/Db) type-2 diabetic mice. The mice were anesthetized by isoflurane inhalation and the left groin area was shaved and naired. The left external iliac artery and vein, left femoral artery and vein, left saphenous artery and vein and deep femoral and circumflex arteries and veins were ligated, cut, and excised to obtain a mouse model of critical hind limb ischemia. Five days after surgery, animals received either sodium nitrite (165 ug/kg) or PBS control treatment as described in example 1. All treatments were performed in a double-blinded manner.

Laser Doppler blood flows were measured using a Vasamedics Laserflo BPM2 device in the gastrocnemius pre-ligation, post-ligation and on days 1, 3, 5, 7, 9, 11, 13, 15, 17, 19 and 21 post-ligation. Blood vessels visible through the skin were avoided to ensure readings indicative of muscle blood flow. Measurements were recorded as milliliter of blood flow per 100 grams of tissue per minute. Percent blood flows were calculated as: a/b×100 where a=ischemic limb average flow and b=non-ischemic limb average flow.

Figure 20:
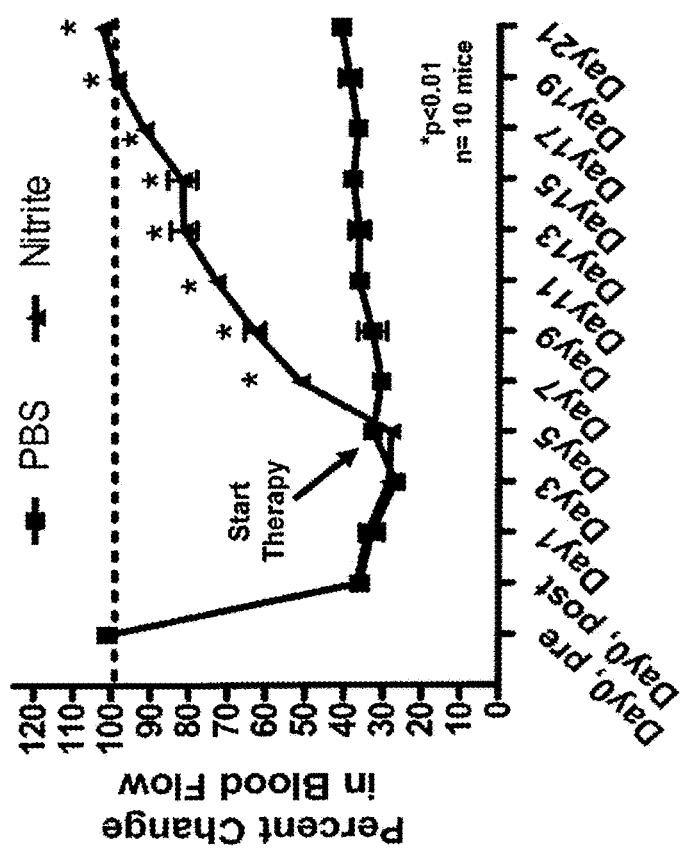
FIG. 20 depicts the results of an analysis demonstrating that chronic sodium nitrite treatment restored hind-limb blood flow in an aged diabetic mouse model.

As shown in FIG. 20, delayed sodium nitrite treatment restored ischemic hind-limb blood flow in aged diabetic mice. Blood flow in the ischemic-hind limbs of the nitrite-treated animals was significantly greater than that of the PBS-treated control animals at all time points analyzed and approached preligation levels by the end of the study.

Example 5 Effect of Chronic Sodium Nitrite Treatment on Weight, Blood Glucose and Blood Lipids in an Aged Diabetic Mouse Model We analyzed the effect of chronic sodium nitrite treatment on weight, blood glucose and blood lipids in an aged diabetic mouse model. Blood glucose measurements were taken using Ascensia Elite blood glucose test strips and a Bayer Glucometer Elite. Delayed chronic sodium nitrite treatment did not alter body weight or blood glucose levels in aged diabetic mice, as shown in FIGS. 18A and 18B respectively.

Figures 19A, 19B:
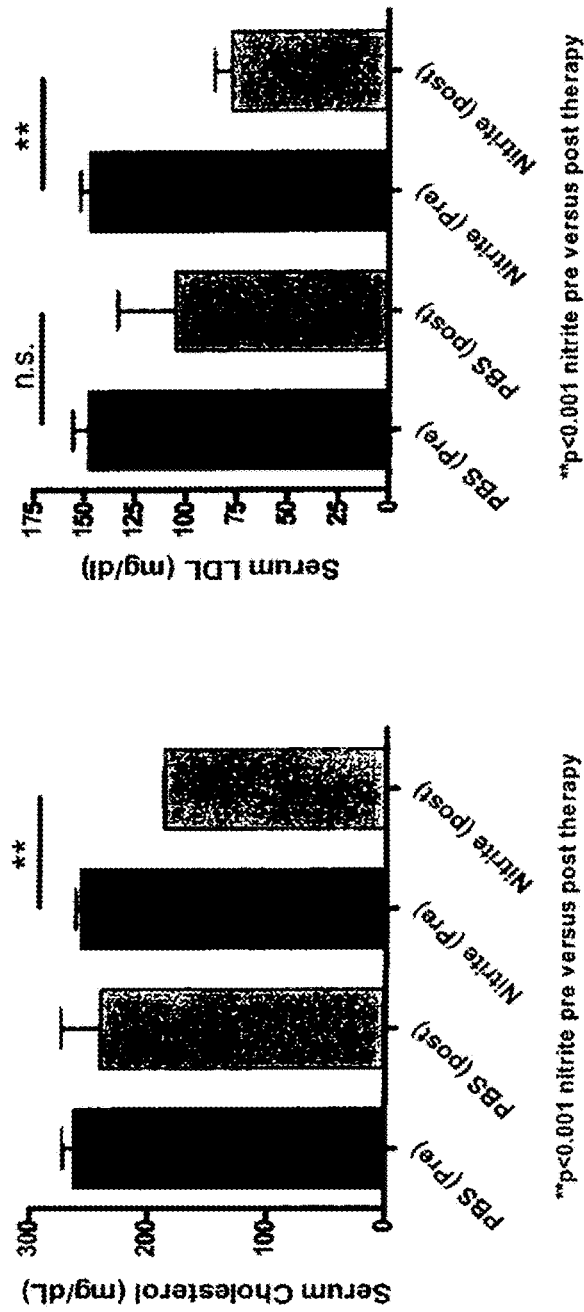
FIGS. 19A and 19B depict the results of an analysis of the effect of chronic sodium nitrite treatment on blood lipids in an aged diabetes mouse model.

Plasma total cholesterol and LDL levels were determined using a Siemens Vista Clinical Chemistry analyzer. Delayed chronic sodium nitrite treatment significantly decreased serum cholesterol in aged diabetic mice as shown in FIG. 19A. Delayed chronic sodium nitrite treatment significantly decreased serum LDL in aged diabetic mice as shown in FIG. 19B.

Example 6 Effect of Chronic Sodium Nitrite Treatment on Tissue Vascular Density and Cell Proliferation in an Aged Diabetic Mouse Model The effect of delayed chronic sodium nitrite treatment on tissue vascular density and cell proliferation was assayed in the aged diabetic mouse model described in Example 4.

Capillary myofiber ratio. The gastrocnemius muscles from ischemic and non-ischemic hind limbs were removed, dissected, and embedded in OCT freezing medium. Then tissues were fixed with 95% ethanol and 5% glacial acetic acid at −20 C for I hour. Endogenous Peroxidase quenching is performed in 20% hydrogen peroxide in methanol for 20 minutes. Slides are then washed with PBS three times. Sections were blocked with 10 cc of 0.1% PBS-BSA (Bovine serum albumin) (0.5 gram BSA in 10 cc of PBS=5% PBS-BSA, then 9.8 cc of PBS+0.2 cc of 5% PBS-BSA=0.1% PBS-BSA) and blocking serum (VECTASTAIN ABC-Mouse IgG kits with horseradish peroxidase enzymes) for one hour. Primary antibody (CD 31 antibody ab28364 Abcam) was diluted in 00.1% PBS-BSA (1:50 dilution) and tissue was incubated overnight at 4 C in a humidifier box.

Slides were then washed in PBS thrice, incubated in 0.5% biotinylated secondary antibody and 0.1% PBS-BSA for one hour at room temperature in humidifier box. In the mean time, Avidin-Biotin complex (ABC) was prepared (2 drops of A, 2 drops of B in 5 cc of 0.1% PBS-BSA) and incubated for one hour. Slides were washed in PBS after one hour incubation with secondary antibody, and incubated in ABC for one hour at room temperature in a humidifier box. Tissue was then again washed in PBS. NovaRED stain (Vector NovaRED substrate kit for peroxidase; catalog number SK 4800) was then prepared by adding 3 drops of reagent 1, 2 drops of each reagent 2, reagent 3 and hydrogen peroxide in 5 cc of distilled water. Tissues were then incubated in NovaRed stain for 10 min at room temp in a humidifier box, and then washed in distilled water for 5 minutes. Counterstain was then performed with hematoxylin (Vector Hematoxylin QS, H-3404) for 45 seconds and then washed with distilled water.

Tissue was then dehydrated with ethanol (95%, 100% for 10 and 15 min respectively) and xylene for 30 minutes. Slides were mounted with permount and cover slips. From each mouse, 5 random fields on 2 different sections (approximately 3 mm apart) were photographed with a digital camera (Olympus, Tokyo, Japan). The number of CD31-positive vessels and muscle fibers were counted manually in a blind fashion in per mm$^2$. Finally ratio between CD31 and muscle fibers was calculated.

The tissue vascular density/angiogenic index was measured as follows. The gastrocnemius muscles from ischemic and non-ischemic hind limbs were removed, dissected, and embedded in OCT freezing medium. Frozen tissue blocks were cut into 5 μm sections and slides prepared. A primary antibody against PECAM-1 was added at a 1:200 dilution and incubated at 37° C. for 1 hour. Slides were then washed and a Cy3 conjugated secondary antibody was added at a 1:250 dilution and incubated at room temperature for 1 hour. Slides were once again washed and mounted with cover slips using Vectashield DAPI. A minimum of four slides per hind limb with three sections per slide were prepared for vascular density analysis. A minimum of two fields were acquired per section of muscle. Images were captured using a Hamamatsu digital camera in conjunction with a Nikon TE-2000 epifluorescence microscope (Nikon Corporation, Japan) at 200× magnification for CD31 and DAPI staining. Simple PCI software version 6.0 (Compix Inc., Sewickly, Pa., USA) was used to determine the area CD31 and DAPI positive staining. Tissue vascular density was determined as the ratio between CD31 positive areas and DAPI positive regions.

Figures 21A, 21B:
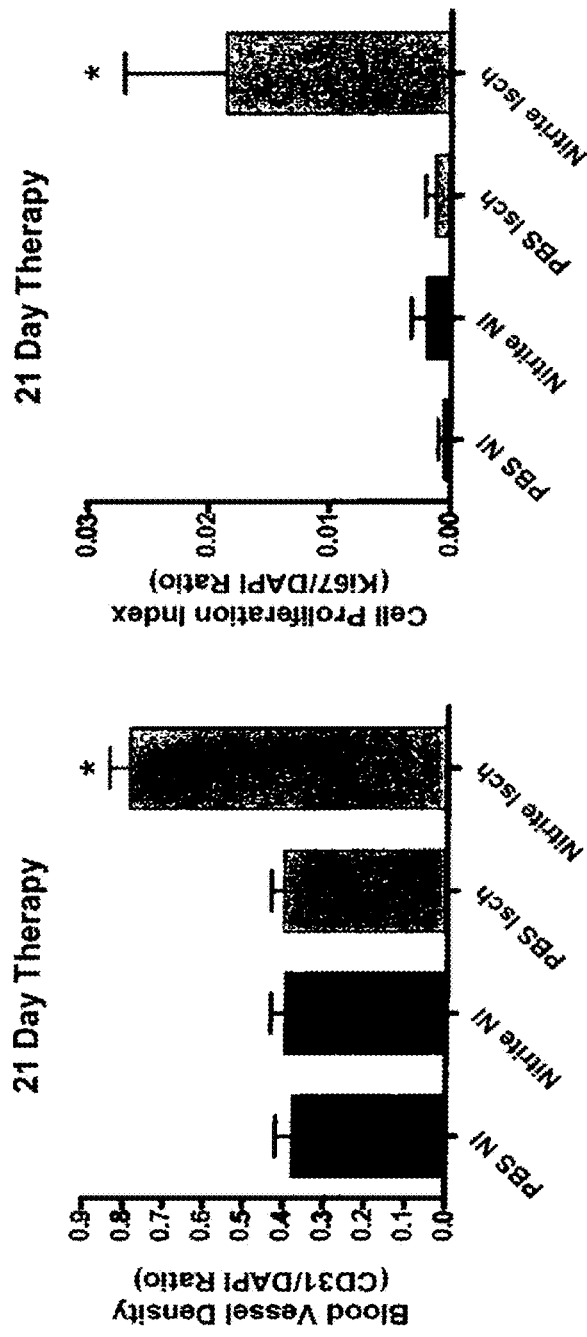
FIGS. 21A and 21B depicts the results of an analysis demonstrating that chronic sodium nitrite treatment increased vascular density and cell proliferation in an aged diabetic mouse model.

As shown in FIG. 21A, delayed chronic sodium nitrite treatment significantly increased blood vessel density in ischemic but not non-ischemic tissues of aged diabetic mice Endothelial Cell proliferation assay. The gastrocnemius muscles from ischemic and non-ischemic hind limbs were removed, dissected, and embedded in OCT freezing medium. Frozen tissue blocks were cut into 5 μm sections and slides prepared. A primary antibody against PECAM-1 was added at a 1:200 dilution along with anti-Ki67 (1:350 dilutions) and incubated at 37° C. for 1 hour. Slides were then washed and a Cy3 conjugated secondary antibody was added at a 1:250 dilution along with anti-rabbit Ig antibody at a 1:150 dilution and incubated at room temperature for 1 hour. Slides were once again washed and mounted with cover slips using Vectashield DAPI. A minimum of four slides per hind limb with three sections per slide were prepared for endothelial cell proliferation analysis. A minimum of two fields were acquired per section of muscle. Images were captured using a Hamamatsu digital camera in conjunction with a Nikon TE-2000 epifluorescence microscope (Nikon Corporation, Japan) at 200× magnification for CD31 and DAPI staining. Simple PCI software version 6.0 (Compix Inc., Sewickly, Pa., USA) was used to determine the area CD31 and DAPI positive staining as well as area Ki67 and DAPI staining. Cellular proliferation was determined as the ratio between regions positive for Ki67 and DAPI positive area.

Tunnel assay: Hind limb ischemic tissue and non-ischemic tissues (gastrocnemius muscles) were collected at day 21. Apoptosis was determined (groups PBS and Na2S) using the Tunel staining kit (Promega, Inc) according to manufacturer's recommendations. 5 μm formalin fixed sections was prepared and mounted with Vectashield plus 4, 6-diamidino-2 phenylidole (DAPI) (Vector Laboratories, Burlingame, Calif.). Immunofluorescence (green Tunnel staining at 488 nm) was measured from five random fields per slide for quantification of the extent of apoptosis. Images were captured using a Hamamatsu digital camera in conjunction with a Nikon TE-2000 epifluorescence microscope (Nikon Corporation, Japan). Simple PCI software version 6.0 (Compix Inc., Sewickly, Pa., USA) was used to determine the area tunnel positive and DAPI positive staining. Apoptosis of cells was determined as the ratio between regions positive for tunel and DAPI positive area.

Figures 22A, 22B:
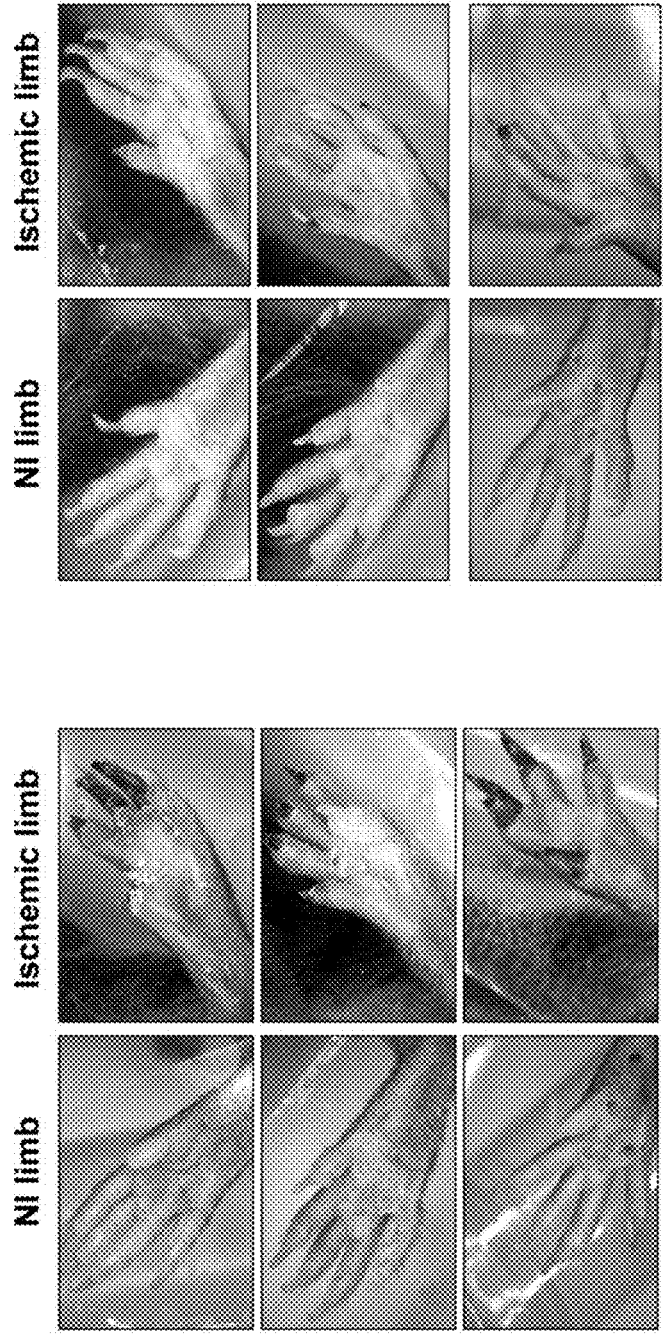
FIGS. 22A and 22B depict the gross appearance of foot pads of aged diabetic mice receiving chronic sodium nitrite treatment.

As shown in FIG. 21B, delayed chronic sodium nitrite treatment significantly increased epithelial cell proliferation in ischemic but not non-ischemic tissues of aged diabetic mice Example 7 Effect of Delayed Chronic Sodium Nitrite Treatment on Tissue Necrosis in an Aged Diabetic Mouse Model The effect of delayed chronic sodium nitrite treatment on gross footpad morphology in the aged diabetic mouse model described in Example 4 is shown in FIG. 22. As shown in FIG. 22A, ischemic hindlimbs of PBS control mice showed extensive necrosis and digit loss. In contrast, the animals receiving delayed chronic sodium nitrite treatment showed no digit loss and minimal necrosis and shown in FIG. 22B.

Figure 23:
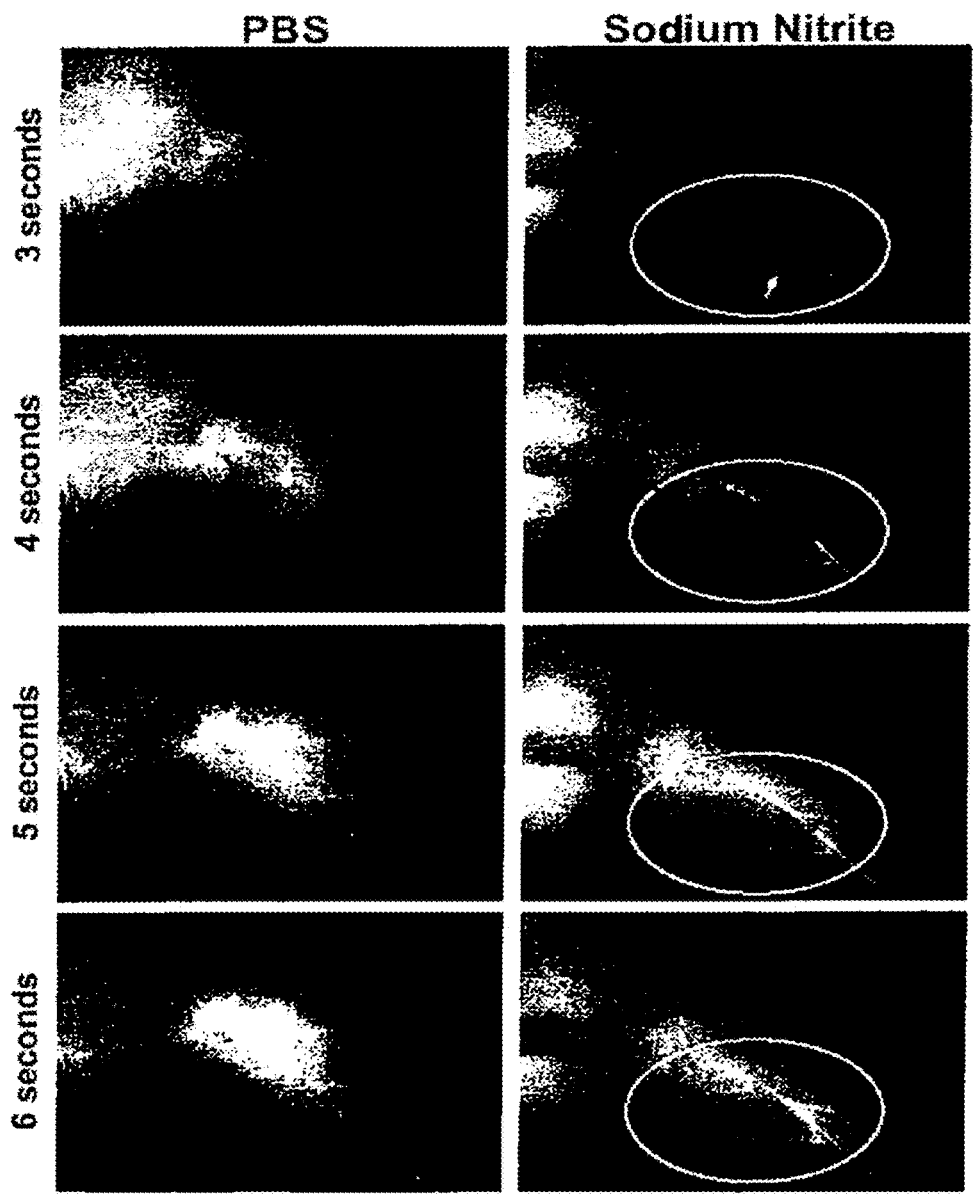
FIG. 23 depicts the results of an angiographic analysis mouse ischemic hindlimbs.

Example 8 Effect of Delayed Chronic Sodium Nitrite Treatment on Angiogenesis in C57Bl/6J Mice C57Bl/6J mice were treated with delayed chronic sodium nitrite treatment according to the method in example 1. Representative fluorescence angiograms using the SPY imaging system are shown in FIGS. 23A and 23B. PBS-treated control animals are shown in FIG. 23A; nitrite treated animals are shown in FIG. 23B. As shown in FIG. 23B, nitrite-treatment significantly increased arteriogenesis (arrows at 4 seconds blush time.)

Figures 24A, 24B:
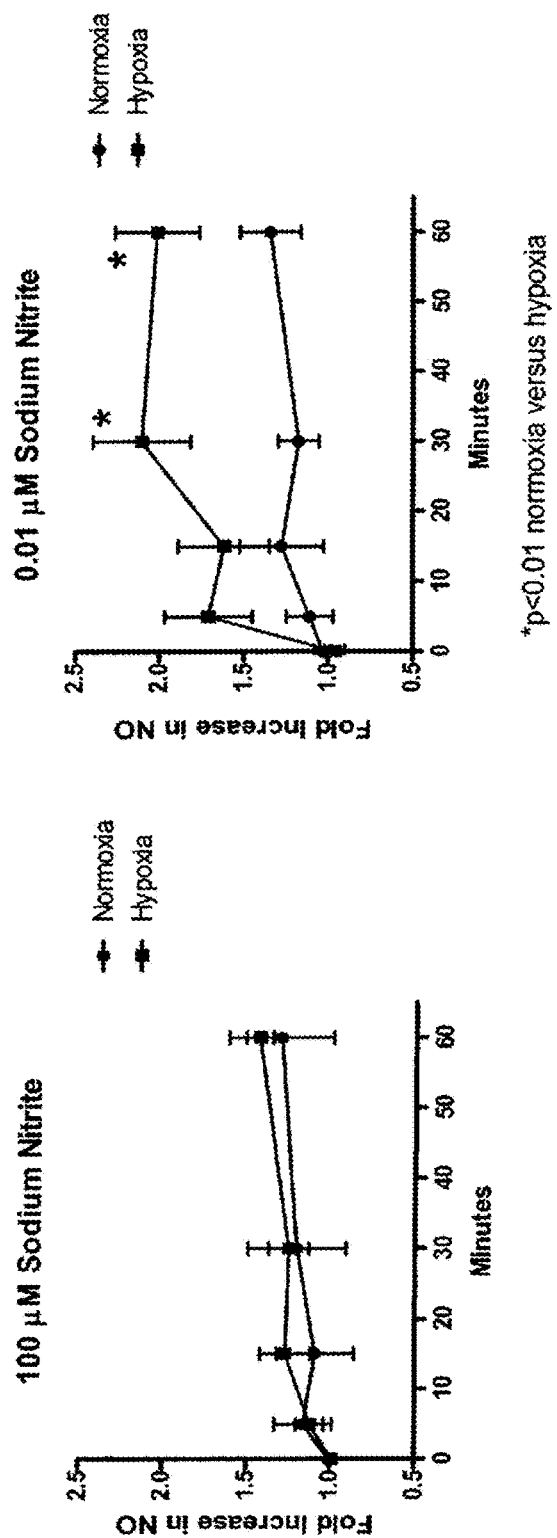
FIGS. 24A and 24B depicts the results of an analysis of NO production in C2C12 myoblast cells in hypoxic conditions treated with 100 uM or 0.01 uM sodium nitrite.

Example 9 C2C12 Myoblasts Selectively Reduce Low-Dose Sodium Nitrite to NO During Hypoxia C2C12 myoblasts were incubated in sodium nitrite under conditions of normoxia and hypoxia according to the methods in Example 1. As shown in FIG. 24A, incubation in 100 uM sodium nitrite did not alter NO levels. In contrast, as shown in FIG. 24B, levels of NO were significantly increased during incubation in 0.01 uM sodium nitrite, but only in hypoxic conditions.

Example 10 Low-Dose Sodium Increases Myogenin Expression Under Hypoxia In Vivo in Mouse Gastrocnemius Muscle and in Cell Culture in C2C12 Myoblasts Gene array analysis (performed according to the methods of Examples 1 and 3) of ischemic mouse hindlimb grastrocnemius muscle showed that myogenin mRNA levels were significantly increased tissue from nitrite-treated animals, as shown in FIG. 25A. C2C12 myoblast cells cultured in the presence of decreasing levels of sodium nitrite, showed a dose-dependent increase in myogenin mRNA under hypoxic conditions that was inversely correlated with nitrite concentration. Levels of mygenin mRNA were highest in cells cultured at the lowest dose, i.e. 0.01 uM sodium nitrite.

A number of embodiments of the invention have been described. Nevertheless, it will be understood that various modifications may be made without departing from the spirit and scope of the invention. Accordingly, other embodiments are within the scope of the following claims.

Wherefore I claim:

1. A method of treating peripheral neuropathy in a mammalian subject, the method comprising:
    a) identifying a mammalian subject who has peripheral neuropathy; and
    b) administering to the mammalian subject a pharmaceutical composition comprising one of sodium nitrite, potassium nitrite, calcium nitrite, or some combination thereof,
wherein the pharmaceutical composition is administered one of intraperitoneally, intravenously, subcutaneously, intramuscularly, sublingually, or orally;
the amount of sodium nitrite, potassium nitrite, calcium nitrite, or some combination thereof is a dose of about 0.5 μg/kg to about 5000 μg/kg and;
the pharmaceutical composition is administered until a cytokine profile generated from a tissue from the mammalian subject is found to be reduced to a level found in normal conditions for the tissue of the mammalian subject, the cytokine profile being at least one of TGFβ, IFNγ, or IL-17 and wherein the tissue is at or near the site of the peripheral neuropathy.

2. The method of claim 1, wherein the mammalian subject is a human.

3. The method of claim 1, wherein the pharmaceutical composition includes sodium nitrite.

4. The method of claim 1, wherein the nitrite is administered one or more times a day.

5. The method of claim 4, wherein the administration occurs for at least about two days; at least about three days; at least about four days; at least about five days; at least about six days; at least about seven days; at least about 10 days; at least about 15 days; or at least about twenty days.

6. The method of claim 1, wherein the dose is about 1 µg/kg to about 1000 µg/kg; about 0.5 µg/kg to about 500 µg/kg; about 0.5 µg/kg to about 250 pg/kg; about 0.5 pg/kg to about 100 µg/kg; or about 0.5 µg/kg to about 50 µg/kg.

7. The method of claim 1, wherein the dose is about 165 µg/kg; about 16.5 µg/kg; or about 8.25 µg/kg.

8. The method of claim 1, wherein the nitrite is administered to a circulating concentration in the subject of about 0.0005 µM to about 1.0 µM.

9. The method of claim 1, wherein the nitrite is administered to a circulating concentration in the subject of about 0.001 µM to about 0.03 µM, of about 0.01 µM to about 0.05 µM, or about 0.05 µM to about 0.5 µM.

10. The method of claim 9, wherein the nitrite is administered to a circulating concentration in the subject of about 0.5 µM, of about 0.3 µM, of about 0.03 µM; of about 0.003 µM; or of about 0.0015 µM.

11. The method of claim 1, further comprising monitoring whether the subject experiences reduced inflammation.

12. The method of claim 1, further comprising administering an anti-ischemic therapy, an antimicrobial agent, an analgesic agent, an anti-inflammatory agent, a chemotherapeutic agent or a growth factor.

13. The method of claim 1, wherein the sodium nitrite, potassium nitrite, calcium nitrite, or some combination thereof is the only peripheral neuropathy treating pharmaceutical compound in the pharmaceutical composition.

14. A method of treating peripheral neuropathy in a mammalian subject comprising:
  a) identifying a mammalian subject who has peripheral neuropathy; and
  b) administering to the mammalian subject a pharmaceutical composition comprising sodium nitrite, potassium nitrite, calcium nitrite, or some combination thereof, wherein the pharmaceutical composition is administered for a time and in an amount sufficient to treat the peripheral neuropathy; and wherein the pharmaceutical composition is administered transdermally such that the one of sodium nitrite, potassium nitrite, calcium nitrite, or some combination thereof passes through the dermis in an amount sufficient to treat the peripheral neuropathy; and the pharmaceutical composition is administered until a cytokine profile generated from a tissue from the mammalian subject is found to be reduced to a level found in normal conditions for the tissue of the mammalian subject, the cytokine profile being at least one of TGFβ, IFNγ, or IL-17 and wherein the tissue is at or near the site of the peripheral neuropathy.

15. The method of claim 14, wherein pharmaceutical composition is a preparation with a pH of between 7 and 11, inclusive.

16. A method of treating peripheral neuropathy in a mammalian subject comprising:
  a) identifying a mammalian subject who has peripheral neuropathy; and
  b) administering to the mammalian subject a pharmaceutical composition comprising a first therapeutic being one of sodium nitrite, potassium nitrite, calcium nitrite, or some combination thereof, wherein the first therapeutic is administered for a time and in an amount sufficient to treat the peripheral neuropathy;

wherein the pharmaceutical composition further includes a second therapeutic being at least one of anti-hypertensives, anti-diabetic agents, statins, anti-platelet agents, antibodies, immune suppressants, anti-inflammatory agents, antibiotics, or chemotherapeutics, wherein the second therapeutic is distinct from the first therapeutic, wherein the pharmaceutical composition is administered one of intraperitoneally, intravenously, subcutaneously, intramuscularly, sublingually, or orally; and the pharmaceutical composition is administered until a cytokine profile generated from a tissue from the mammalian subject is found to be reduced to a level found in normal conditions for the tissue of the mammalian subject, the cytokine profile being at least one of TGFβ, IFNγ, or IL-17 and wherein the tissue is at or near the site of the peripheral neuropathy.

17. The method of claim 16, wherein the pharmaceutical composition comprises one of clopidogrel, cilostazol, and some combination thereof.

* * * * *